US010286057B2

(12) United States Patent
Haynes et al.

(10) Patent No.: US 10,286,057 B2
(45) Date of Patent: May 14, 2019

(54) CYCLIC HIV-1 ENV V3 GLYCOPEPTIDE IMMUNOGENS

(71) Applicants: DUKE UNIVERSITY, Durham, NC (US); SLOAN-KETTERING INSTITUTE FOR CANCER RESEARCH, New York, NY (US); DANA-FARBER CANCER INSTITUTE, INC, Boston, MA (US)

(72) Inventors: Barton F. Haynes, Durham, NC (US); Hua-xin Liao, Durham, NC (US); Samuel Danishefsky, New York, NY (US); Peter Park, New York, NY (US); Joseph Sodroski, Boston, MA (US); Baptiste Aussedat, New York, NY (US); Yusuf Vohra, New York, NY (US)

(73) Assignees: Duke University, Durham, NC (US); Sloan-Kettering Institute for Cancer Research, New York, NY (US); Dana-Farber Cancer Institute, Inc., Boston, MA (US)

( * ) Notice: Subject to any disclaimer, the term of this patent is extended or adjusted under 35 U.S.C. 154(b) by 44 days.

(21) Appl. No.: 14/784,501

(22) PCT Filed: Apr. 15, 2014

(86) PCT No.: PCT/US2014/034189
§ 371 (c)(1),
(2) Date: Oct. 14, 2015

(87) PCT Pub. No.: WO2014/172366
PCT Pub. Date: Oct. 23, 2014

(65) Prior Publication Data
US 2016/0106827 A1    Apr. 21, 2016

Related U.S. Application Data

(60) Provisional application No. 61/811,992, filed on Apr. 15, 2013.

(51) Int. Cl.
*A61K 39/21* (2006.01)
*A61K 39/12* (2006.01)
*C07K 14/16* (2006.01)
*G01N 33/569* (2006.01)
*C07K 14/00* (2006.01)
*C07K 14/005* (2006.01)
*A61K 39/00* (2006.01)

(52) U.S. Cl.
CPC .............. *A61K 39/12* (2013.01); *A61K 39/21* (2013.01); *C07K 14/001* (2013.01); *C07K 14/005* (2013.01); *C07K 14/162* (2013.01); *G01N 33/56988* (2013.01); *A61K 2039/545* (2013.01); *A61K 2039/55566* (2013.01); *C12N 2740/16034* (2013.01); *C12N 2740/16134* (2013.01); *G01N 2333/16* (2013.01)

(58) Field of Classification Search
CPC .................. A61K 39/21; C07K 14/162; C12N 2740/16134
See application file for complete search history.

(56) References Cited

FOREIGN PATENT DOCUMENTS

| EP | 1738764 | 1/2007 |
|---|---|---|
| WO | 2013055908 | 4/2013 |
| WO | WO 2013/055908 A1 * | 4/2013 |
| WO | 2013085550 | 6/2013 |

OTHER PUBLICATIONS

Alving et al. "Adjuvants for human vaccines" Curr Opin Immunol. Jun. 2012;24(3):310-5.
Aussedat et al. "Chemical synthesis of highly congested gp120 V1V2 N-glycopeptide antigens for potential HIV-1-directed vaccines" J Am Chem Soc. Sep. 4, 2013;135(35):13113-20.
Aussedat et al. "Total synthesis of the a-subunit of human glycoprotein hormones: toward fully synthetic homogeneous human follicle-stimulating hormone" J Am Chem Soc. Feb. 22, 2012;134(7):3532-41.
Baldwin et al. "The importance of adjuvant formulation in the development of a tuberculosis vaccine" J Immunol. Mar. 1, 2012;188(5):2189-97.
Bar et al. "Early low-titer neutralizing antibodies impede HIV-1 replication and select for virus escape" PLoS Pathog. 2012;8(5):e1002721.
Barouch et al. "Mosaic HIV-1 vaccines expand the breadth and depth of cellular immune responses in rhesus monkeys" Nat Med. Mar. 2010;16(3):319-23.
Bonomelli et al. "The glycan shield of HIV is predominantly oligomannose independently of production system or viral clade" PLoS One. 2011;6(8):e23521.
Bonsignori et al. "Analysis of a clonal lineage of HIV-1 envelope V2/V3 conformational epitope-specific broadly neutralizing antibodies and their inferred unmutated common ancestors" J Virol. Oct. 2011;85(19):9998-10009.
Bonsignori et al. "Antibody-dependent cellular cytotoxicity-mediating antibodies from an HIV-1 vaccine efficacy trial target multiple epitopes and preferentially use the VH1 gene family" J Virol. Nov. 2012;86(21):11521-32.
Burton et al. "Broadly neutralizing antibodies present new prospects to counter highly antigenically diverse viruses" Science. Jul. 13, 2012;337(6091):183-6.
Calarses et al. "Antibody domain exchange is an immunological solution to carbohydrate cluster recognition" Science. Jun. 27, 2003;300(5628):2065-71.

(Continued)

*Primary Examiner* — Jeffrey S Parkin
(74) *Attorney, Agent, or Firm* — Baker Donelson

(57) ABSTRACT

The present invention relates, in general, to human immunodeficiency virus (HIV), and, in particular, to a vaccine for HIV-1, comprising synthetic V3 glycopeptides, and to methods of making and using same.

17 Claims, 22 Drawing Sheets

Specification includes a Sequence Listing.

(56) References Cited

OTHER PUBLICATIONS

Cease et al. "Helper T-cell antigenic site identification in the acquired immunodeficiency syndrome virus gp120 envelope protein and induction of immunity in mice to the native protein using a 16-residue synthetic peptide" Proc Natl Acad Sci U S A. Jun. 1987;84(12):4249-53.
Chen et al. "A program for ligation at threonine sites: application to the controlled total synthesis of glycopeptides" Tetrahedron. Mar. 27, 2010;66(13):2277-2283.
Chen et al. "Native chemical ligation at valine: a contribution to peptide and glycopeptide synthesis" Angew Chem Int Ed Engl. 2008;47(44):8521-4.
Chuchyard et al. "A phase IIA randomized clinical trial of a multiclade HIV-1 DNA prime followed by a multiclade rAd5 HIV-1 vaccine boost in healthy adults (HVTN204)" PLoS One. 2011;6(8):e21225.
Clark et al. "Simple approach to assign disulfide connectivity using extracted ion chromatograms of electron transfer dissociation spectra" Anal Chem. Jan. 15, 2013;85(2):1192-9.
Dawson et al. "Synthesis of proteins by native chemical ligation" Science. Nov. 4, 1994;266(5186):776-9.
Dirksen et al. "Nucleophilic catalysis of oxime ligation" Angew Chem Int Ed Engl. Nov. 20, 2006;45(45):7581-4.
Dirksen et al. "Rapid oxime and hydrazone ligations with aromatic aldehydes for biomolecular labeling" Bioconjug Chem. Dec. 2008;19(12):2543-8.
Dong et al."Engineering of therapeutic polypeptides through chemical synthesis: early lessons from human parathyroid hormone and analogues" J Am Chem Soc. Sep. 12, 2012;134(36):15122-9.
Doores et al. "Envelope glycans of immunodeficiency virions are almost entirely oligomannose antigens" Proc Natl Acad Sci U S A. Aug. 3, 2010;107(31):13800-5.
European Supplementary Search Report, submitted Nov. 4, 2016.
Gamblin et al. "Glycoprotein synthesis: an update" Chem Rev. Jan. 2009;109(1):131-63. doi: 10.1021/cr078291i.
Geng et al. "In pursuit of carbohydrate-based HIV vaccines, part 2: The total synthesis of high-mannose-type gp120 fragments—evaluation of strategies directed to maximal convergence" Angew Chem Int Ed Engl. May 3, 2004;43(19):2562-5.
Gilewski et al. "Immunization of metastatic breast cancer patients with a fully synthetic globo H conjugate: a phase I trial" Proc Natl Acad Sci U S A. Mar. 13, 2001;98(6):3270-5.
Go et al. "Characterization of glycosylation profiles of HIV-1 transmitted/founder envelopes by mass spectrometry" J Virol. Aug. 2011;85(16):8270-84.
Gray et al. "The neutralization breadth of HIV-1 develops incrementally over four years and is associated with CD4+ T cell decline and high viral load during acute infection" J Virol. May 2011;85(10):4828-40.
Haynes et al. "B-cell-lineage immunogen design in vaccine development with HIV-1 as a case study" Nat Biotechnol. May 7, 2012;30(5):423-33.
Haynes et al. "Immune-correlates analysis of an HIV-1 vaccine efficacy trial" N Engl J Med. Apr. 5, 2012;366(14):1275-86.
Hessell et al. "Broadly neutralizing monoclonal antibodies 2F5 and 4E10 directed against the human immunodeficiency virus type 1 gp41 membrane-proximal external region protect against mucosal challenge by simian-human immunodeficiency virus SHIVBa-L" J Virol. Feb. 2010;84(3):1302-13.
Hessell et al. "Effective, low-titer antibody protection against low-dose repeated mucosal SHIV challenge in macaques" Nat Med. Aug. 2009;15(8):951-4.
International Preliminary Report on Patentability and Written Opinion, submitted Oct. 20, 2015.
Joyce et al. "An oligosaccharide-based HIV-1 2G12 mimotope vaccine induces carbohydrate-specific antibodies that fail to neutralize HIV-1 virions" Proc Natl Acad Sci U S A. Oct. 14, 2008;105(41):15684-9.
Kan et al. "Recent Departures in the Synthesis of Peptides and Glycopeptides" Tetrahedron. Nov. 7, 2009;65(45):9047-9065.
Krauss et al. "Fully synthetic carbohydrate Hiv antigens designed on the logic of the 2G12 antibody" J Am Chem Soc. Sep. 12, 2007;129(36):11042-4.
Kwong et al. "Human antibodies that neutralize HIV-1: identification, structures, and B cell ontogenies" Immunity. Sep. 21, 2012;37(3):412-25.
Li et al. "Chemistry as an expanding resource in protein science: fully synthetic and fully active human parathyroid hormone-related protein (1-141)" Angew Chem Int Ed Engl. Dec. 3, 2012;51(49):12263-7.
Liao et al. "A group M consensus envelope glycoprotein induces antibodies that neutralize subsets of subtype" B and C HIV-1 primary viruses Virology. Sep. 30, 2006;353(2):268-82.
Liao et al. "Co-evolution of a broadly neutralizing HIV-1 antibody and founder virus" Nature. Apr. 25, 2013;496(7446):469-76.
Malherbe et al. "Sequential immunization with a subtype B HIV-1 envelope quasispecies partially mimics the in vivo development of neutralizing antibodies" J Virol. Jun. 2011;85(11):5262-74.
Mandal et al. "In pursuit of carbohydrate-based HIV vaccines, part 1: The total synthesis of hybrid-type gp120 fragments" Angew Chem Int Ed Engl. May 3, 2004;43(19):2557-61.
Mao et al. "Subunit organization of the membrane-bound HIV-1 envelope glycoprotein trimer" Nat Struct Mol Biol. Sep. 2012;19(9):893-9.
McElrath et al. "Induction of immunity to human immunodeficiency virus type-1 by vaccination Immunity" Oct. 29, 2010;33(4):542-54.
McLellan et al. "Structure of HIV-1 gp120 V1/V2 domain with broadly neutralizing antibody PG9" Nature. Nov. 23, 2011;480(7377):336-43.
Meyer et al. "Conformation of Glycopeptides and Glycoproteins" Glycopeptides and Glycoproteins. Oct. 28, 2006; 267:187-251.
Miller et al. "Toward fully synthetic N-linked glycoproteins" Angew Chem Int Ed Engl. Jan. 27, 2003;42(4):431-4.
Moldt et al. "Highly potent HIV-specific antibody neutralization in vitro translates into effective protection against mucosal SHIV challenge in vivo" Proc Natl Acad Sci U S A. Nov. 13, 2012;109(46):18921-5.
Morelli et al "Carbohydrates and immunology: Synthetic oligosaccharide antigens for vaccine formulation." Eur. J. Org. Chem. 2011, 2011, 5723-5777.
Moseri et al. "An optimally constrained V3 peptide is a better immunogen than its linear homolog or HIV-1 gp120" Virology. Jun. 5, 2010;401(2):293-304.
Mouquet et al. "Complex-type N-glycan recognition by potent broadly neutralizing HIV antibodies" Proc Natl Acad Sci U S A. Nov. 20, 2012;109(47):E3268-77.
Nagorny et al. "Probing the Frontiers of Glycoprotein Synthesis: The Fully Elaborated β-subunit of the Human Follicle-Stimulating Hormone" Angew Chem Int Ed Engl. Jan. 23, 2012; 51(4): 975-979.
Nagorny et al. "Toward fully synthetic homogeneous beta-human follicle-stimulating hormone (beta-hFSH) with a biantennary N-linked dodecasaccharide. synthesis of beta-hFSH with chitobiose units at the natural linkage sites" J Am Chem Soc. Apr. 29, 2009;131(16):5792-9.
PCT international search report, submitted Sep. 2, 2014.
Pejchal et al. "A potent and broad neutralizing antibody recognizes and penetrates the HIV glycan shield" Science. Nov. 25, 2011;334(6059):1097-103.
Rerks-Ngarm et al. "Vaccination with ALVAC and AIDSVAX to prevent HIV-1 infection in Thailand" N Engl J Med. Dec. 3, 2009;361(23):2209-20.
Rolland et al. "Increased HIV-1 vaccine efficacy against viruses with genetic signatures in Env V2" Nature. Oct. 18, 2012;490(7420):417-20.
Rudd et al. "Glycosylation: heterogeneity and the 3D structure of proteins" Crit Rev Biochem Mol Biol. 1997;32(1):1-100.
Santra et al. "Mosaic vaccines elicit CD8+ T lymphocyte responses that confer enhanced immune coverage of diverse HIV strains in monkeys" Nat Med. Mar. 2010;16(3):324-8.

(56) References Cited

OTHER PUBLICATIONS

Scanlan et al. "The broadly neutralizing anti-human immunodeficiency virus type 1 antibody 2G12 recognizes a cluster of alpha1-->2 mannose residues on the outer face of gp120" J Virol. Jul. 2002;76(14):7306-21.
Seko et al. "Occurence of a sialylglycopeptide and free sialylglycans in hen's egg yolk" Biochim Biophys Acta. Apr. 17, 1997;1335(1-2):23-32.
Shang et al. "An advance in proline ligation" J Am Chem Soc. Jul. 20, 2011;133(28):10784-6.
Shang et al. "Application of the logic of cysteine-free native chemical ligation to the synthesis of Human Parathyroid Hormone (hPTH)" Proc Natl Acad Sci U S A. Apr. 12, 2011;108(15):5986-9.
Slovin et al. "Carbohydrate vaccines in cancer: immunogenicity of a fully synthetic globo H hexasaccharide conjugate in man" Proc Natl Acad Sci U S A. May 11, 1999;96(10):5710-5.
Spiro "Protein glycosylation: nature, distribution, enzymatic formation, and disease implications of glycopeptide bonds" Glycobiology. Apr. 2002;12(4):43R-56R.
Tan et al. "Insights into the finer issues of native chemical ligation: an approach to cascade ligations" Angew Chem Int Ed Engl. Dec. 3, 2010;49(49):9500-3.
Tomaras et al. "Polyclonal B cell responses to conserved neutralization epitopes in a subset of HIV-1-infected individuals" J Virol. Nov. 2011;85(21):11502-19.
Townsend et al. "Advances in praline ligation" J Am Chem Soc. Feb. 29, 2012;134(8):3912-6.
Trkola et al. "Human monoclonal antibody 2G12 defines a distinctive neutralization epitope on the gp120 glycoprotein of human immunodeficiency virus type 1" J Virol. Feb. 1996;70(2):1100-8.
Van De Vijver et al. "Incorporation of disulfide containing protein modules into multivalent antigenic conjugates: generation of antibodies against the thrombin-sensitive region of murine protein" J Am Chem Soc. Nov. 28, 2012;134(47):19318-21.
Verkoczy et al. "Role of immune mechanisms in induction of HIV-1 broadly neutralizing antibodies" Curr Opin Immunol. Jun. 2011;23(3):383-90.
Walczak et al. "Solving the convergence problem in the synthesis of triantennary N-glycan relevant to prostate-specific membrane antigen (PSMA)" J Am Chem Soc. Oct. 3, 2012;134(39):16430-3.
Walker et al. "Broad and potent neutralizing antibodies from an African donor reveal a new HIV-1 vaccine target" Science. Oct. 9, 2009;326(5950):285-9.
Walker et al. "Broad neutralization coverage of HIV by multiple highly potent antibodies" Nature. Sep. 22, 2011;477(7365):466-70.
Wang et al. "An advance in the chemical synthesis of homogeneous N-linked glycopolypeptides by convergent aspartylation" Angew Chem Int Ed Engl. Nov. 12, 2012;51(46):11571-5.
Wang et al. "At last: erythropoietin as a single glycoform" Angew Chem Int Ed Engl. Nov. 12, 2012;51(46):11576-84. doi: 10.1002/anie.201206090.
Wang et al. "Emerging technologies for making glycan-defined glycoproteins" ACS Chem Biol. Jan. 20, 2012;7(1):110-22.
Wang et al. "Total synthesis of the 2,6-sialylated immunoglobulin G glycopeptide fragment in homogeneous form" J Am Chem Soc. Nov. 25, 2009;131(46):16669-71.
Warren et al. "Toward fully synthetic glycoproteins by ultimately convergent routes: a solution to a long-standing problem" J Am Chem Soc. Jun. 2, 2004;126(21):6576-8.
Wilson et al. "Promising agents at the interface of biology and oncology derived through chemical synthesis" Pure and Applied Chemistry. vol. 79, Issue 12, pp. 2189-2216.
Yang et al. "Expression, glycoform characterization, and antibody-binding of HIV-1 V3 glycopeptide domain fused with human IgG1-Fc" Bioconjugate Chemistry, May 19, 2010; 21(5): 875-883.
Yu et al. "Generation of mucosal anti-human immunodeficiency virus type 1 T-cell responses by recombinant *Mycobacterium smegmatis*" Clin Vaccine Immunol. Nov. 2006;13(11):1204-11.
Yu et al. "Glycoform and net charge heterogeneity in gp120 immunogens used in HIV vaccine trials" PLoS One. 2012;7(8):e43903.
Yu et al. "Recombinant *Mycobacterium bovis bacillus* Calmette-Guerin elicits human immunodeficiency virus type 1 envelope-specific T lymphocytes at mucosal sites" Clin Vaccine Immunol. Jul. 2007;14(7):886-93.
Zhu et al. "From synthesis to biologics: preclinical data on a chemistry derived anticancer vaccine" J Am Chem Soc. Jul. 8, 2009;131(26):9298-303.
Zhu et al. "Synthetic carbohydrate-based anticancer vaccines: the Memorial Sloan-Kettering experience" Expert Rev Vaccines. Oct. 2009;8(10):1399-413.
NCBI PDB Accession No. 3TYG_A.
Accession No. KC247375-KC247667.
Accession No. KC575845-KC576303.
Montefiori, et al. "Magnitude and Breadth of the Neutralizing Antibody Response in the RV144 and Vax003 HIV-1 Vaccine Efficacy Trials" JID Aug. 1, 2012, 206: 431-441.
Alam et al., "Recognition of synthetic glycopeptides by HIV-1 broadly neutralizing antibodies and their unmutated ancestors", Proc Natl Acad Sci U S A. Nov. 5, 2013;110(45):18214-9. doi: 10.1073/pnas.1317855110. Epub Oct. 21, 2013.
Allen et al. "A second generation synthesis of the MBr1 (globo-H) breast tumor antigen: new application of the n-pentenyl glycoside method for achieving complex carbohydrate protein linkages" Chemistry. Apr. 14, 2000;6(8):1366-75. (Abstract Only).
Anisfeld et al. "A convergent approach to the chemical synthesis of asparagine-linked glycopeptides" J. Org. Chem., 1990, 55 (21), pp. 5560-5562.
Aussedat et al. "Chemical synthesis of highly congested gp120 V1V2 N-glycopeptide antigens for potential HIV-1-directed vaccines", J Am Chem Soc. Sep. 4, 2013;135(35):13113-20. Epub Aug. 22, 2013.
Bilodeau et al. "Total Synthesis of a Human Breast Tumor Associated Antigen" J. Am. Chem. Soc., 1995, 117 (29), pp. 7840-7841.
Broker, et al."Chemistry of a new investigational quadrivalent meningococcal conjugate vaccine that is immunogenic at all ages" Vaccine. Sep. 18, 2009;27(41):5574-80.
Cohen-Anisfeld et al "A practical, convergent method for glycopeptide synthesis" J. Am. Chem. Soc., 1993, 115(23), pp. 10531-10537.
Davis. "Synthesis of glycoproteins" Chem Rev. Feb. 2002;102(2):579-602.
Haack et al. "Serine derived oxazolidines as secondary structure disrupting, solubilizing building blocks in peptide synthesis" Tetrahedron Letters. Mar. 17, 1992; 33(12):1589-1592.
Hart et al. "Synthetic peptides containing T and B cell epitopes from human immunodeficiency virus envelope gp120 induce anti-HIV proliferative responses and high titers of neutralizing antibodies in rhesus monkeys" J Immunol. Oct. 15, 1990;145(8):2677-85.
Imperiali et al. "Effect of N-linked glycosylation on glycopeptide and glycoprotein structure" Curr Opin Chem Biol. Dec. 1999;3(6):643-9.
Kajihara et al. "Prompt chemoenzymatic synthesis of diverse complex-type oligosaccharides and its application to the solid-phase synthesis of a glycopeptide with Asn-linked sialyl-undeca- and asialo-nonasaccharides" Chemistry. Feb. 20, 2004;10(4):971-85.
Knuf et al. "Comparative effects of carrier proteins on vaccine-induced immune response" Vaccine. Jul. 12, 2011;29(31):4881-90.
Kornfeld et al. Assembly of asparagine-linked oligosaccharides. Annu Rev Biochem. 1985;54:631-64.
Li et al. "Chemoenzymatic synthesis of HIV-1 V3 glycopeptides carrying two N-glycans and effects of glycosylation on the peptide domain" J Org Chem. Nov. 25, 2005;70(24):9990-6.
Likhosherstov et al. "A new simple synthesis of amino sugar beta-D-glycosylamines" Carbohydrate Res. 1986, 146, C1-C5.
Muir. "Semisynthesis of proteins by expressed protein ligation" Annu Rev Biochem. 2003;72:249-89.
Murakami, et al. "Chemical synthesis of an erythropoietin glycoform containing a complex-type disialyloligosaccharide" Angew Chem Int Ed Engl. Apr. 10, 2012;51(15):3567-72.
Park et al "Total Synthesis and Proof of Structure of a Human Breast Tumor (Globo-H) Antigen" J. Am. Chem. Soc., 1996; 118 (46):11488-11500.

(56) References Cited

OTHER PUBLICATIONS

Ragupathi et al. "A Fully Synthetic Globo H Carbohydrate Vaccine Induces a Focused Humoral Response in Prostate Cancer Patients: A Proof of Principle" Angewandte Chemie, Feb. 15, 1999; 38(4):563-566.

Ragupathi et al. "Immunization of Mice with a Fully Synthetic Globo H Antigen Results in Antibodies against Human Cancer Cells: A Combined Chemical—Immunological Approach to the Fashioning of an Anticancer Vaccine" Angewandte Chemie, 1997; 36(1-2):125-128.

Ragupathi et al. "Preparation and evaluation of unimolecular pentavalent and hexavalent antigenic constructs targeting prostate and breast cancer: a synthetic route to anticancer vaccine candidates" J Am Chem Soc. Mar. 1, 2006;128(8):2715-25.

Stephanopoulos et al. "Choosing an effective protein bioconjugation strategy" Nat Chem Biol. Nov. 15, 2011;7(12):876-84.

Wan et al. "Free-radical-based, specific desulfurization of cysteine: a powerful advance in the synthesis of polypeptides and glycopolypeptides" Angew Chem Int Ed Engl. 2007;46(48):9248-52.

Wang. "Toward oligosaccharide- and glycopeptide-based HIV vaccines" Curr Opin Drug Discov Devel. Mar. 2006;9(2):194-206.

Wilson et al. "Small molecule natural products in the discovery of therapeutic agents: the synthesis connection" J Org Chem. Oct. 27, 2006;71(22):8329-51.

Yan et al. "Synthesis of peptides and proteins without cysteine residues by native chemical ligation combined with desulfurization" J Am Chem Soc. Jan. 31, 2001;123(4):526-33.

\* cited by examiner

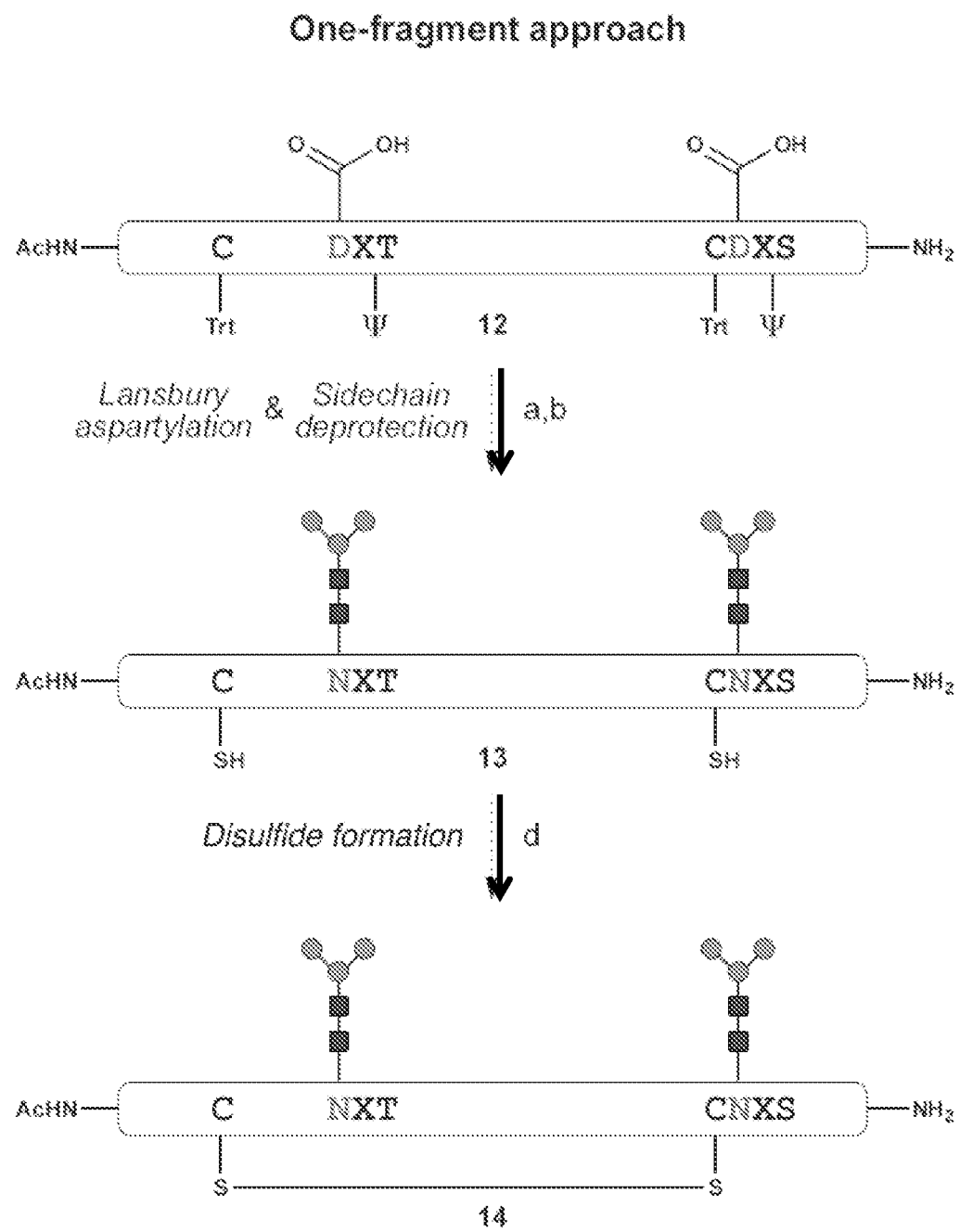
Figure 3A (One-fragment approach)

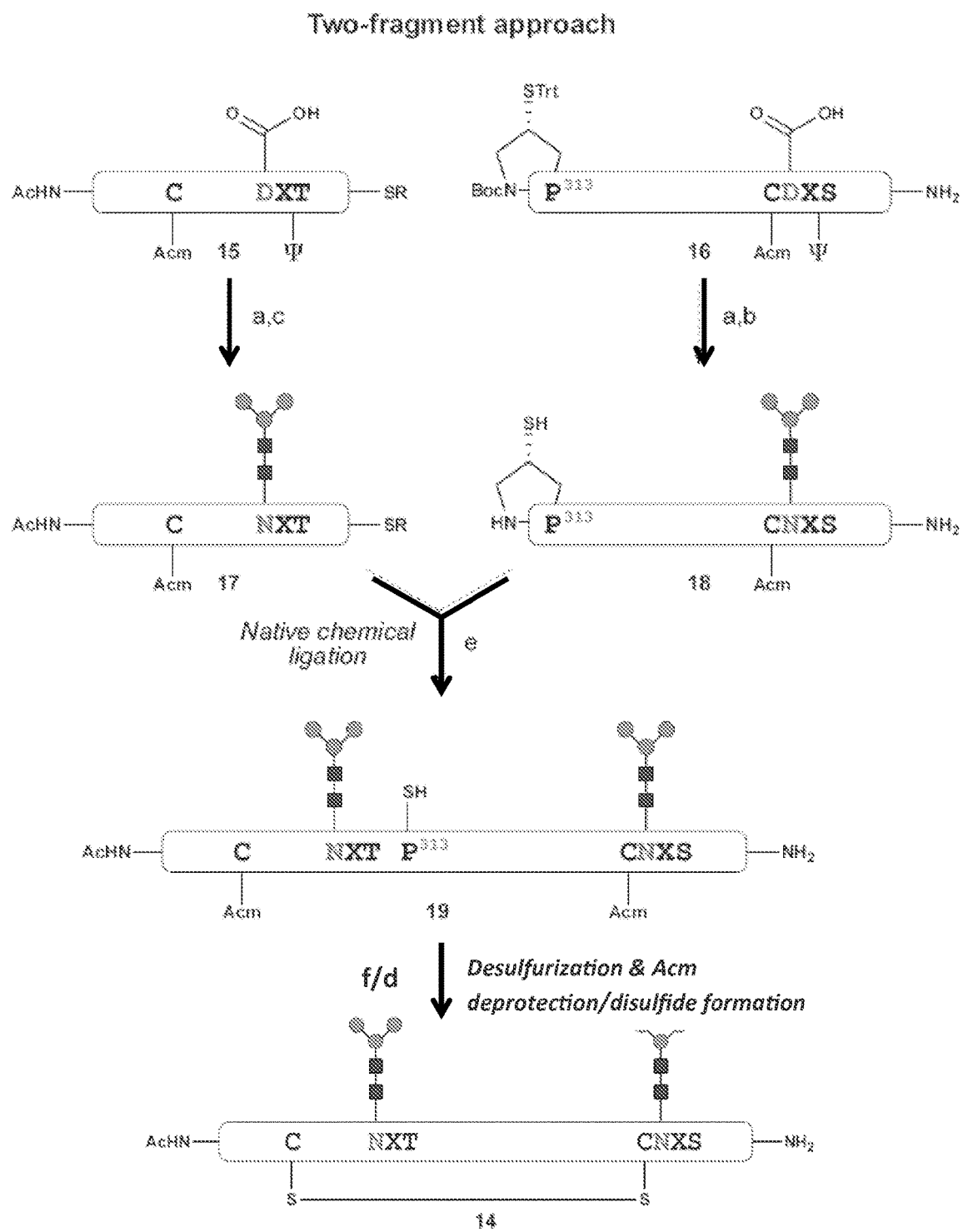
Figure 3B (Two-fragment approach)

High mannose
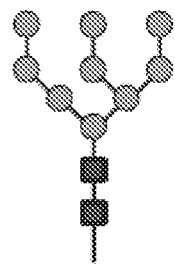
Man₉
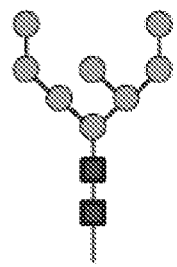
Man₈
Complex
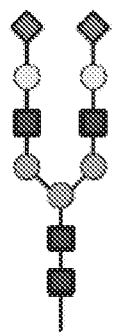
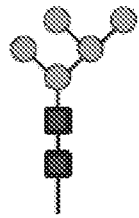
Man₅
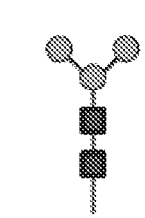
Man₃
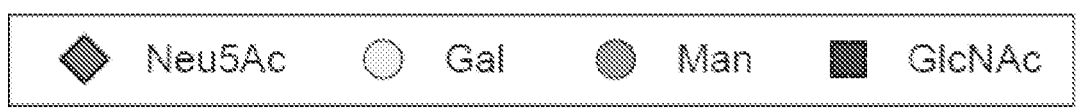
Figure 5A

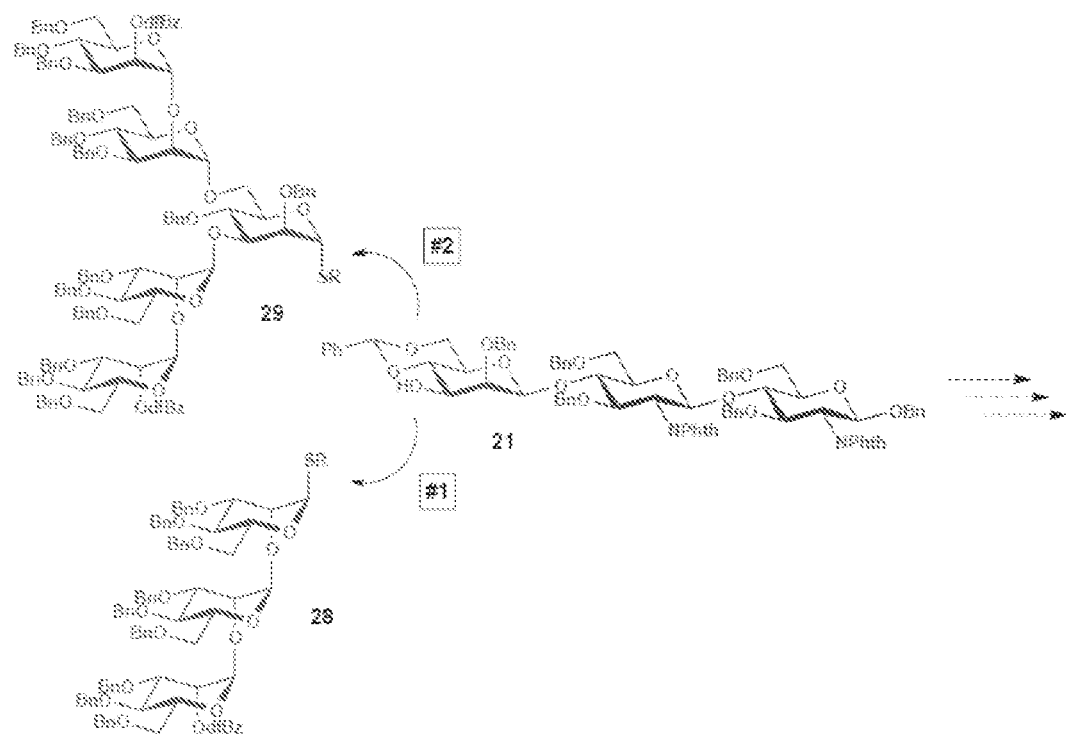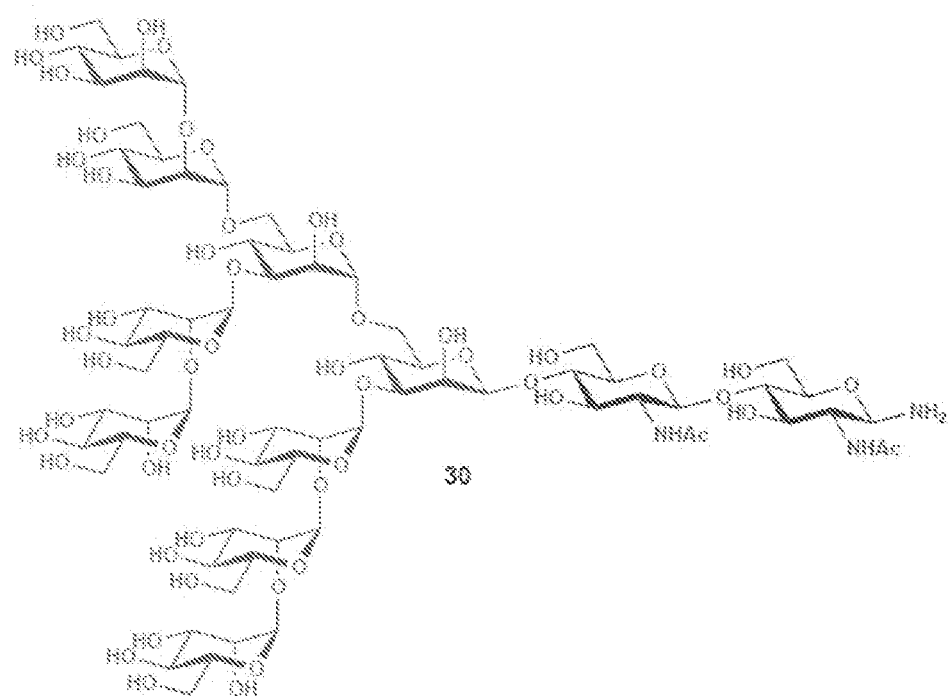
Figure 7

US 10,286,057 B2

CYCLIC HIV-1 ENV V3 GLYCOPEPTIDE IMMUNOGENS

This application claims the benefit of U.S. Provisional Application Ser. No. 61/811,992 filed Apr. 15, 2013 the entire content of which application is hereby incorporated by reference.

SEQUENCE LISTING

The instant application contains a Sequence Listing which has been submitted electronically in ASCII format and is hereby incorporated by reference in its entirety. Said ASCII copy, created on Nov. 17, 2015, is named 2933311-013.US2_SL.txt and is 5,937 bytes in size.

This invention was made with government support under Grant No. UM1 AI100645 awarded by the National Institutes of Health. The government has certain rights in the invention.

TECHNICAL FIELD

The present invention relates, in general, to human immunodeficiency virus (HIV), and, in particular, to a vaccine for HIV-1 and to methods of making and using same.

BACKGROUND

Development of an effective vaccine for prevention of HIV-1 infection is a global priority. While the RV144 trial using ALVAC prime, AIDSVAX B/E boost resulted in an estimated 31% vaccine efficacy, the protection induced was neither sufficiently robust for deployment, nor of sufficient durability for sustained vaccine efficacy.[8] In the RV144 trial, antibodies capable of neutralizing transmitted/founder viruses were not induced; rather the hypothesis is that antibodies targeted to the Env V2 region protected by effector mechanisms other than virus neutralization, such as antibody-dependent cellular cytotoxicity (ADCC).[9a, 10, 11]

By contrast, antibodies capable of broadly neutralizing HIV-1 strains (BnAbs) have been isolated from HIV-1 chronically-infected subjects.[1] These antibodies are targeted to four general HIV-1 envelope targets: the gp41 membrane proximal external region (MPER), and on gp120, the CD4 binding site (CD4bs), the V1V2 glycan site, and several gp120 glycan sites.[2] However, only approximately 20% of infected subjects produce BnAbs, and then, only after years of infection.[12] When infused into rhesus macaques, BnAbs can protect against infection with chimeric simian-human immunodeficiency viruses (SHIVs).[13] However, BnAbs have not been successfully induced by vaccine constructs thus far.

A recently described set of epitopes to which potent BnAbs do bind are defined by the PGT121, 125 and 128 mAbs isolated from HIV-1 chronically infected subjects.[4,6] These antibodies are able to recognize a peptide-glycan epitope around the base of the gp120 V3 loop and includes N-linked glycans at amino acids 301 and 332.[6] These antibodies are the most potent BnAbs isolated to date, and are able to protect rhesus macaques from SHIV challenge at extremely low plasma levels.[14] Thus, induction of antibodies with specificities like these PGT antibodies is a key goal of HIV-1 vaccine development.

Many reasons can be envisioned to account for the difficulties encountered in inducing such BnAbs. The heavily glycosylated envelope could well obstruct antibody access to BnAb sites.[2] The dominance of non-neutralizing epitope responses compared to the non-dominance of BnAb epitope responses might result in an inability of the B cell response to BnAb epitopes to either be induced or to be sustained.[1] To date, all BnAbs that have been isolated from chronically infected subjects exhibit unusual traits including high levels of somatic mutations, long heavy chain third complementarity determining regions (HCDR3s), and polyreactivity for non-HIV-1 antigens—all traits of antibodies that are potentially susceptible to control by host tolerance mechanisms.[1,7]

Thus, it seems likely from the unusual nature of BnAbs that unusual strategies will be required for their induction. Several discovery platforms have been proposed, including definition of BnAb epitope structures on the surface of native Env trimers,[2] identification of Env constructs that bind mature BnAbs and their ancestor antibodies avidly,[1b] and immunization with sequential Env constructs isolated during the course of HIV-1 infection.[15] However, none of these modes of operation take into account the heterogeneity of forms of recombinant Envs,[16] and none prevent dominant, non-neutralizing antibody epitopes from inducing antibodies that out-compete BnAb-producing B cells targeted at sub-dominant Env BnAb epitopes. The ability to synthesize completely homogeneous glycopeptides that mimic the antigenic nature of native envelope proteins would facilitate the generation of constructs that can be configured to express primarily or only BnAb sub-dominant epitopes, thus limiting the likelihood of a dominant non-neutralizing response to be induced.

New chemical methods have been developed to produce totally synthetic glycosylated erythropoietin.[17] These methods can be applied to the HIV/AIDS vaccine production. Attention has recently focused on the preparation, by chemical synthesis, of the V1V2 peptide-glycan epitope defined by BnAbs PG9 and CH01 lineages. In the context of these studies, a potential immunogen has been discovered that is capable of binding not only mature V1V2 BnAbs but also (in nM affinities) to their unmutated common ancestors (UCAs) (i.e., naïve B cell receptors (BCR)) of the V1V2 BnAb lineages. Previously, few Env constructs had been found that bind to the CH01 lineage UCA[18] and none had been found that bind to the PG9 UCA.[10]

The present invention results, at least in part, from studies involving the design and chemical synthesis of immunogens that elicit neutralizing antibodies directed toward the V3 glycan epitope that is recognized by mAb PGT128.

SUMMARY OF THE INVENTION

The present invention relates generally to HIV. More specifically, the invention relates to a vaccine for HIV-1 and to methods of making and using same.

In certain aspects, the invention provides a synthetic peptide comprising sequence SEQ ID NO: 2, 4, 6, 7, 8 or 9, and wherein the peptide is cyclic via endogenous cysteines. In certain embodiments, the peptide is glycosylated at positions Asn301 and/or Asn 332. In certain embodiments the peptide comprises a tag. In certain embodiments, the tag is biotin. In certain embodiments, there is a linker between the tag and the peptide, which linker could improve the peptide presentation when the peptide is immobilized via the linker. In certain aspects, the invention provides a synthetic peptide wherein the peptide is of SEQ ID NO: 2, 4, 6, 7, 8 or 9, and wherein the peptide is glycosylated at positions Asn301 and Asn 332. In certain aspects, the invention provides a synthetic glycopeptide of the structure in FIG. 12 (peptide of SEQ ID NO: 8 glycosylated at positions Asn301 and Asn 332 with Man₉GlcNAc₂, wherein the peptide is cyclic via endogenous cysteines. In certain embodiments, the peptide is glycosylated with oilgomannose. In certain embodiments, the peptide has Man₉GlcNAc₂ glycans at positions Asn301 and Asn 332. In certain embodiments, the peptides are purified.

In certain aspects, the invention provides a composition comprising a plurality of synthetic peptides of a given sequence as described herein, wherein the composition comprises purified homogenously glycosylated peptides. In certain embodiments, the glycosylation pattern is homogenous on all peptides of SEQ ID NO: 2, 4, 6, 7, 8 or 9 in the composition. In certain embodiments, the peptide is cyclic via endogenous cysteines. In certain embodiments, the compositions further comprise an adjuvant.

In certain aspects, the invention provides a method of inducing antibodies against HIV-1 in a subject, the method comprising administering to the subject any one of the inventive peptides or compositions comprising the same in an amount sufficient to induce the anti-HIV-1 antibodies.

In certain embodiments of the methods, the compositions used in the methods comprise anyone of the glycopeptides described herein. In certain embodiments of the methods, the compositions used in the methods comprise glycopeptide of the structure in FIG. 12 (peptide of SEQ ID NO: 8 glycosylated at positions Asn301 and Asn 332 with Man₉GlcNAc₂, wherein the peptide is cyclic via endogenous cysteines. In certain embodiments, the said subject is a human.

In certain aspects, the invention provides a method of determining whether a subject has antibody responses to a V3 glycoprotein comprising obtaining a sample from a subject and determining binding of the sample to V3 glycopeptide and/or the glycan (e.g. free glycan or derivitazized glycan (biotinylated or amine conjugated) and the aglycone V3 peptide, wherein a sample (e.g. plasma, serum, blood, or any other suitable biological sample) which includes components (e.g antibodies) which bind preferentially to the V3 glycopeptide and/or the glycan (e.g. free glycan or derivitazized glycan (biotinylated or amine conjugated) but do not bind to the aglycone V3 peptide, is indicative of the subject having V3 glycopeptide antibodies. Various assays and methods are known in the art to determine if the antibodies induced by a V3 glycopeptide are neutralizing antibodies, and the breadth of neutralization. In certain embodiments, the individual is infected with HIV-1. In certain embodiments, the individual is immunized with a composition comprising an HIV-1 immunogen, including but not limited to any one of the synthetic V3 glycopeptides described herein. Thus in certain embodiments, the invention provides methods to determine whether a V3 glycopeptide is immunogenic in a vaccination regimen.

In certain aspects, the invention provides a method for synthesis of a V3 glycopeptide for example according to the scheme in Example 5.

An isolated antibody which binds to the peptide of claim 1 or the dimer of claim 5, wherein the antibody does not bind to the non-glycosylated peptide of SEQ ID NO: 9 (Aglycone V1V2 peptide of SEQ ID NO: 9).

In certain aspects the invention provides a V3 glycopeptide immunogen as shown in FIG. 2, FIG. 11. In certain aspects, the invention provides a method of inducing the production of broadly neutralizing antibodies in a subject comprising administering to the subject an amount of any one of the immunogenic peptides and/or compositions described here in an amount sufficient to effect said induction.

Objects and advantages of the present invention will be clear from the description that follows.

BRIEF DESCRIPTION OF THE DRAWINGS

(FIG. 1A) Structure of the four antigens, derived from the V1V2 region of gp120, bearing two N-linked Man₅GlcNAc₂, Man₃GlcNAc₂, or GlcNAc₂ oligosaccharides at N160 and N156, or zero glycans ("aglycone") (V1V2 sequence (SEQ ID NO: 9) based on the AE.CM244 strain, displayed with HXB2 numbering). Surface plasmon reasonance (SPR) analysis of the interaction of V1V2 Man₅GlcNAc₂ (green), Man₃GlcNAc₂ (red), GlcNAc2 (blue), or aglycone (magenta) antigens with BnAbs PG9 (FIG. 1B), CH01 (FIG. 1C), or their respective umutated common ancestor (UCA) antibodies, PG9 UCA (FIG. 1D), and CH01-04 UCA (FIG. 1E). Concentration of antigens was 200 µg/ml for FIGS. 1A and 1B, and 100 µg/ml for FIGS. 1D and 1E, RU=response units FIGS. 2A-2C. Design gp120 V3 region BnAb epitope mimics.

FIG. 3. General strategy for synthesizing gp120 V3 loop-based glycopeptides by either one- or two-fragment approaches. Reagents and conditions: (a) Man₃GlcNAc₂—NH₂, PyAOP, DIEA, DMSO; (b) Cocktail R=90:5:3:2 TFA/thioanisole/ethanedithiol/anisole; (c) Cocktail B=88:5:5:2 TFA/phenol/water/trisopropysilane; (d) I₂, AcOH, H₂O; (e) Gnd HCl, MPAA, TCEP, phosphate buffer, pH 7.2; (f) Gnd HCL, TCEP, VA-044, t-BuSH, phosphate buffer, pH 7.2, 37° C. Acm=acetamidomethyl, Boc=tert-butoxycarbonyl, DIEA=N,N-diisopropylethylamine, DMSO=dimethylsulfoxide, Gnd=guanidine, MPAA=4-mercaptophenylacetic acid, ψ=pseudoproline, PyAOP=(7-azabenzotriazol-1-yloxy)tripyrrolidinophosphonium hexafluorophosphate, R=alkyl or aryl, TFA=trifluoroacetic acid, TCEP=tris(2-carboxyethyl)phosphine, Trt=trityl, VA-044=2,2'-azobis[2-(2-imidazolin-2-yl)propane]dihydrochloride, X=any amino acid except proline.

FIGS. 5A and 5B. V3 region glycoforms. (FIG. 5A) Consortium for Functional Glycomics (CFG) representations of high mannose and complex-type oligosaccharides. (FIG. 5B) Candidate glycopeptides based on the B.JRFL mini-V3 peptide backbone (SEQ ID NOS 2 & 8). Sites of N-glycosylation are colored red. Gal=galactose, GlcNac=N-acetylglucosamine, Man=mannose, Neu5Ac=N-acetylneuraminic acid.

FIG. 7. Outline for synthesis of $Man_3GlcNAc_2$ 30. Starting with trisaccharide core 21, $Man_9GlcNAc_2$ can be obtained as shown by first introducing trisaccharide donor 28 at the 3-OH, then unmasking the 6-OH for union with pentasaccharide donor 29, followed by global deprotection.

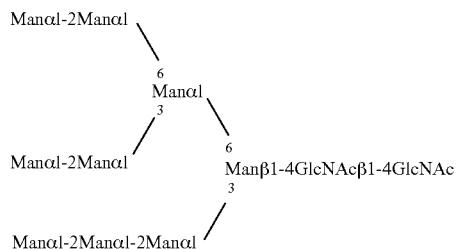

Figure 14A:
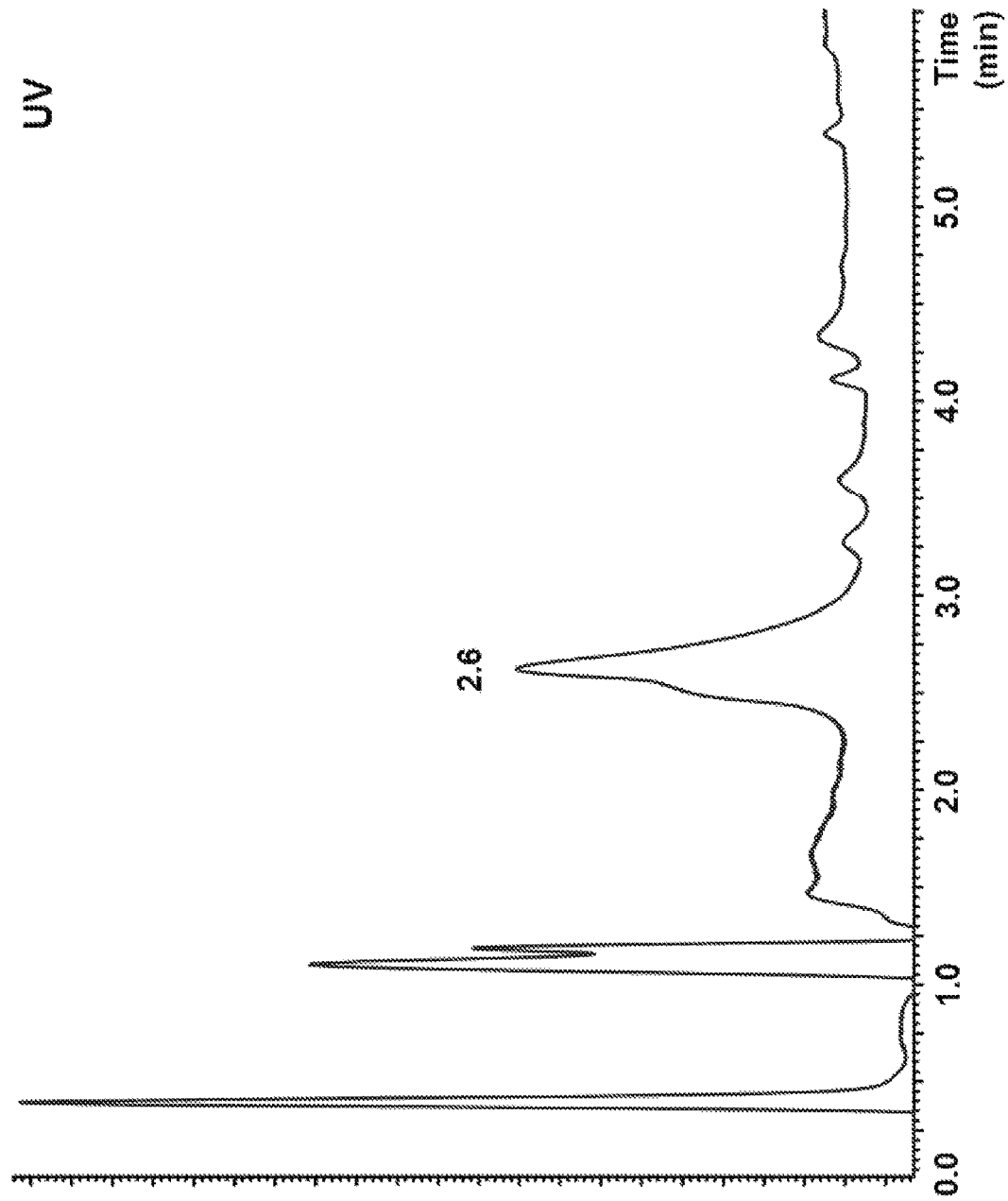
Figure 14B:
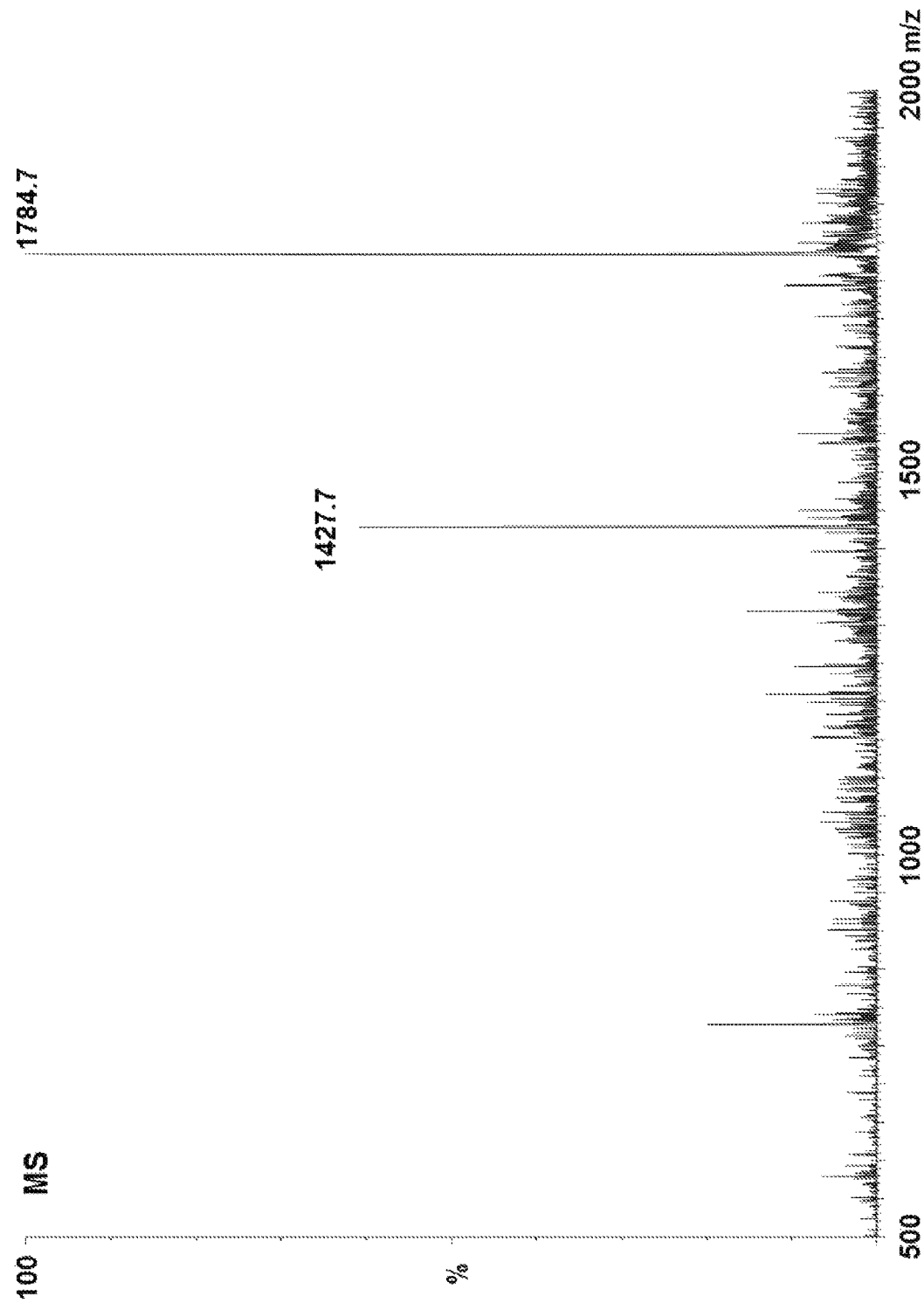

FIGS. 14A and B show analytical LCMS from the first run through the synthesis. FIG. 14 shows the $Man_9V3$ glycopeptide UV profile and FIG. 14B shows $Man_9V3$ glycopeptide mass spectrometry profile. This is an analytical run so the quality will be improved. The product runs at a retention time of 2.6 min and the mass spectrum shows [M+4H]4+ (1784.7) and [M+5H]5+ (1427.7) peaks. The sample was run on a Waters Acquity UPLC instrument, C8 column, 10-60% acetonitrile/water over 5 min at a flow rate of 0.3 mL/min. The shoulder that is evident in the UV trace is from one of the glycopeptide fragments that was difficult to separate away from the final product.

DETAILED DESCRIPTION OF THE INVENTION

New targets for HIV-1 vaccine development have been revealed by studies of recently identified broadly neutralizing antibodies (BnAbs).[1,2] Two classes of antibodies with potent neutralizing activities recognize glycan-dependent epitopes on the viral envelope spike (Env), specifically on the variable loop domains of gp120. The V1/V2-directed conformational BnAbs, typified by PG9 and PG16,[3] compose one group, characterized by a dependence on N160 glycosylation. The second group, which includes PGT121 and PGT128, binds the V3 region and requires an N-glycan at N332.[4] Crystallographic studies[5,6] indicate that these two classes of BnAbs share a common mode of epitope recognition characterized by engagement of two N-glycans and a β-strand, and involving unusually long heavy chain third complementarity determining regions (HCDR3s). Although these interactions have been studied in great detail, the precise identity and arrangement of glycan residues that are necessary to mediate recognition remain uncertain. A more complete understanding of the involved glycan domains would facilitate structure-guided vaccine design efforts. Moreover, insights from models of B cell development suggest that the naïve ancestral B cells of potential BnAb lineages are rare due to host tolerance mechanisms that, for example, select against antibodies with long HCDR3s. [1,7] Therefore, successful induction of BnAb-like humoral responses will also likely require validation of strategies for overcoming the effects of host immunoregulation.

Described herein are both the design and chemical synthesis of immunogens that elicit neutralizing antibodies directed toward the V3 glycan epitope defined by the PGT128 BnAb class.[4,6] Minimal V3 region glycopeptides bearing two glycans of appropriate structure can mimic the antigenic nature of this epitope, and can provide an effective platform for immunogen development. This concept—based on the "two glycans and a strand" paradigm of recognition suggested by x-ray analysis[6]—has been successfully applied to the V1V2 region anti-glycan BnAb site (see Example 1). Given the likely rarity of naïve B cells relevant to BnAb ontogeny in the immune repertoire, preferred immunogens include those that exclude potentially interfering immunodominant epitopes. These immunogens can be evaluated not only based on their affinities for mature BnAbs, but also their germline precursors.

In certain embodiment, the invention provides a composition comprising any one of the inventive peptides, wherein the composition comprises purified homogenously glycosylated peptides. In certain embodiments, about 70%, 75%, 80%, 85%, 90%, 95%, 99%, or 99.9% of the peptides in the composition are homogenously glycosylated peptides. In certain embodiments, 70%, 75%, 80%, 85%, 90%, 95%, 99%, or 99.9% of the peptides in the composition are homogenously glycosylated peptides. In certain embodiments, 70%-75%, 75.1%-80%, 80.1%-85%, 85.1%-90%, 90.1%-95%, 95.1%-99%, 96%-99%, 97%-99%, 98%-99% or 99.9% of the peptides in the composition are homogenously glycosylated peptides. In certain embodiment, the glycosylation pattern is homogenous on all V3 peptides in the composition. In certain embodiment, the glycosylation pattern is substantially identical on all V3 peptides in the composition.

Various methods of determining the glycosylation pattern on a peptide are known in the art. In certain embodiments, glycosylation pattern on the peptides and % homogeneity can be determined by Liquid chromatography—mass spectrometry (LC-MS, or alternatively HPLC-MS).

As indicated in the Examples that follow, V3 glycopeptides can be synthesized with well-defined glycans at N332 and N301 using clade B and clade C sequences (derived from Envs with known antigenicity toward V3 anti-glycan BnAbs). Variations of the peptide framework include full length vs. truncated V3 loops, as well as linear vs. constrained cyclic forms (via disulfide bond formation). Antigenicity testing provides the data needed to determine the peptide design motif that is optimal for binding to HIV-1 Env anti-glycan BnAbs. Using the best peptide "scaffold", derivatives can be synthesized bearing different glycans at N332 and N301 and the determination made as to the optimal carbohydrate design for anti-glycan BnAb binding. The constructs that exhibit the highest affinity for V3-directed anti-glycan BnAbs and their UCAs can be synthesized on larger scale and subjected to trials e.g., in non-human primates—immunogenicity can be evaluated for constructs both with and without conjugation to carrier protein.

The present invention thus relates, at least in part, to immunogens that focus the immune response to the V3 glycan epitope on gp120 that lead to BnAbs and away from epitopes that lead to non-neutralizing antibodies. Central to the present design strategy is making the immunogen as minimal in size as possible so as not to introduce diverting, non-neutralizing epitopes. The sequences of preferred immunogens are described in Examples 2-4 below. Particularly preferred are the CH505 V3 glycopeptides shown FIGS. 2B and 2C. Patient CH505 was followed from the time of acute HIV-1 infection to BnAb development (the sequence of the T/F virus is provided in Liao et al (Nature Apr. 3, 2013 (doi:10.1038/nature12053)—CH505 Env sequences: Accession numbers KC247375-KC247667 and KC575845-KC576303; see also US Provisional Appln. 61/764,421, filed Feb. 13, 2013).

The immunogens can be formulated with appropriate carriers using standard techniques to yield compositions suitable for administration. The compositions can include an adjuvant, such as, for example, alum, poly IC, MF-59 or other squalene-based adjuvant, ASO1B or other liposomal based adjuvant suitable for protein immunization. Suitable vaccine strategies include, e.g., those described, for in the Examples that follow.

Nucleic acid sequences (e.g., DNA sequences) encoding the immunogens can also be administered to a subject (e.g., a human) under conditions such that the immunogen is expressed in vivo and BNAbs are produced. The DNA can be present as naked DNA with a potent promoter such as the CMV promoter as used in the pCMVr plasmid (Churchyard et al, PLoS One 6:e21225 (2011)) or as an insert in a vector, such as a rAdenoviral (Barouch, et al. Nature Med. 16: 319-23 (2010), recombinant mycobacterial (i.e., BCG or M smegmatis) (Yu et al. Clinical Vaccine Immunol. 14: 886-093 (2007); ibid 13: 1204-11 (2006), or recombinant vaccinia type of vector (Santra S. Nature Med. 16: 324-8 (2010)).

Immunogens of the invention, and nucleic acids (e.g., DNAs) encoding same, are suitable for use in generating an immune response (e.g., BNAbs) in a patient (e.g., a human patient) to HIV-1. The V3 N301, N332 peptide glycan can optimally be administered as a peptide-glycan formulated in a squalene based adjuvant such as MF59, or GLA-SE (Alving et al, Current Opinion in Immunology 24:310 (2012)). The mode of administration of the immunogen, or encoding sequence, can vary with the particular immunogen, the patient and the effect sought, similarly, the dose administered. Typically, the administration route is intramuscular or subcutaneous injection (intravenous and intraperitoneal can also be used). Additionally, the formulations can be administered via the intranasal route, or intrarectally or vaginally as a suppository-like vehicle. Optimum dosing regimens can be readily determined by one skilled in the art. The immunogens (and nucleic acids encoding same) are preferred for use prophylactically, however, their administration to infected individuals may reduce viral load.

The present invention includes the specific minimal protein immunogens disclosed herein (e.g., those in FIG. 2B) and nucleic acids comprising nucleotide sequences encoding same. The proteins can be expressed, for example, in 293T cells, 293F cells or CHO cells (Liao et al, Virology 353: 268-82 (2006)).

Certain aspects of the invention can be described in greater detail in the non-limiting Examples that follows. (See also PCT/US2012/000570 and Prov Appln. 61/806,717.) (See chemical synthesis methods described in, for example, references 17, 24, 28-31, 31b, 32-36, 36b, and 37-49 below.)

Example 1

The successful preliminary V1V2 work is based, in part, on insights from the RV144 vaccine trial, where antibodies were induced that react with the gp70-V1V2 fusion protein of the clade B case A2 Env.[9a,10] A molecular sieve analysis of viral sequences derived from vaccinated and placebo HIV-1-infected subjects demonstrated immune pressure at K169 in the V2 region, and antibodies directed to that region correlated with decreased transmission risk.[19] Monoclonal Abs have been isolated from RV144 vaccines that bind to K169 from a number of trial subjects (prototype mAb CH58) and plasma antibodies to this region were the dominant responses induced.[10]

Interestingly, V1V2 BnAbs isolated from rare HIV-1-chronically infected subjects also bind to K169 and surrounding amino acids, but also bind to high mannose glycans at N156 and N160.[3] The UCAs of V1V2 BnAbs CH01 and PG9 lineages have extremely long HCDR3s (of 24-30 aas) indicating their rarity in the germline repertoire, leading to rare sub-dominant antibody responses. It has been found that the RV144 vaccine component A244 gp120 expressed V1V2 region antigens that bound not only the mature PG9 and CH01 BnAbs, but also the CH01 UCA.[18] However, V1V2 BnAbs like CH01 and PG9 were not induced in RV144. Thus, the epitopes for CH58 ADCC-mediating V2 antibodies and V1V2 BnAbs were both expressed on the RV144 vaccine trial proteins, but the dominant response was CH58-like and not CH01/PG9-like.[10]

A possible explanation for the dominance of the CH58 epitope is that the CH58-like UCAs are all antibodies with normal length HCDR3 regions whose expression is permitted during B cell ontogeny at a sufficiently high frequency for easy clonal B cell expansion. By contrast, the remarkably long HCDR3 regions associated with the CH01/PG9 UCAs leads to their elimination more frequently in the bone marrow by tolerance deletion, resulting in a much smaller pool of naïve B cells capable of responding to the V1V2 BnAb epitope. If this interpretation is correct, then an optimal immunogen for the V1V2 BnAb peptide-glycan envelope region would be a completely homogeneous construct that selectively expresses the CH01/PG9 epitope but not the CH58 epitope, and, in addition, binds well to the CH01 and PG9 UCAs.

Figure 1A:
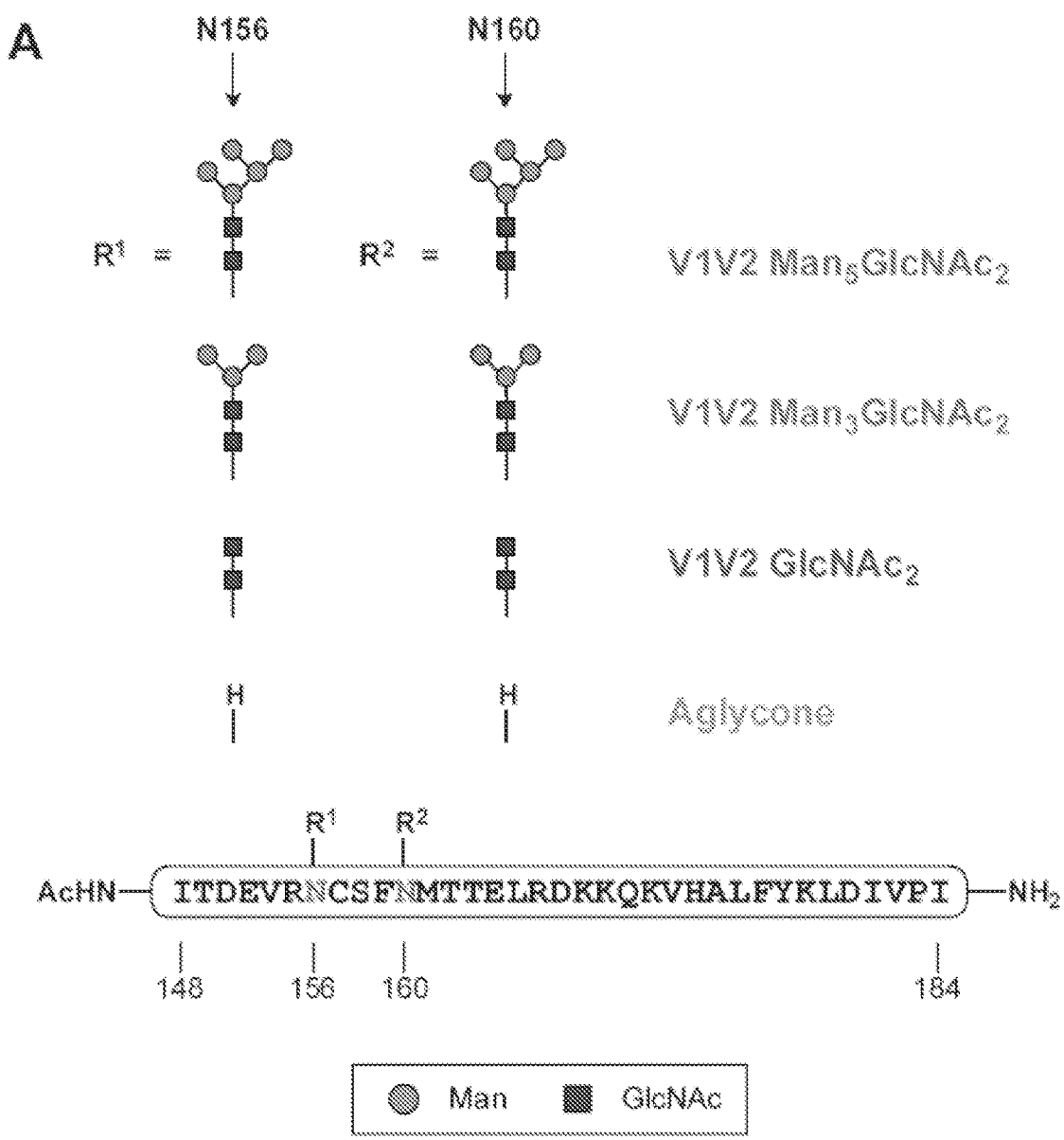
FIGS. 1A-1E. Initial evaluation of synthetic V1V2 glycopeptide constructs.
Figure 1B:
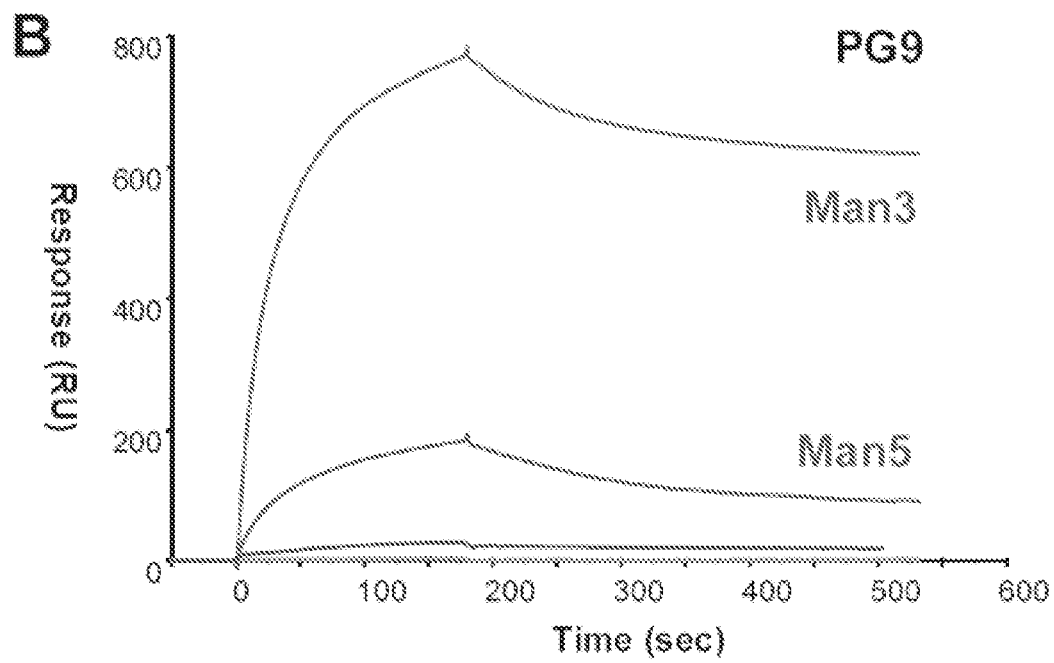
Figure 1C:
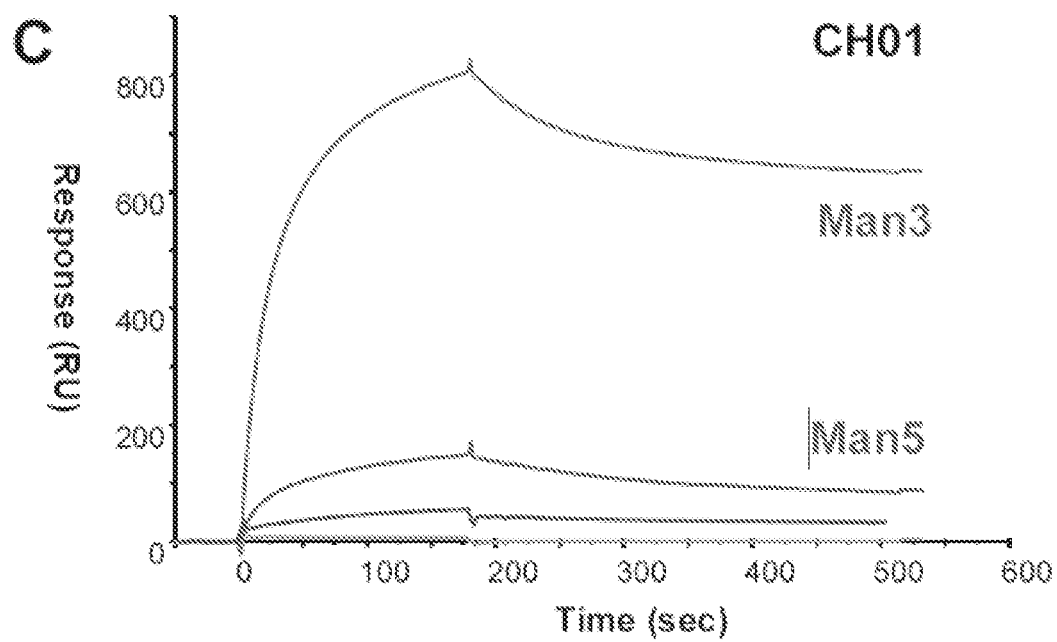

Using chemical methods (see, for example, those referenced above), a set of homogeneous V1V2 glycopeptides bearing $Man_3GlcNAc_2$, $Man_5GlcNAc_2$, and $GlcNAc_2$ N-glycans were synthesized de novo (FIG. 1A). The V1V2 sequence was derived from the A244 gp120, based on data (referred to above) demonstrating its ability to bind to the PG9 and CH01 mature BnAbs as well as the CH01 UCA. The $Man_5$ glycan was targeted based on the crystal structure of PG9 Fab with a scaffolded V1V2 domain,[5] which showed interactions with high mannose glycans at N160 and N156 and the V1V2 C β-strand. Biacore analysis of the synthetic glycopeptides indicated that both the $Man_3$ and $Man_5$, constructs bind BnAbs PG9 and CH01 (FIGS. 1B,C). These data support the concept that homogeneous glycopeptides with appropriate glycan motifs can emulate the antigenicity of full-length Envs toward V1V2 anti-glycan_BnAbs. Importantly, binding by the naked "aglycone" (FIGS. 1B,C) or the solitary protein-free $Man_3$ and $Man_5$ oligosaccharides (data not shown) was not observed. Moreover, mixtures of "aglycone" and glycan also failed to show binding, demonstrating that the peptide and carbohydrate domains are both indispensible, and that covalent linkage between them is required for recognition.

Figure 1D:
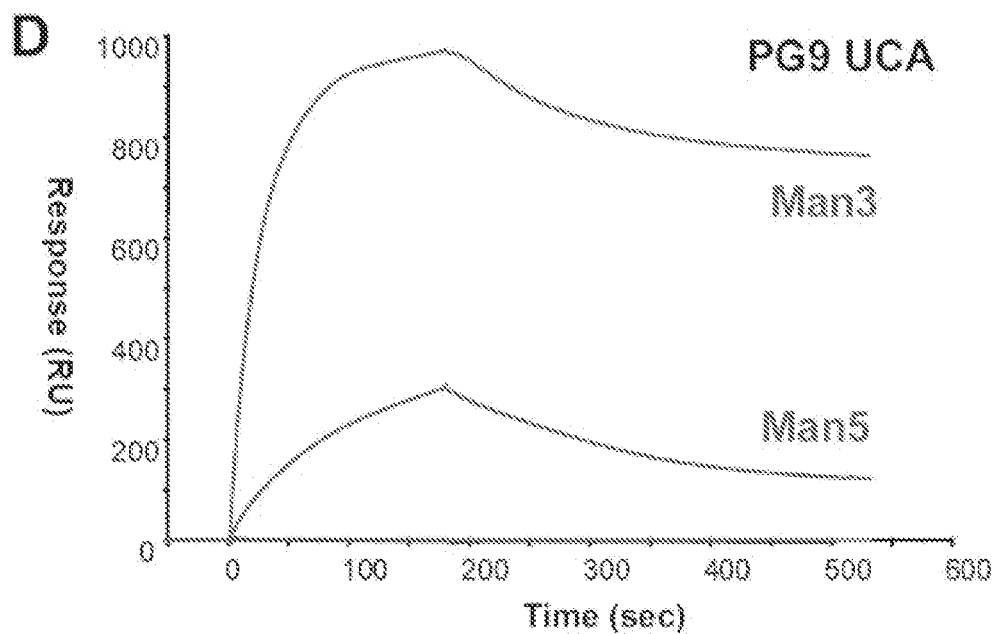
Figure 1E:
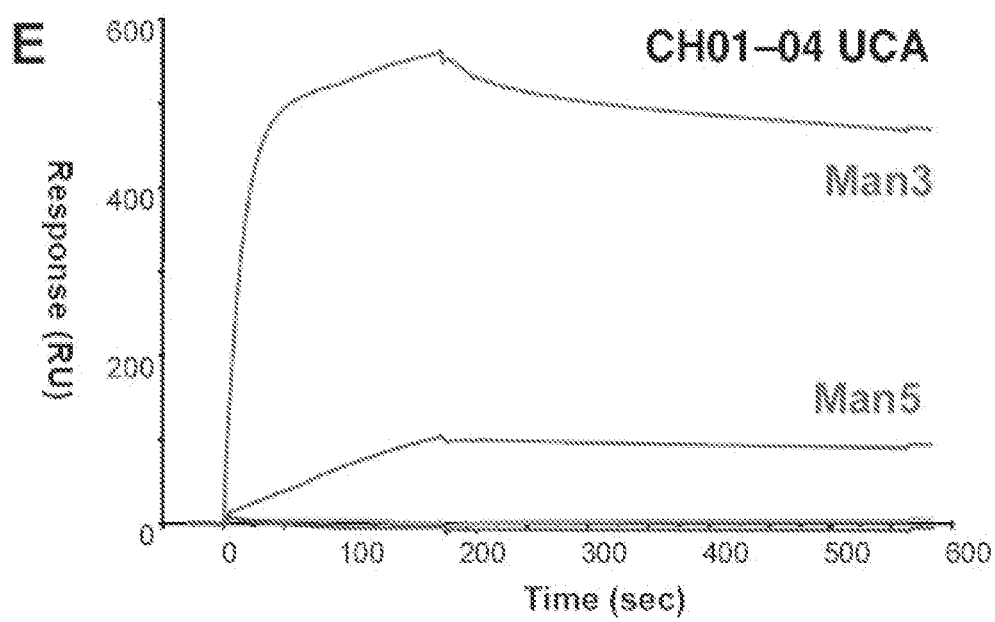

Remarkably, the $Man_3$-derivatized glycopeptide also displayed significant affinity for the UCAs of both PG9 and CH01 ($Man_5$ did as well, but to a lesser extent) (FIGS. 1D,E). This is the first antigen known to bind to the PG9 UCA. Equally important is that the RV144 mAb CH58 and its UCA exhibited only weak reactivity toward the $Man_3$ construct, and had almost no affinity for the $Man_5$ derivative (data not shown). Thus, these two V1V2 peptide-glycans have selective reactivity toward the V1V2 BnAbs, and react poorly or not at all with the CH58 mature and UCA antibodies. Therefore, these V1V2 peptide-glycan immunogens are prime candidates for selective induction of V1V2 BnAb lineages that are normally sub-dominant with infrequent UCAs.

Example 2

Described below is the synthesis of HIV-1 Env V3 glycopeptides and definition of the features of the peptide domain that support binding to V3 anti-glycan BnAbs.

Figure 2A:
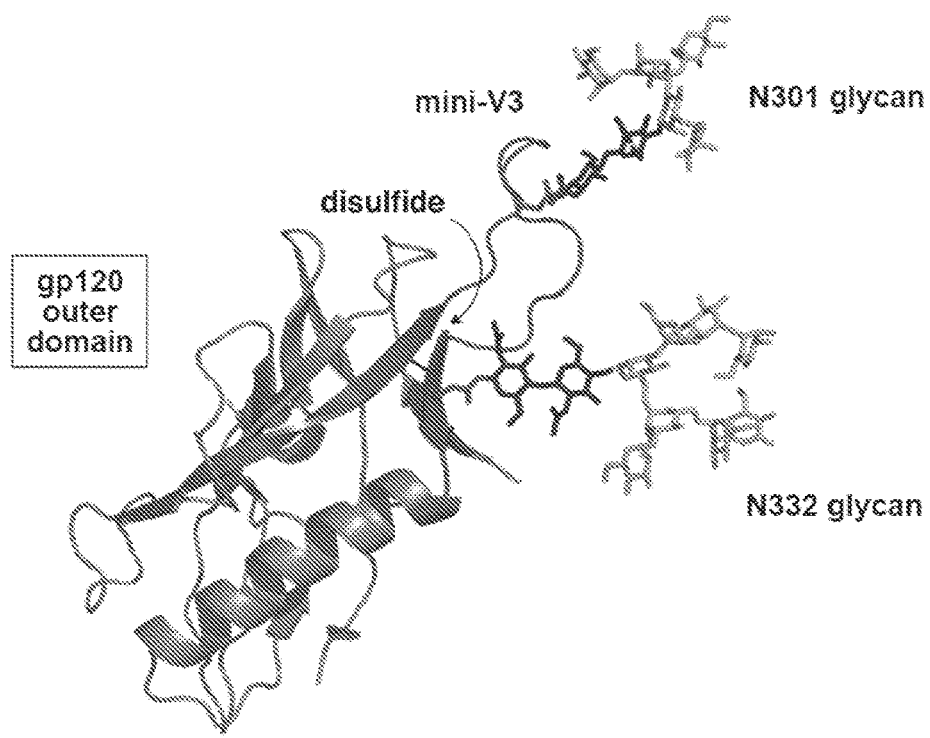
(FIG. 2A) Crystal structure of glycosylated gp120 outer domain containing a truncated V3 loop (mini-V3) (PDB ID 3TYG, with PGT128 Fab hidden). The proposed synthetic glycopeptides fragments are derived from the red-colored portion of the ribbon structure. For the glycans at N301 and N332, N-acetylglucosamine residues are colored blue, and mannose residues are colored green.

The overall design of the glycopeptide constructs is informed by the recently disclosed crystal structure of PGT128 Fab in complex with a glycosylated gp120 outer domain.[6] The bound gp120 fragment was a chimeric construct consisting of a truncated B.JRFL V3 domain ("mini-V3") grafted onto a B.HXB2 base sequence. The structure of the complex revealed that PGT128 engages two glycans (at N332 and N301) and the C-terminal V3 stem. The constructs therefore encompass these peptide and carbohydrate elements from the V3 region (colored red, blue, and green in FIG. 2A).

Clade B and clade C sequences derived from Envs that are known to bind to V3 anti-glycan BnAbs (FIG. 2B) will be used. SPR analyses indicate that the B.JRFL and C.CH505 Envs are competent to bind PGTs 121, 125, and 128, whereas B.CH040 possesses affinity for PGTs 121, 125, and 130 (Haynes, B. F., unpublished data). A V1V2 pilot study demonstrated the feasibility of using partial Env sequences with appropriate glycosylation to emulate the binding characteristics of the full-length Envs.

For the purposes of comparison, all of the constructs will be synthesized with $Man_3GlcNAc_2$ glycans at N332 and N301. The $Man_3$ sugar, unexpectedly, gave the best results in the V1V2 glycopeptide studies. Additionally, it has the virtue of being relatively accessible to chemical synthesis. Moreover, contacts between PGT128 and the interior mannose and N-acetylglucosamine residues at N332 and N301 are evident in the x-ray structure.[6] If necessary, a more highly elaborated oligomannose glycan such as $Man_9GlcNAc_2$ could certainly be synthesized and used. Interactions with the outer mannose units may also be important (especially at N332).

Figure 2B:
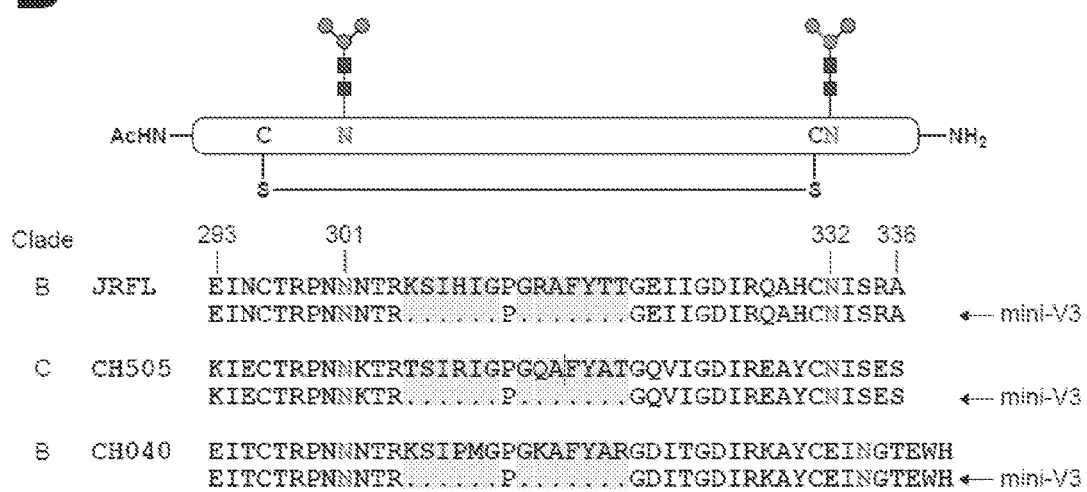
(FIGS. 2B and 2C) General structure of synthetic V3 glycopeptides, shown with clade B and C sequences containing full-length and truncated V3 loops (HXB2 numbering). Mini-V3 constructs designed after Pejchal et al[6] by deleting residues 305-320 (highlighted yellow) and retaining P313. Sites of N-glycosylation are colored red, shown with Man₃GlcNAc₂. SEQ ID NOs: 1-6 correspond to JRFL, CH505, CH040 peptides in FIG. 2B in order of appearance. SEQ ID NO: 7 corresponds to the peptide in FIG. 2C.
Figure 2C:
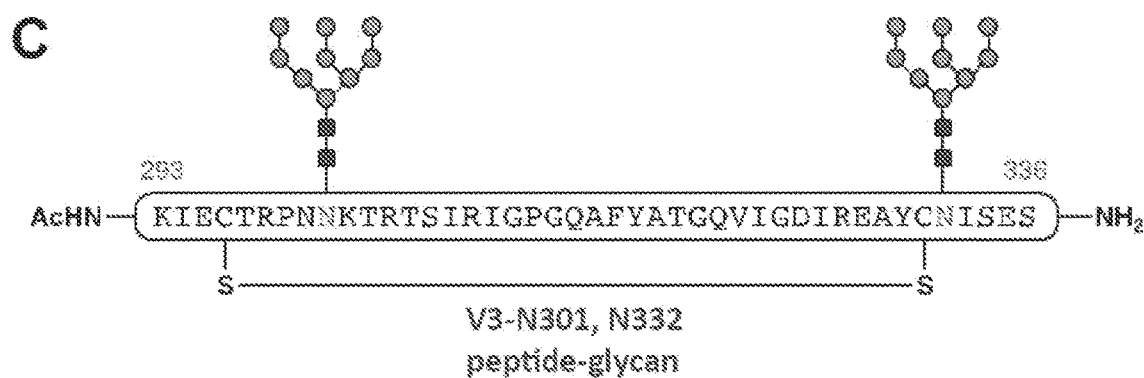

The initial set of constructs then will be based on the B.JRFL sequence, as the structure of this Env has been defined by cryo-electron microscopy at the ~11 Å level,[50] and since the JRFL "mini-V3" was used for the co-crystal structure with PGT128 discussed above.[6] B.JRFL will be used as a prototype to examine the effect of two types of structural modifications on antigenicity: (i) V3 loop truncation and (ii) V3 loop constraint. The former will be evaluated by comparing glycopeptides with full length and "mini-V3" segments. The "mini-V3" constructs follow the design of Pejchal et al,[6] as shown in FIG. 2B. To assess the effect of V3 loop constraint, the JRFL full length and mini-V3 constructs will each be made with and without the disulfide linkage between C296 and C331 (i.e., four constructs in all). As with the V1V2 glycopeptides synthesized previously, the N- and C-termini of all the V3 glycopeptides will be modified with acetyl and carboxamide moieties, respectively, to improve physiological stability, and also to avoid unnatural charges at the ends of the peptide.

Based on studies of binding of these four glycopeptides with Env anti-glycan BnAbs, the optimal peptide scaffold will be selected, and sC.CH505 and B.CH040 versions having the same configuration (i.e., full length or mini-V3; cyclic or linear) will be synthesized. Both C.CH505 and B.CH040 are transmitted/founder Envs. In the case of CH505, over 200 mAbs have been isolated from this subject and over 400 single genome amplified viral sequences over time from transmission. It has been found that immune pressure is exerted at N332. The transmitted/founder Env B.CH040 was found to be the target of an early autologous neutralizing antibody response that exerted selective pressure on the virus and may be easier to induce than BnAb reponses.[51] B.CH040-specific nAbs AbCH83 and AbCH84 were generated from day 132 B cell cultures, and were shown to target a conformational epitope at the base of V3. Binding of these neutralizing antibodies to B.CH040 Envs is blocked by PGTs 121, 125, and 130 (Haynes, B. F., unpublished data). Thus, a glycopeptide based on B.CH040 that is able to bind AbCH83 and AbCH84, as well as one or more of the broadly neutralizing PGTs, might be a good candidate for a priming vaccine, whereas immunogens based on either the B.JRFL or C.CH505 glycopeptides could form part of a boosting regimen.

Evaluation of the constructs will be performed. The glycopeptides will be tested for binding to the PGT121, 125, 128, and 130 BnAbs, as well as their germline precursors, by SPR and ELISA. The constructs will also be tested for binding to mAbs, AbCH83 and AbCH84.[51] The immediate outcome of these studies will be the identification of an optimal peptide "scaffold" suitable for exploring glycan structure-activity relationships. These investigations will also provide a logical starting point for the longer-term objective of delineating a minimal immunogen containing the relevant (likely sub-dominant) B cell determinants capable of driving the induction of PGT128-like BnAbs. Additionally, the results with the B.CH040 Env may also provide guidance for the development of rational prime/boost strategies for vaccination.

Two general approaches to assemble the glycopeptides will be pursued (FIG. 3). The first would be a maximally convergent strategy where the N332 and N301 glycans are installed simultaneously—a "one-fragment approach." Using standard Fmoc SPPS techniques, a peptide with general structure 12 would be generated with acid-labile side chain protecting groups, except at positions 332 and 301, which would possess free carboxylic acid aspartate side chains. Pseudoproline protection would be implemented at the critical N-glycosylation consensus sequence serine/threonine sites (at n+2, i.e., positions 303 and 305),[39] to ensure maximal efficiency in the double-aspartylation with the $Man_3GlcNAc_2$—$NH_2$ glycosyl amine. Subsequent acid-mediated side chain deprotection should afford glycopeptide 13, with free side chain thiols at C296 and C331. Under oxidative conditions, disulfide bond formation ought to be facile,[52] providing ready access to constrained V3 loop constructs 14.

A "two-fragment approach" will also be pursued. By this logic, the doubly-glycosylated peptide is derived from the coupling of two mono-glycosylated peptides. In this route, advantage would be taken of the conserved proline residue at position 313 for uniting the two fragments using proline ligation methodology.[47] The requisite ligation partners would be derived from peptide 15, bearing a C-terminal thioester, and peptide 16, carrying an N-terminal mercaptoproline auxiliary. These fragments would each be independently glycosylated and subjected to acid-mediated deprotection, yielding mono-glycosylated peptides 17 and 18. These two glycopeptides would then be joined under native chemical ligation conditions to afford doubly-glycosylated peptide 19. The auxiliary thiol at P313 would then be removed via metal-free dethiylation,[43] followed by oxidative Acm cleavage and concomitant disulfide formation,[52] thereby converging on the cyclic glycopeptides 14 targeted by the "one-fragment approach."

Figure 4:
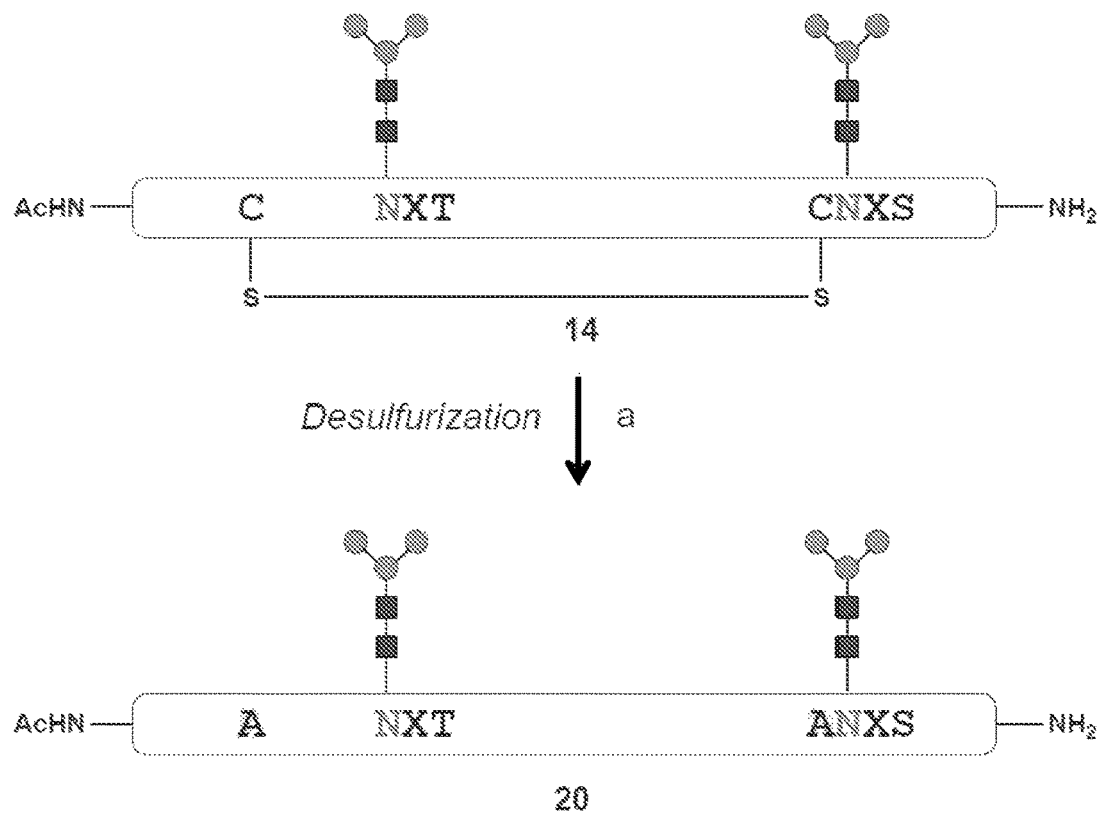
FIG. 4. Synthesis of linear (non-looped) gp120 V3-based glycopeptides. Reagents and conditions (a) Gnd HCl, TCEP, VA-044, t-BuSH, phosphate buffer, pH 7.2, 37° C.

To access the desired linear non-disulfide bonded constructs, the plan is to apply mild free-radical desulfurization conditions to either 13 or 14 to furnish acyclic glycopeptides with general structure 20, where removal of the sidechain thiols of C296 and C331 would effectively mutate those residues into alanines (FIG. 4). At this stage, making this chemical transformation is favored because reduced forms of 14 (i.e., 13) will be susceptible to spontaneous oxidative cyclization over time with exposure to trace $O_2$. Constructs of type 20 could, in principle, be arrived at simply by incorporating alanines at positions 296 and 331 in the original SPPS. However, from a strategic standpoint, it is generally more efficient to access structural diversity by branching from a late-stage intermediate, rather than an earlier one. Principles such as these form the basis of a chemical paradigm termed "diverted total synthesis."[53]

From a chemical standpoint, there are no fundamental technical barriers that need to be addressed in the synthesis of these constructs. What remains to be seen is whether the choice of $Man_3$ glycans will be appropriate to support a level of binding sufficient to allow the projected peptide-level structural comparisons to be made. While binding to $Man_3GlcNAc_2$ was not observed for PGT128 on glycan arrays, such results do not necessarily correlate with what the reality may be when the glycan is presented in the context of a peptide backbone. Still, PGT128 paratope mutations affecting hydrogen bonds to terminal mannose residues of $Man_9$ at N332 markedly diminished neutralization activity and binding to gp120 and protein-free $Man_9$, suggesting that the outer mannose units may indeed be important, if not indispensible. If so, and the $Man_3$ glycopeptides fail to show binding, then derivatives will be synthesized bearing $Man_9$ at both glycosylation sites. It is possible that the approach of using partial Env fragments may not be appropriate for mimicking the PGT128 epitope. A limited V3 domain construct could be too flexible relative to full length Env, leading to poorer binding. Such concerns formed part of the rationale for testing the disulfide-constrained and truncated V3 loop variants. If these constructs fail, a potential alternative would be to move the cysteine residues closer together (to occupy non-natural locations), so as to constrain the loop further, an approach that has shown promise in the context of purely peptidic V3 loop immunogens.[55] A second option would be to extend the size of the peptide domain in order to obtain a more stably folded structure. Indeed, in the limiting case, the entire engineered "mini-V3" gp120 outer domain construct used by Pejchal et al[6] could be synthesized with glycans at N332 and N301, using a combination of convergent aspartylation and NCL-based methods. While these technologies are sufficiently powerful to handle such an undertaking, the size of the target (190 aa) would probably not lend itself to a rapid prototyping of pure glycoforms. However, semi-synthetic methods (i.e., expressed protein ligation),[56] could well form the basis of a more practical approach where the glycopeptide fragment is generated by chemical synthesis, and the remaining peptide sequences are accessed by recombinant means.

Example 3

Described below is the synthesis of different V3 N332/N301 glycoforms and determination of the nature of the glycan residues that promote recognition by V3 anti-glycan BnAbs.

A systematic exploration will be undertaken of the effects of glycan structure at N332 and N301 on antigenicity toward known V3 glycan-directed BnAbs and their UCAs. As noted above, crystallographic studies[6] indicate that PGT128 uses a mode of recognition similar to the PG9-class[5] BnAbs where the epitope is formed by two glycans and a strand. In the electron density map, only the core pentasaccharide (Man$_5$GlcNAc$_2$) of the glycan at N301 is visible, whereas a Man$_8$ or Man$_9$ sugar is present at N332 (the terminal mannose of the D2 arm is not visible). Thus, the fine structures of the glycans that are necessary for recognition by V3 glycan-directed BnAbs have not been fully defined. Moreover, even less is known about the glycan preferences of the germline precursors of BnAbs. PGTs 125-128 and 130 showed binding to Man$_8$ and Man$_9$ oligosaccharides on glycan arrays,[4] but the involvement of other sugars is not definitively ruled out by negative results in such analyses. Experience with the V1V2 epitope indicates that failure of binding by isolated, protein-free carbohydrates is not conclusive, and argues for the importance of assaying these interactions with glycans presented in their native N-linked contexts.

Figure 5B:
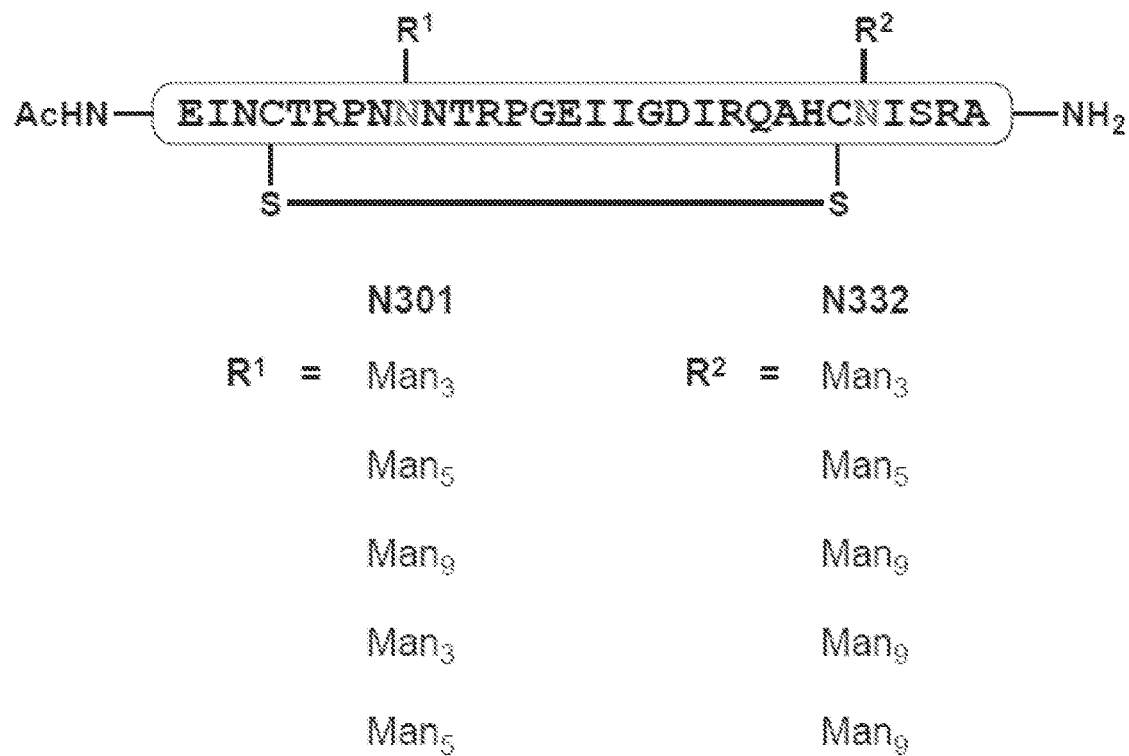

Generally speaking, the N-glycans of HIV-1 virion-associated Env are thought to be mainly high mannose (Man$_{5-9}$GlcNAc$_2$) sugars—especially Man$_5$—with complex-type oligosaccharides composing the remaining minority fraction.[57] The structures of a few oligomannose and a representative complex-type glycan are shown in FIG. 5A. The initial focus will be on evaluating the oligomannose glycans for which synthetic routes have been developed, that is, Man$_9$, Man$_5$, and Man$_3$. The optimal peptide scaffold will be selected and glycopeptides synthesized that are doubly glycosylated with Man$_5$ and Man$_9$ (the Man$_3$ variant having been prepared as described above) (see FIG. 5B with B.JRFL mini-V3 sequence). Versions where the N332 glycan is kept constant as Man$_9$ and the N301 glycan is varied (Man$_3$, Man$_5$) will also be synthesized, since only Man$_5$GlcNAc$_2$ is visible at the latter site in the PGT128 Fab-gp120 outer domain co-crystal structure.

The V3 glycopeptides will be evaluated as described above. Binding to PGTs 121, 125, 128, and 130 and their UCAs will be assessed by SPR and ELISA. Successful completion of these studies will help define the scope of oligomannose structures that can be recognized by these BnAbs in their native N-linked presentation. Using glycopeptides with homogeneous glycosylation will make it possible to elucidate the nature of these glycan-dependent epitopes with a level of specificity and control not provided by recombinant Env ligands with heterogeneous glycosylation. In particular, it is expected that the glycopeptides bearing different glycans at N332 and N301 will help to further characterize the properties of the secondary glycan-binding site of PGT128 (which recognizes the N301 glycan).

The constructs for this study should be accessible following the general strategies outlined in FIG. 3. The glycopeptides possessing the same glycans at N332 and N301 can be synthesized in the same manner as the constructs described above. The glycopeptides with discordant glycosylation at N332 and N301 will require a slightly modified route, but can, in principle, be reached by one- or two-fragment approaches. The one-fragment method would simply require that the carboxylic acid side chains of 12 at D332 and D301 be protected orthogonally, with sequential unmasking prior to the installation of each glycan. In the two-fragment mode, fragments 15 and 16 would each separately undergo aspartylation with different glycosylamines, giving rise to glycopeptides with two different sugars after ligation.

Figure 6:
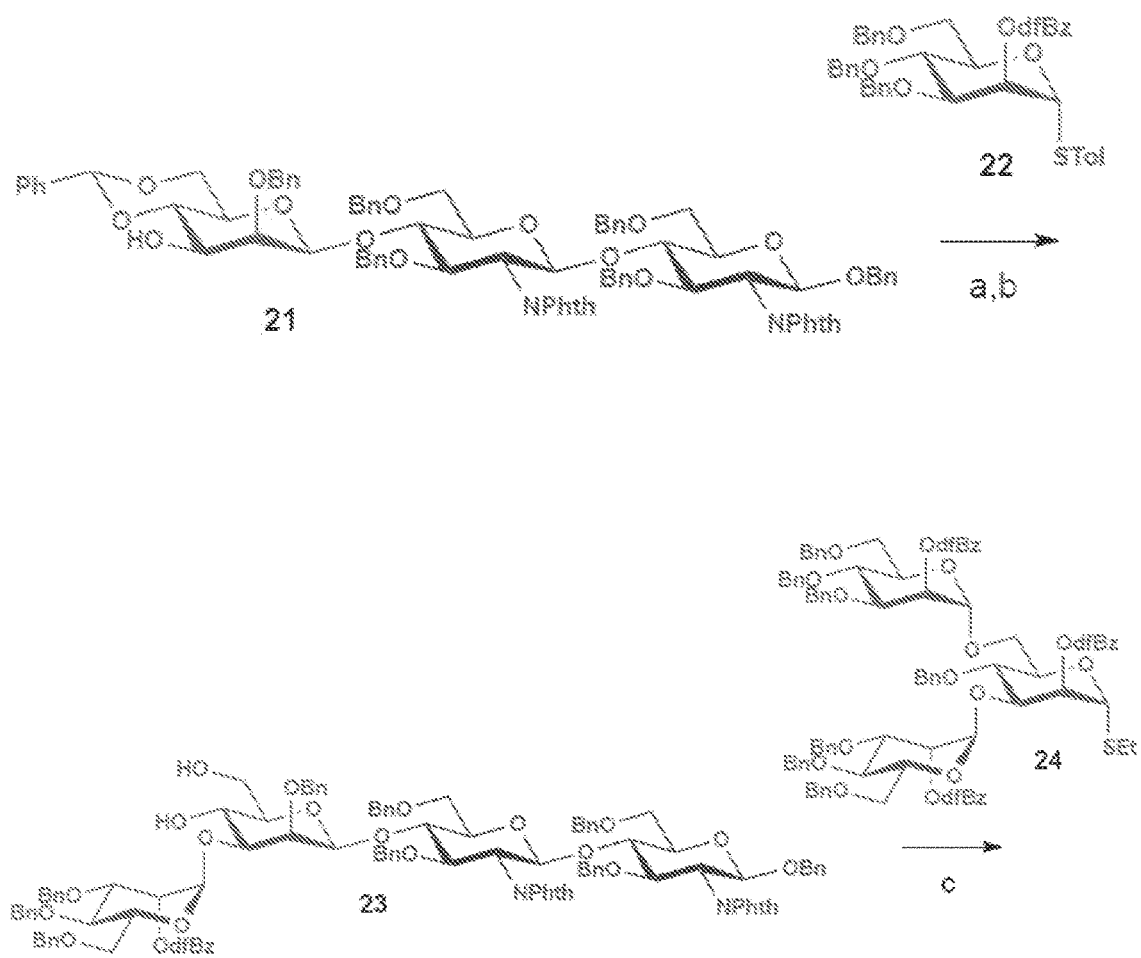
FIG. 6. Synthesis of Man₅GlcNAc₂ heptasaccharide 27. Reagents and conditions (a) thioglycoside 22. NIS/TM- SOT1, MS AW-300, $CH_2Cl_2$ 0° C.→r.t; (b) AcOH, $H_2O$), 63% (2 steps); (c) thioglycoside 24, NIS/TMSOTf, MS AW-300, $CH_2Cl_2$, 0° C.→r.t., 64%; (d) NaOMe, MeOH, $CH_2Cl_2$; (e) $H_2NCH_2CH_2NH_2$, n-BuOH, PhMe, 90° C.; (f) $Ac_2O$, $Et_3N$, MeOH quantitative (3 steps); (g) $H_2$, $Pd(OH)_2/C$, MeOH, $H_2O$, 75%; (f) sat. aq. $NH_4HCO_3$, 40° C., quantitative. Bn=benzyl, dfBz=2,5-difluorobenzoyl, MS AW-300=acid washed molecular sieves, NIS—N-iodosuccinimide, Phth=phthalimido, TMS=trimethylsilyl, Tol=tolyl.
Figure 6:
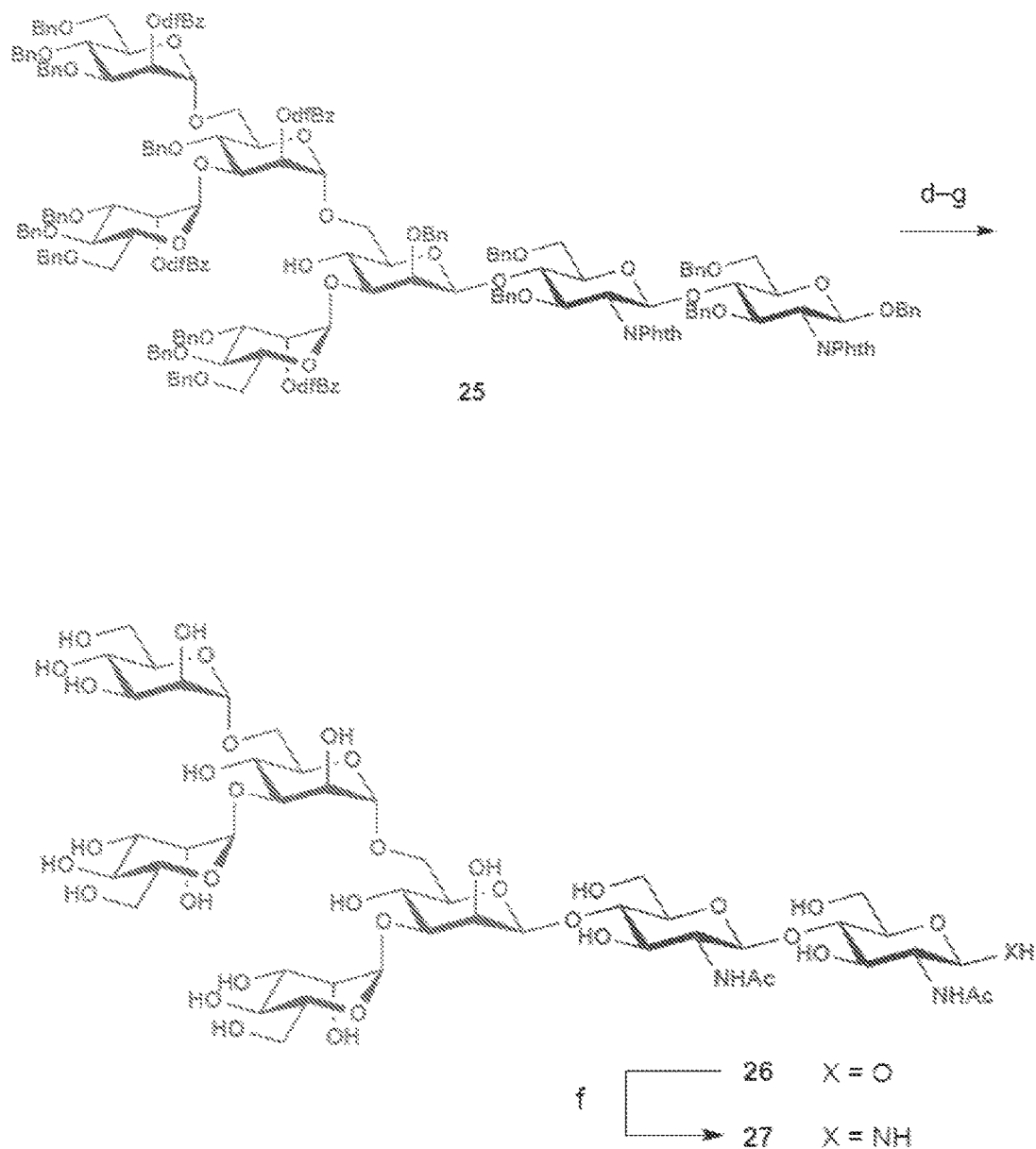

Access to the requisite synthetic oligosaccharides is assured, because the chemistry for assembling the Man$_9$, Man$_5$, and Man$_3$ glycans has been validated (the synthesis of Man$_5$ is exemplified in FIG. 6). Recently, a more streamlined approach to the ManGlcNAc$_2$ core trisaccharide 21 was adopted,[58] which was used in preparing the Man$_3$ and Man$_5$ glycans, and is amenable to greater material throughput. The overall logic of assembly is geared toward maximal convergence, where the common intermediate 21 is sequentially elaborated with linear trimannoside 28 and branched pentamannoside 29 (FIG. 7). Global deprotection by a sequence similar to that shown in FIG. 6, followed by Kochetkov amination[59] would afford glycosylamine 30. Hence, all of the glycans for this study can be accessed by a common strategy where 21 undergoes glycosylation at C-3 and C-6 with different oligomannosyl donors.

Figure 8:
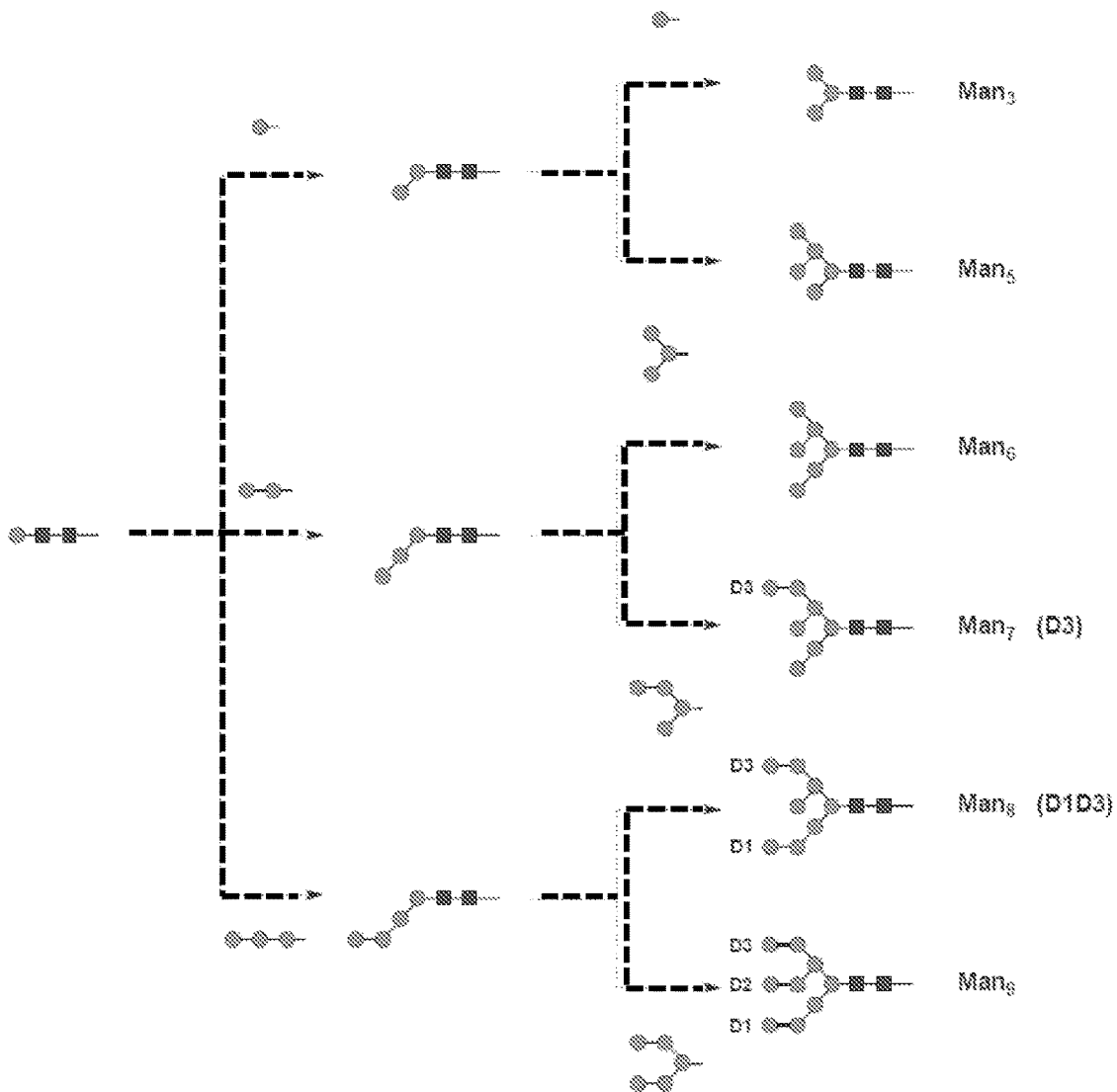
FIG. 8. Unified, maximally convergent strategy for synthesizing high mannose olosaccharides. Outline (omitting functional and protecting groups) illustrating how different combinations of branched and linear mannosyl donors can be used in stepwise fashion to elaborate the common Man-$GlcNAc_2$ trisaccharide core and access higher-order oligomannose derivatives.
Figure 9:
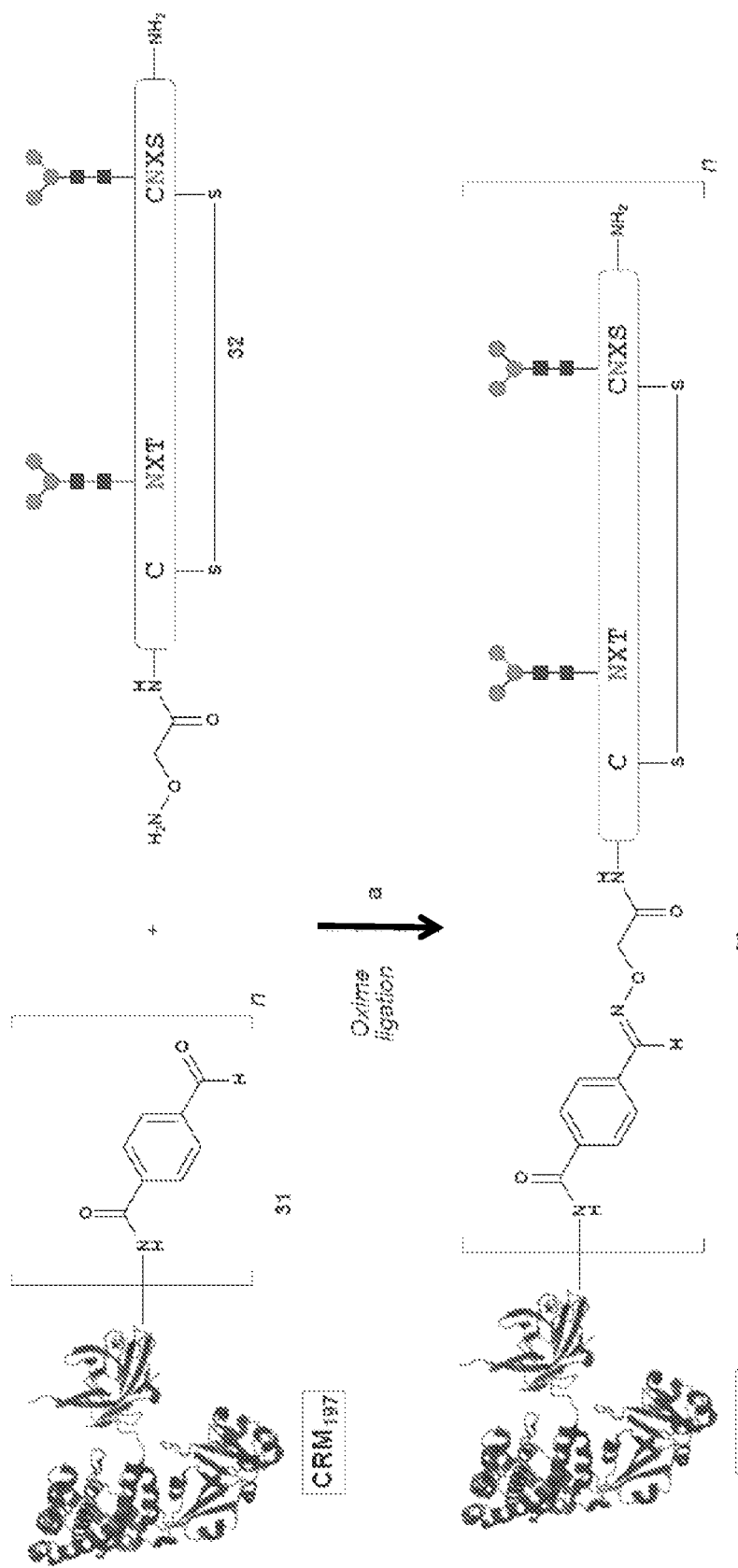
FIG. 9. Conjugation of glycopeptides to carrier protein via oxime ligation. Reagents and conditions: (a) 100 mM sodium phosphate buffer pH 6.5, 100 mM aniline.
Figure 10:
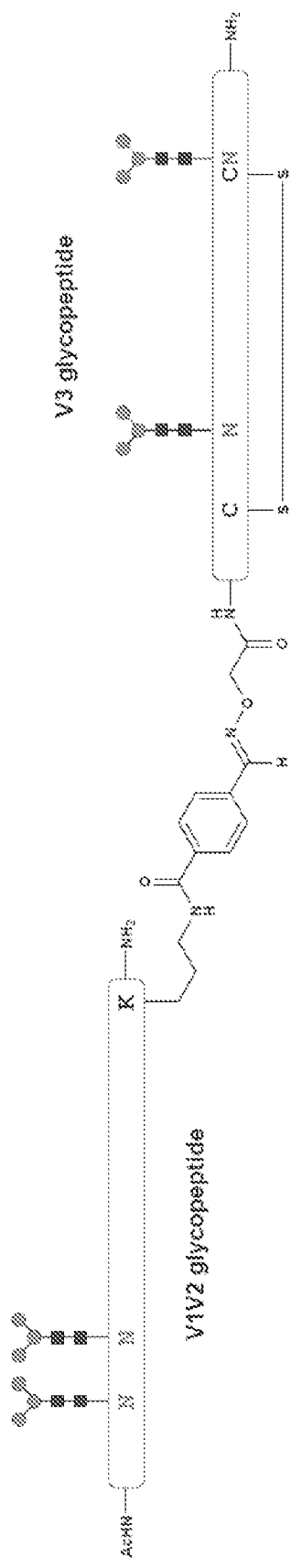
FIG. 10. Potential application of oxime ligation to build up unimolecular multivalent HIV-1 vaccines.

Further exploration and optimization of glycan structure may be necessary after evaluation of the initial collection of targeted glycoforms, if constructs displaying sufficient affinities for mature BnAbs and/or their UCAs do not emerge as candidates for further development. The range of oligomannose structures to be probed can be broadened. A global strategy for accessing essentially any of the high mannose oligosaccharides can be mapped out (FIG. 8). Using the ManGlcNAc$_2$ trisaccharide core as a starting point, use can be made of a limited number of linear and branched mannosyl donors in different combinations to achieve a "diverted total synthesis" of a full set of Man$_{3-9}$GlcNAc$_2$ glycans. In addition, hybrid or complex-type sugars can be incorporated. Constructs with complex-type N-glycans may be especially informative for the study of PGT121, which is sensitive to N332 for its neutralization activity,[4] binds complex-type, but not high mannose, oligosaccharides on glycan arrays, and yet still retains binding to high mannose-only forms of Env.[60] Hence, glycan recognition by PGT121 may be sufficiently promiscuous to accommodate either high mannose or complex-type sugars, which can be probed directly with homogeneous V3 constructs bearing each N-glycan form. Access to complex-type glycans can be obtained synthetically,[58,61] or by isolation from natural sources—in particular, the biantennary complex-type glycan depicted in FIG. 5A (with α2,6-sialylation) can be obtained from egg yolk[62] and its use in glycopeptide/glycoprotein semi-synthesis has been demonstrated by others.[63]

Example 4

Described below are methods for conjugating synthetic V3 glycopeptides and generating immunogens for testing in animal models.

An evaluation will be made of strategies for generating optimal humoral responses using the most promising constructs from above. It is contemplated that a minimal immunogen lacking interference from normally immunodominant epitopes and possessing sufficient affinity for the relevant UCA(s) will be able to initiate maturation of the desired sub-dominant B cell lineages that lead to BnAb induction. This concept will be tested by selecting two constructs that exhibit the best binding characteristics for V3-directed anti-glycan BnAbs and their UCAs and subjecting them to immunogenicity testing in rhesus macaques.

Versions of the constructs that are conjugated to carrier protein will be produced for the purposes of comparison. Carrier proteins used in currently licensed vaccines include tetanus toxoid (TT), diphtheria toxoid (DT), CRM$_{197}$ (cross-reactive material of diphtheria toxin$_{197}$), N. meningitidis outer membrane protein (OMP), and H. influenzae protein D.[64] For the initial studies, CRM$_{197}$, a non-toxic mutant (G52→D) of diphtheria toxin, will be selected which, unlike TT and DT, does not require chemical detoxification with formaldehyde. Thus, it is a well-defined, homogeneous 63 kD protein with a complete set of free, surface-exposed lysine chains (39 total), devoid of cross-linking, which are available for conjugation with potential haptens.[65] Keyhole limpet hemocyanin (KLH) would be a potential alternative.

A third option exists overall between these two limiting possibilities regarding the form of the immunogen (conjugated vs. unconjugated), which would be to join the V3 glycopeptides to a known T-helper peptide.

A non-human primate (NHP) study is contemplated. A 100 μg dose can be used, based on favorable results in previous NHP studies with that dose of Env. If inferior immune responses are observed when dosing at 100 μg, then the amount of immunogen is not likely to be the problem. Thus, each IM immunization of 100 μg glycopeptide in 0.5 ml of adjuvant can be divided in two sites (~0.25 mL per site). The adjuvant can be a squalene-based emulsion of 17% oil-in-saline with TLR7 and TLR9 agonists (R848 and 2006 type B oligo-CpGs) that has been shown to be effective in supporting the induction of anti-Env antibodies (Haynes, B. F., unpublished data).

The study groups for the first two V3 glycopeptide Env subunit immunogens can be:

Group 1: V3 glycopeptide #1, 100 μg IM×5 (6 monkeys) with adjuvant

Group 2: V3 glycopeptide #2, 100 μg IM×5 (6 monkeys) with adjuvant

Group 3: V3 glycopeptide #1 conjugated to $CRM_{197}$, 100 μg IM×5 (6 monkeys) with adjuvant Group 4: V3 glycopeptide #2 conjugated to $CRM_{197}$, 100 μg IM×5 (6 monkeys) with adjuvant Immunological evaluation can be performed as follows: each rhesus macaque can be heavily sampled systemically (blood/plasma) and mucosally (rectal/vaginal saliva fluids) before and two weeks after each immunization for profiling IgG and IgA vaccine-induced Env responses. Neutralization assays using both TZMb1 and A3R5 assays can be performed. In addition, competitive inhibition assays can be performed for vaccine induction of antibodies that bind to various Env epitopes including measurement of antibodies that can block PGT128, block CD4 binding site antibodies CH31 and VRC01, and antibodies that can block the binding of PG9, CH01 and 2G12 that recognize other glycosylated BnAb Env regions. Samples at select day 14 post immunization time points can be obtained for both VH and VL 454 deep sequencing as well as memory B cell cultures and/or antigen-specific B cell sorting to profile the B cell repertoire and ontogeny of induced antibodies. Finally, if acceptable immunogenicity is obtained, with a degree of breath in tier 2 neutralization obtained, the animals can be challenged with SHIV SF162P3 IR low dose repeat challenge. If poor breadth is obtained, animals can be re-boosted with new immunogens directed by B cell lineage design, to awaken the desired lineages for induction of PGT-like V3 peptide-glycan BnAbs prior to challenge.

Animals can be monitored for reactogenicity at the immunization sites, CBCs, and chemistries throughout the study.

Evaluation of this first round of vaccine candidates can establish whether the V3 glycopeptides are immunogenic enough (when formulated with appropriate adjuvants) to be used as pure immunogens. This approach would be most desirable from the standpoint of minimizing the likelihood of including potentially immunodominant epitopes that might overshadow a sub-dominant BnAb maturation pathway. Nevertheless, oligomerization of the antigen and/or the inclusion of more T-helper determinants may be necessary to achieve robust immune responses. Thus, parallel evaluation of glycopeptides conjugated to carrier protein can ensure that measurable humoral responses are obtained. Analysis of the quality of the humoral responses, namely, whether autologous and/or more broadly neutralizing activities are elicited, can reveal if the desired epitope conformation be can recognized by the immune system when presented in the context of a partial Env sequence.

The methods described herein can be scaled up for production of candidate glycopeptides in sufficient quantities for in vivo immunogenicity studies. For the conjugated constructs, selecting an efficient method for linking to carrier protein will be important. Many potential bioconjugation chemistries could potentially be applied,[66] but chemoselective ligation strategies that rely on thiol functionalities may be unsuitable for disulfide-containing constructs, due to the potential for disulfide exchange and scrambling.[67] Therefore, use of an oxime ligation approach in contemplated (FIG. 9). The oxime linkage is physiologically stable, and its formation proceeds under neutral aqueous buffer conditions when accelerated by aniline.[68] The requisite heterobifunctional linkers are commercially available, and can be incorporated using standard protocols. Sulfo-N-succinimidyl-4-formylbenzamide can be used to modify the lysine side chains of $CRM_{197}$ to present aldehydes (31), and incorporation of Boc-aminooxyacetic acid during SPPS can provide constructs of general structure 32 bearing oxyamine functionality at the N-terminus. Loading of glycopeptides 32 onto aldehyde-modified $CRM_{197}$ 31 can be accomplished by oxime formation in aqueous buffer in the presence of aniline, to furnish conjugated constructs such as 33. Degree of glycopeptide loading onto carrier protein (i.e., "n") can be assessed by matrix-assisted laser desorption/ionization time-of-flight mass spectrometry (MALDI-TOF MS).

A potential further application of the oxime ligation chemistry would be in the oligomerization of multiple V3 domains, which could be advantageous if carrier protein loading becomes a necessity (to increase the ratio of antigen to carrier). The ligation could also be employed to join multiple different domains together, which would enable the production of fully synthetic unimolecular multivalent HIV-1 vaccines (FIG. 10 5).

An alternative to using a carrier protein would be to join the antigen to a T-helper peptide, such as T1 (16 aa peptide from gp120 C4 region),[69, 70]. This option has some appeal, as a carrier protein could also carry immunodominant epitopes that might be detrimental for driving the kinds of B cell responses sought. It is possible that the V3 glycopeptide constructs may exhibit sufficient affinity for BnAbs and/or their UCAs through a kind of "induced-fit" mechanism, but still be sufficiently flexible that this desired conformation is not predominantly recognized by naïve B cell receptors. Remedies include strategies described above, (e.g., repositioning the disulfide constraint or extending the length of the peptide chain). It may also be feasible to constrain the V3 domain further by inserting it into a small protein that can serve as a scaffold (and access by semi-synthesis). If the neutralization activities observed are strain-specific, a strategy for addressing this would be to immunize sequentially, or as a mixture, constructs derived from different Envs. These constructs could also be linked together in a single molecular entity as discussed above (FIG. 10).

Example 5: Synthesis of V3 Glycopeptides

The overall design of these glycopeptide constructs is informed by the recently disclosed crystal structure of PGT128 Fab in complex with a glycosylated gp120 outer domain. See Pejchal, R.; Doores, K. J.; Walker, L. M.; Khayat, R.; Huang, P.-S.; Wang, S.-K.; Stanfield, R. L.; Julien, J.-P.; Ramos, A.; Crispin, M.; Depetris, R.; Katpally, U.; Marozsan, A.; Cupo, A.; Maloveste, S.; Liu, Y.; McBride, R.; Ito, Y.; Sanders, R. W.; Ogohara, C.; Paulson, J. C.; Feizi, T.; Scanlan, C. N.; Wong, C.-H.; Moore, J. P.; Olson, W. C.; Ward, A. B.; Poignard, P.; Schief, W. R.; Burton, D. R.; Wilson, I. A. "A potent and broad neutralizing antibody recognizes and penetrates the HIV glycan shield." *Science* 2011, 334, 1097-1103). The bound gp120 fragment was a chimeric construct consisting of a truncated B.JRFL V3 domain ("mini-V3") grafted onto a B.HXB2 base sequence. The structure of the complex revealed that PGT128 engages two glycans (at N332 and N301) and the C-terminal V3 stem. The planned constructs encompass these peptide and carbohydrate elements from the V3 region.

One of the key goals of this study was to access the Man$_9$GlcNAc$_2$ glycan (8) by chemical synthesis. The logic of assembly is the same as the route we developed for the Man$_5$GlcNAc$_2$ oligosaccharide, See Aussedat, B.; Vohra, Y.; Park, P. K.; Fernández-Tejada, A.; Alam, S. M.; Dennison, S. M.; Jaeger, F. H.; Anasti, K.; Stewart, S.; Blinn, J. H.; et al. Chemical Synthesis of Highly Congested gp120 V1V2 N-Glycopeptide Antigens for Potential HIV-1-Directed Vaccines. *J. Am. Chem. Soc.* 2013, 135, 13113-13120.) which is geared toward maximal convergence, where the common intermediate 9 is sequentially elaborated with linear trimannoside 10 and branched pentamannoside 11 (Scheme 1). The pentasaccharide 11 was constructed from building block 12 by an iterative double-glycosylation approach (Scheme 2). Mannosyl bis-acceptor 12 was glycosylated at the C-3 and C-6 positions with imidate donor 13 in 80% yield. Cleavage of the Lev protecting groups on the resulting trimannoside 14 with hydrazine unveiled the bis-acceptor for the second double glycosylation event with donor 16, which proceeded in 82% yield to furnish the desired pentameric thioglycoside donor 11.

The linear trisaccharide 10 was obtained by stepwise elongation of mannosyl acceptor 17 with imidate 16 (Scheme 3). The resulting trimannosyl thioglycoside 20 was then hydrolyzed to the anomeric alcohol and converted to the fluoro donor 10 in 82% yield over the two steps.

The final assembly of the undecamer 23 was accomplished by first uniting fragments 9 and 10 using Cp$_2$HfCl$_2$/AgOTf as the promoter (Scheme 4). The benzylidene acetal was subsequently cleaved with aqueous acetic acid, and the resulting diol 22 was selectively glycosylated at the 6-position with pentasaccharide donor 11 to afford the protected undecasaccharide 23. This substrate was subjected to a four-step deprotection sequence, then treated with aqueous sodium bicarbonate to generate glycosyl amine 8.

The V3 glycopeptides were assembled using two different approaches. For the constructs modified with the simpler chitobiose disaccharide, the glycans were installed by a double aspartylation on partially protected peptide 24, bearing free carboxylic acid sidechains at positions 301 and 332 (Scheme 5). Scheme 5 discloses SEQ ID NOS 10, 2 & 8 and 2 & 8, respectively, in order of appearance. Deprotection of the glycopeptide was followed by treatment with iodine to form the cyclic disulfide 26. The V3 glycopeptides bearing the more highly elaborated Man$_5$GlcNAc$_2$ and Man$_9$GlcNAc$_2$ glycans were put together using a "two-fragment" approach (as exemplified in Scheme 6). Scheme 6 discloses SEQ ID NOS 11-14 and 2 & 8, respectively, in order of appearance. Peptide fragments 27 and 28 were individually glycosylated, then following TFA deprotection, united via native chemical ligation. The resulting ligated product was then oxidized with iodine to afford cyclized constructs, such as 31.

Schemes

Scheme 1. Synthetic strategy to access Man$_9$GlcNAc$_2$ undecasaccharide 8.

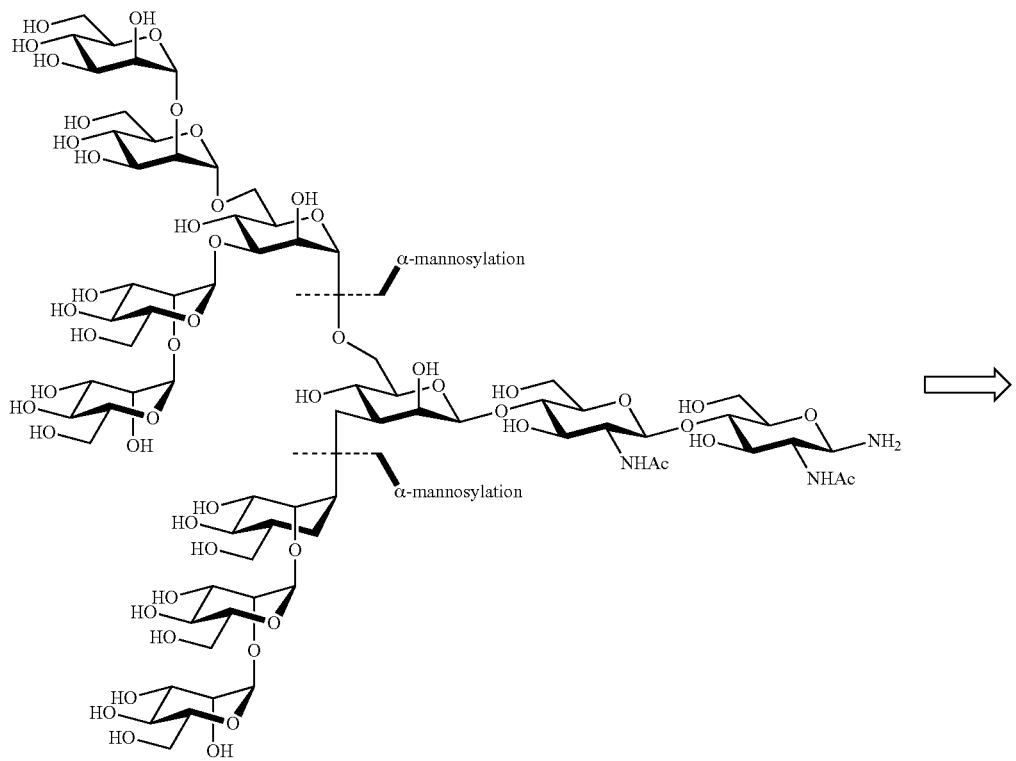

8

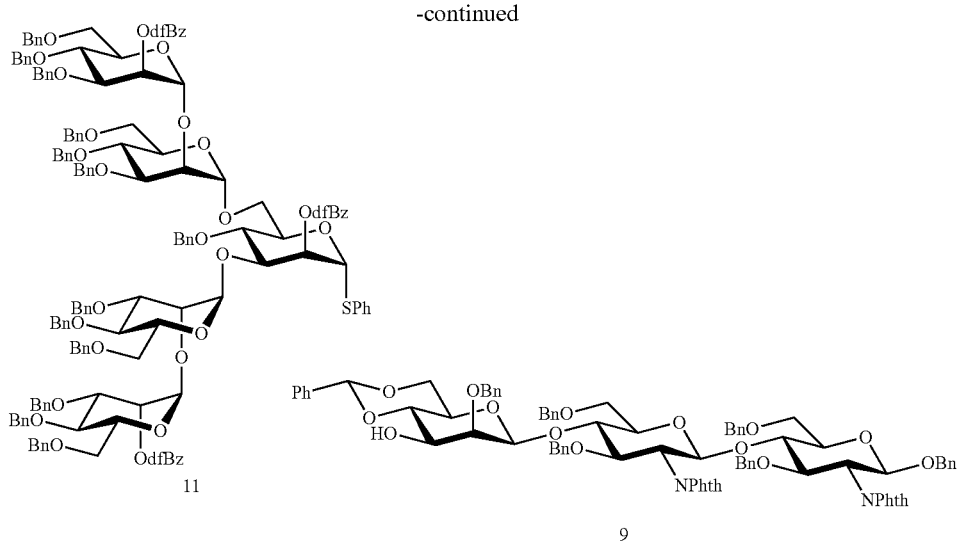
Scheme 2. Synthesis of branched pentamannoside 11.
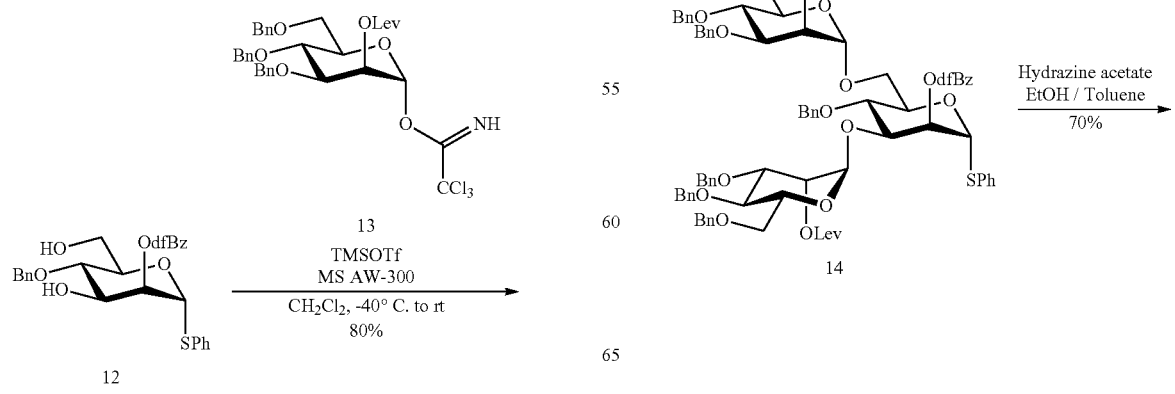

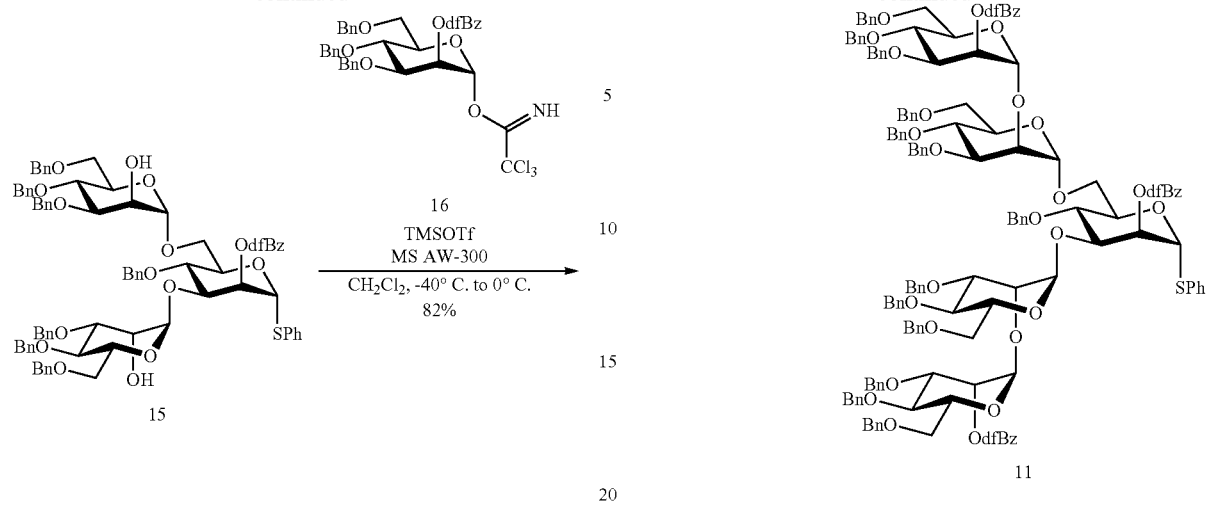
Scheme 3. Synthesis of linear trimannoside 10.
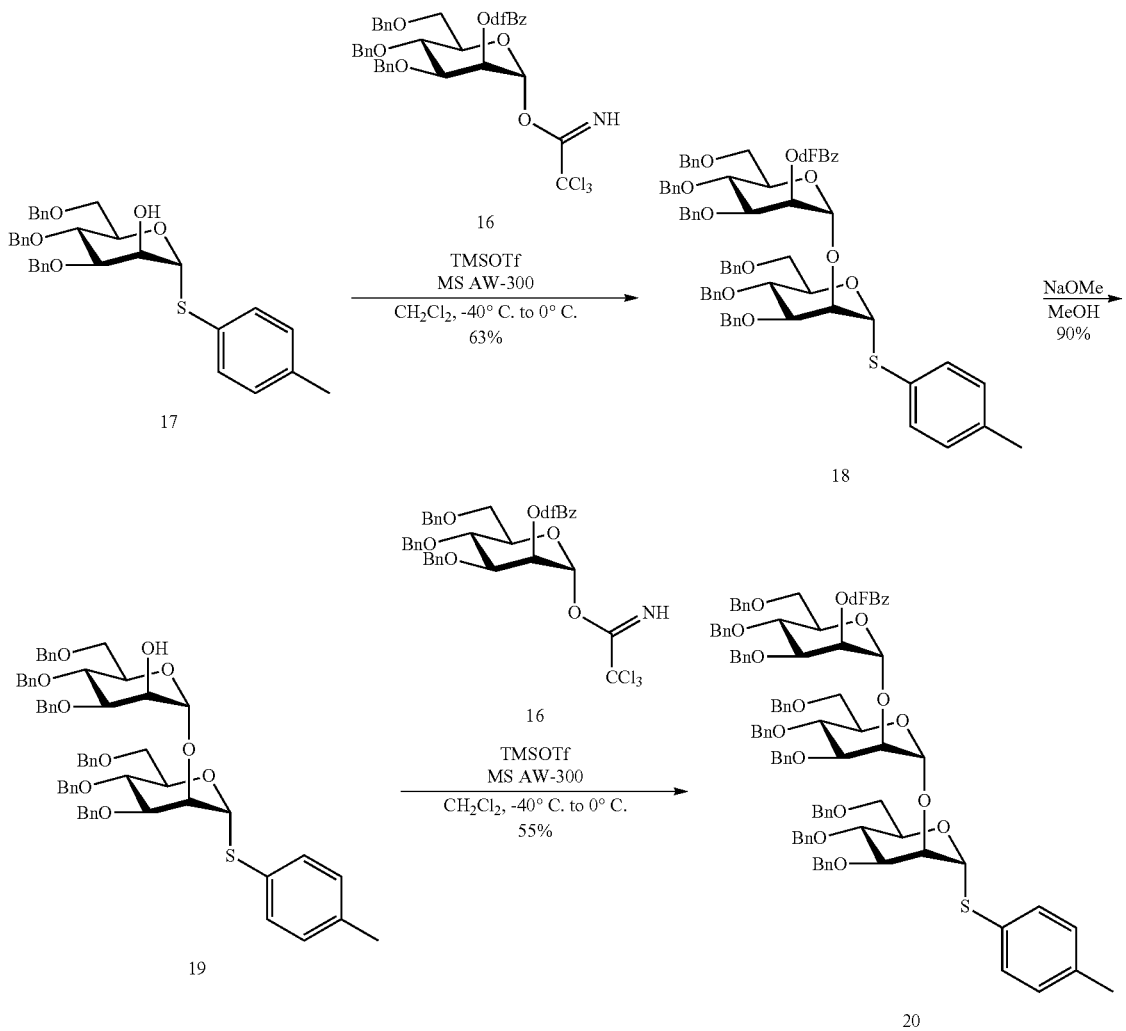

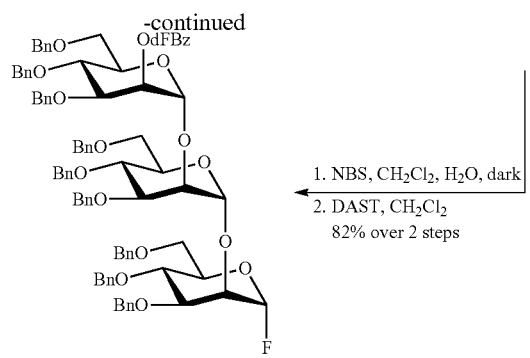

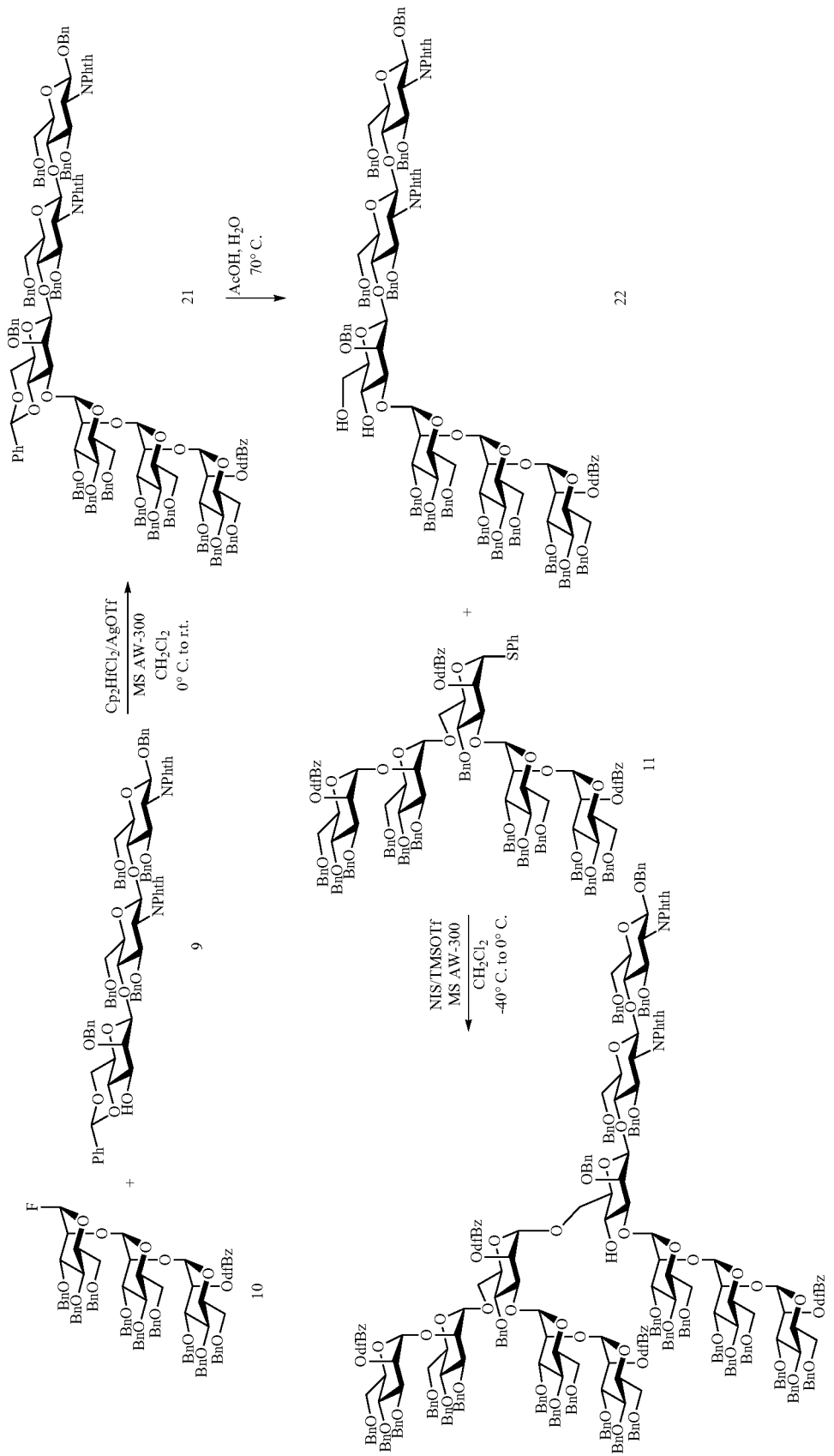
Scheme 4. Synthesis of Man9GlcNAc2 undecasaccharide 8.

-continued
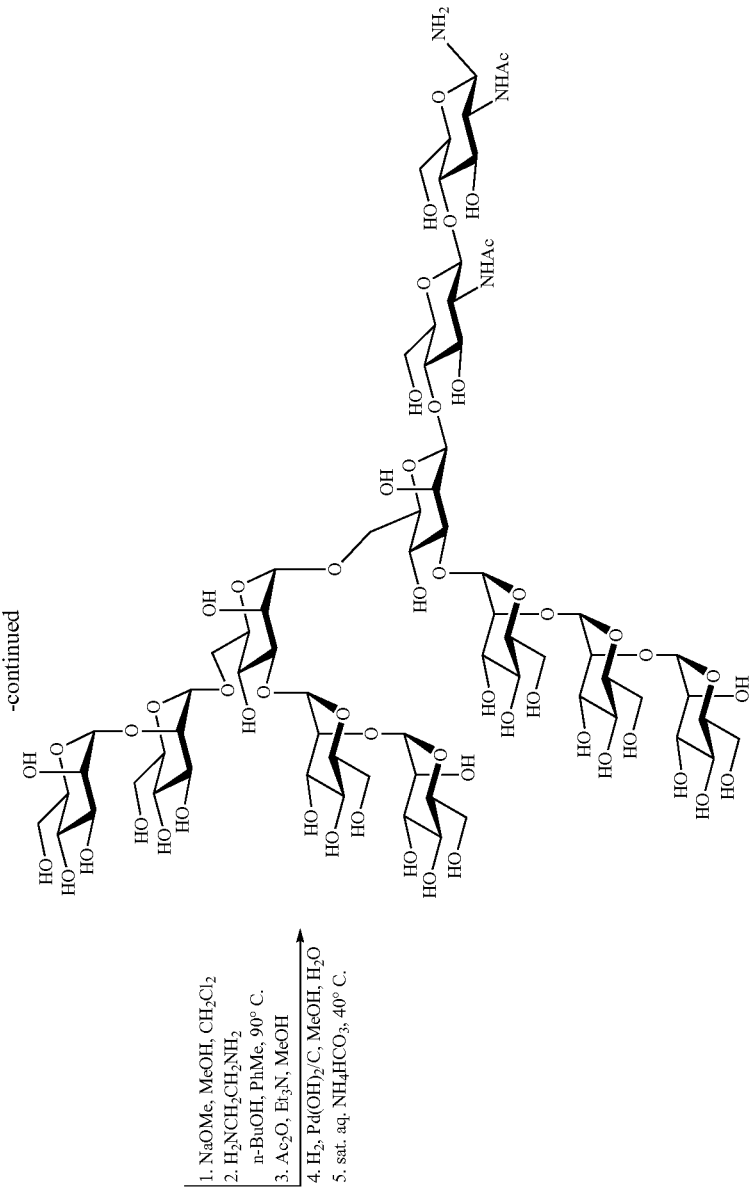
8

Scheme 5. Synthesis of GlcNAc2 V3 glycopeptide 26.
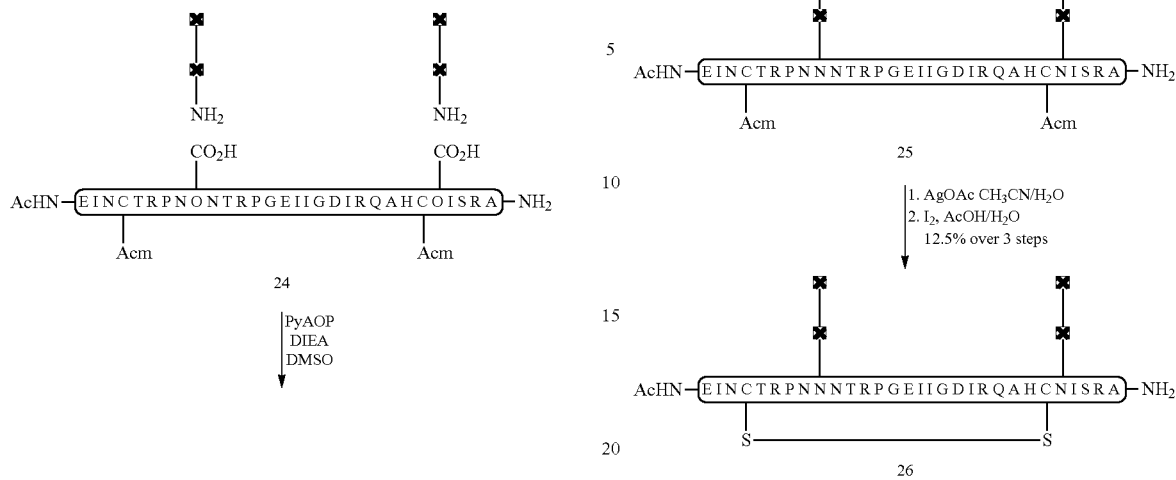
Scheme 6. Synthesis of Man5GlcNAc2 V3 glycopeptide 31.
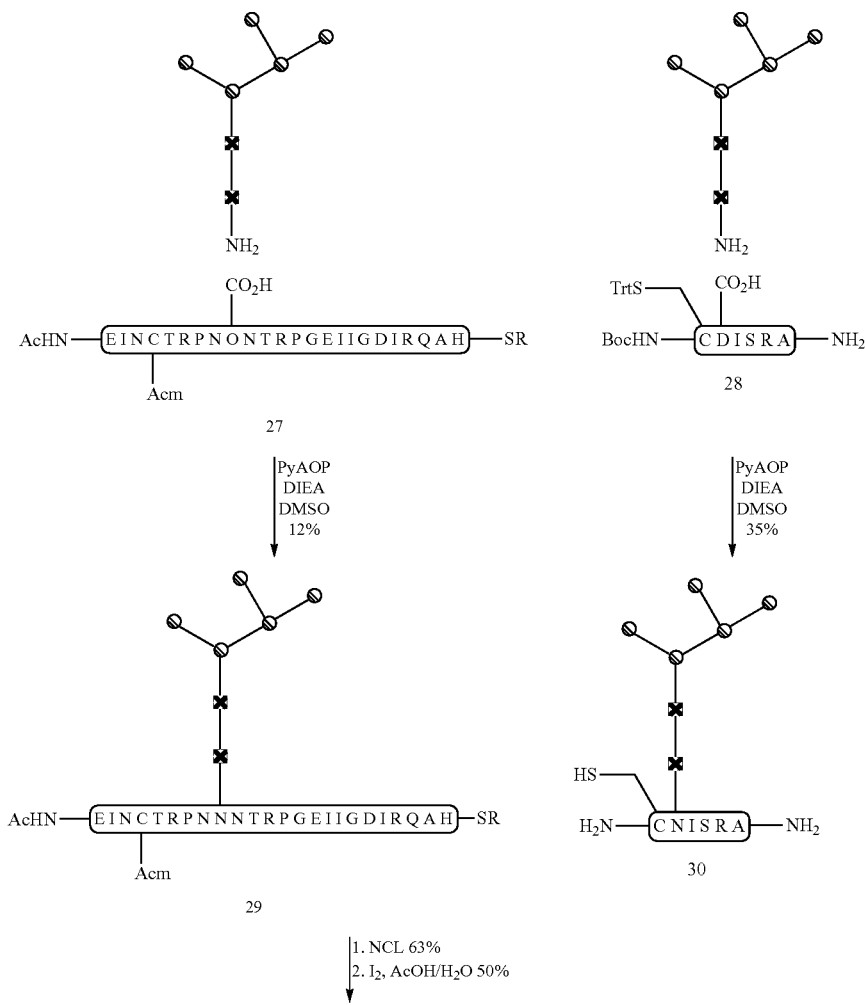

-continued

AcHN—[E I N C T R P N N N T R P G E I I G D I R Q A H C N I S R A]—NH₂
         |                                                   |
         S───────────────────────────────────────────────────S

31

FIGS. 14A and 14B show an analytical LCMS from a run of the synthesis, showing glycosylated V3 peptide. This was an analytical synthesis and LCMS analysis (where small quantities were analyzed), so the spectrum could be improved.

The product ran at a retention time of 2.6 min and the mass spectrum shows [M+4H]4+(1784.7) and [M+5H]5+ (1427.7) peaks. The sample was run on a Waters Acquity UPLC instrument, C8 column, 10-60% acetonitrile/water over 5 min at a flow rate of 0.3 mL/min.

The shoulder that is evident in the UV trace is from one of the glycopeptide fragments that was difficult to separate away from the final product. This will be corrected in a future synthesis. Since glycosylation is done chemically, the expectation is to achieve homogeneity in terms of glycosylation state.

Example 6

Figure 11:
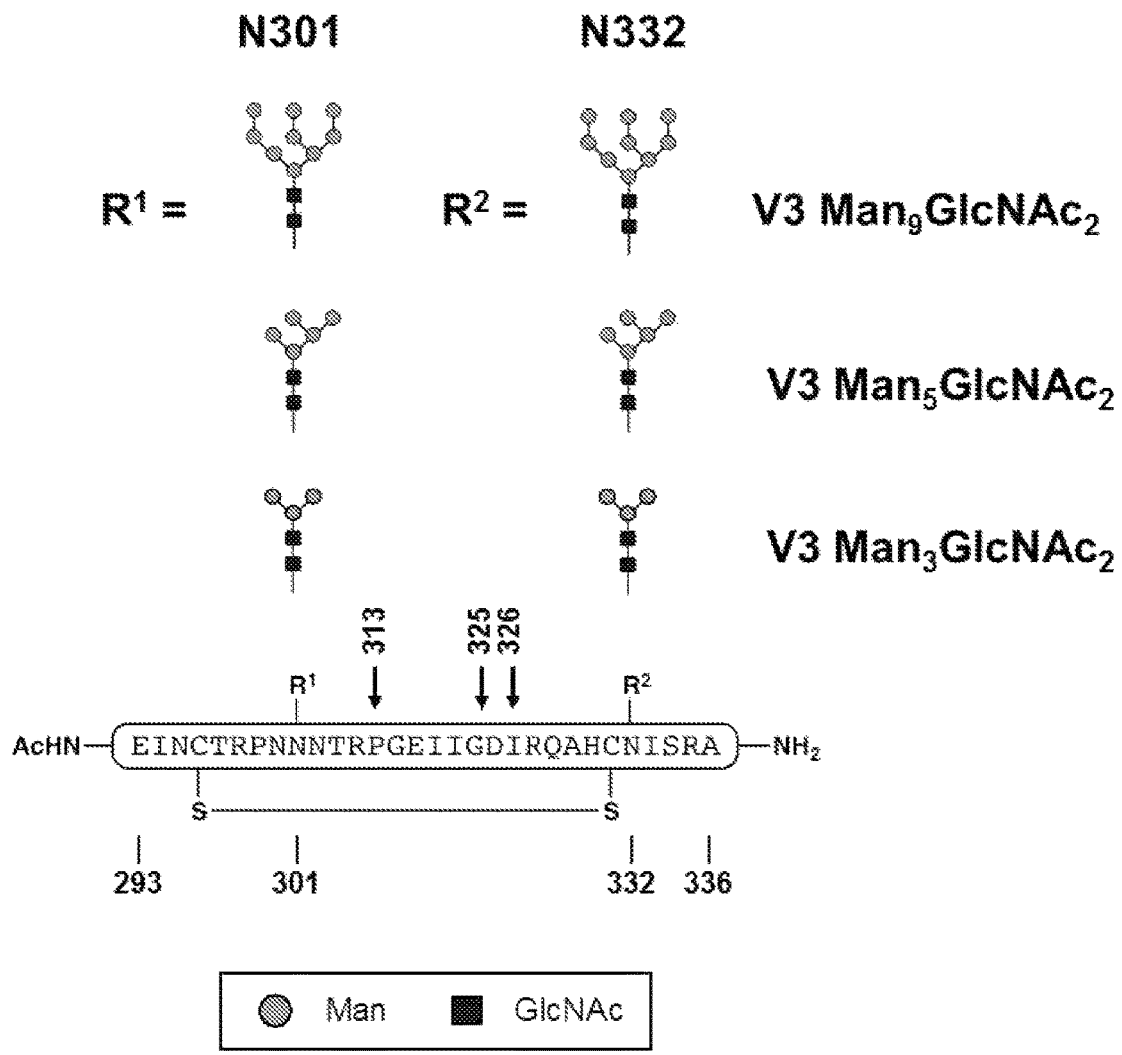
FIG. 11 shows one embodiment of a minimal V3 glycopeptide design (the linear peptide has SEQ ID NO: 8). Mini-V3 constructs was designed by deleting residues 305-320 and retaining P313. Sites of N-glycosylation are (N301/N332) colored red. Structure of synthetic V3 glycopeptides is based on the clade B JRFL mini-V3 peptide backbone. The mini-V3 constructs design is based on the structure of PGT 128 with a gp120 outer domain construct containing a truncated V3 loop (eODmV3) (Pejchal et al. 2011). The designed V3 immunogen is longer than the eODmV3 construct, having 30 aa of the V3 and with deletion of residues 305-320, while P313 is retained. The glycopeptide is cyclized through disulfide-bonding. The final V3 glycopeptide product has branched Man9 glycans (D1, D2, D3 arms) attached to proximal GlcNAc residues at positions N301 and N332.
Figure 12:
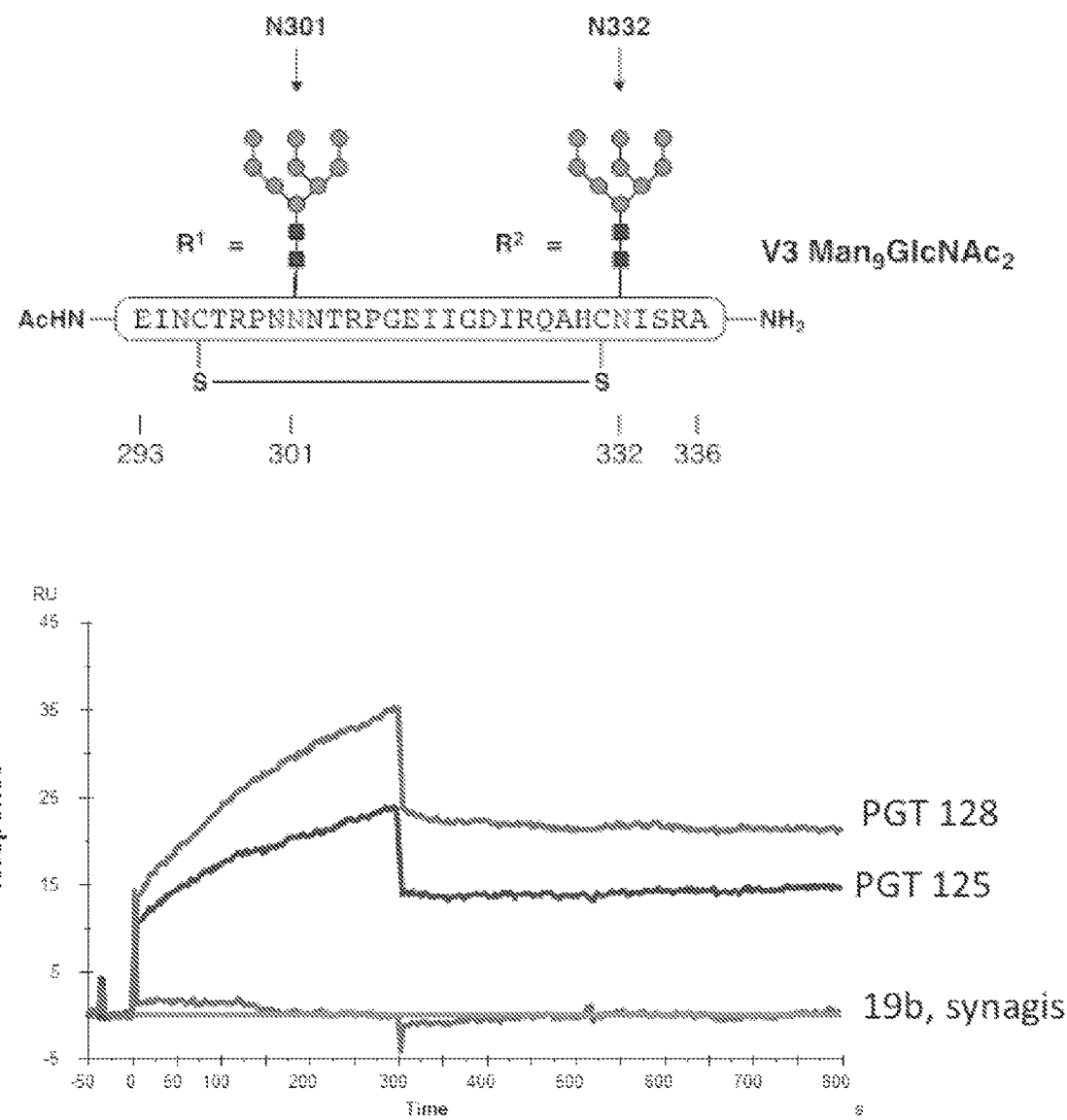
FIG. 12 shows binding of V3 BnAb (e.g. PGT128) to the Man9 V3 glycopeptide depicted in the figure (the linear peptide has SEQ ID NO: 8). Binding of V3 Bnab to V3-Man9 glycopeptide. SPR binding curves show preferential binding of PGT128 and PGT 125 BnAbs and thus, indicating that the synthetic glycopeptide optimally presents the Man9 glycans on the minimal V3 backbone. No binding was observed to the V3 loop non-neutralizing mAb 19b (green) or the negative control anti-RSV mAb Synagis (grey). Both PGT128 and PGT125 are dependent on Man9 glycans on position N332 and N301 (Pejchal et al., 2011), with N332 being the primary glycan. Mabs were captured on anti-Fc IgG immobilized sensor surfaces and the V3-Man9 glycopeptide injected to monitor binding responses on a BIAcore 300 instrument and as previously described (Alam et al., 2013). Non-specific binding to the control Synagis surface and blank buffer signal were subtracted.
Figure 13A:
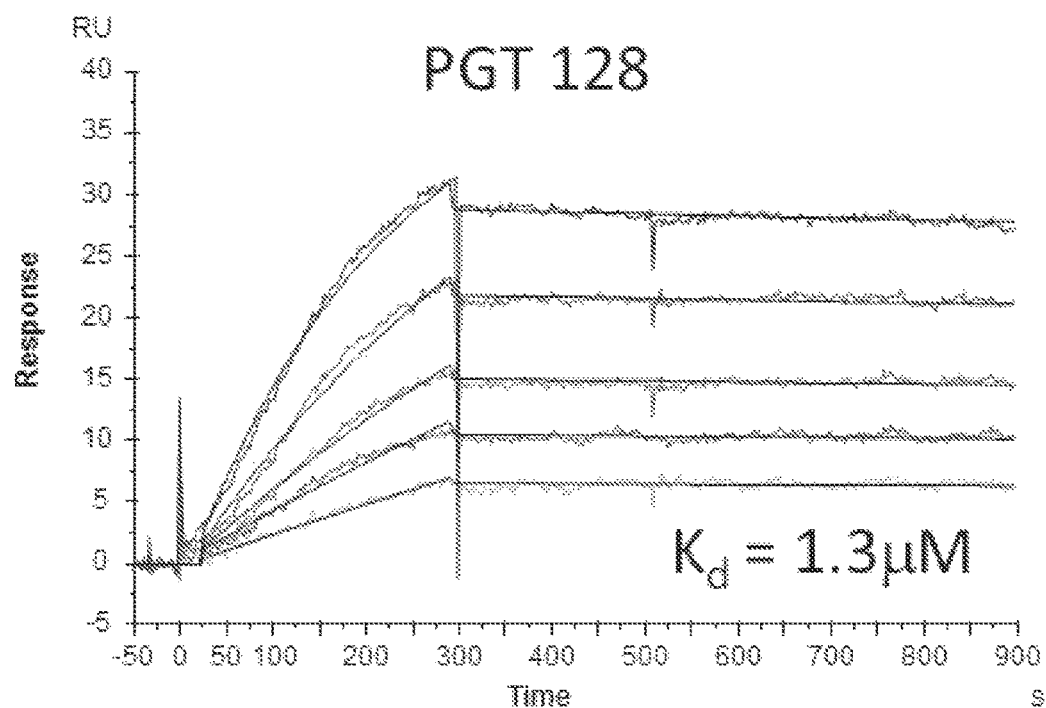
FIG. 13A-D show binding of PGT mAbs to synthetic $Man_9GlcNAc_2$ glycan. Binding of V3 Bnab to Man9 glycan. Both PGT128 and PGT125 bound to the Man9 glycan with affinities in μM (13A, 13B). 2G12 binding (13C) was only detected at the highest concentration of the glycan used, while there was no binding of the non-neutralizing V3 mAb 19b (magenta/top curve), or the V1V2 mAb PGT145 (green curve) (13D). Thus, the binding of Man9GlcnAc2 glycan was detected only for V3-glycan dependent PGT BNAbs. These data indicate that synthetic Man9 glycans can be used to detect antibodies that interact with both D1 and D3 arm of the glycans and bind preferentially to higher order branched oligomannose glycans.
Figure 13B:
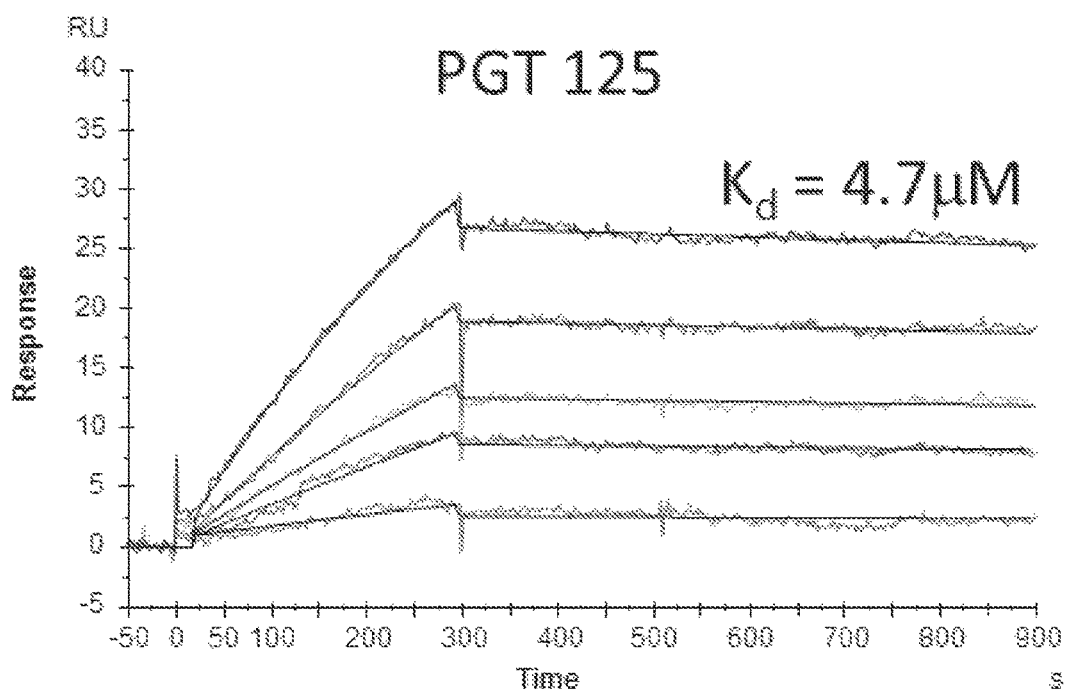
Figure 13C:
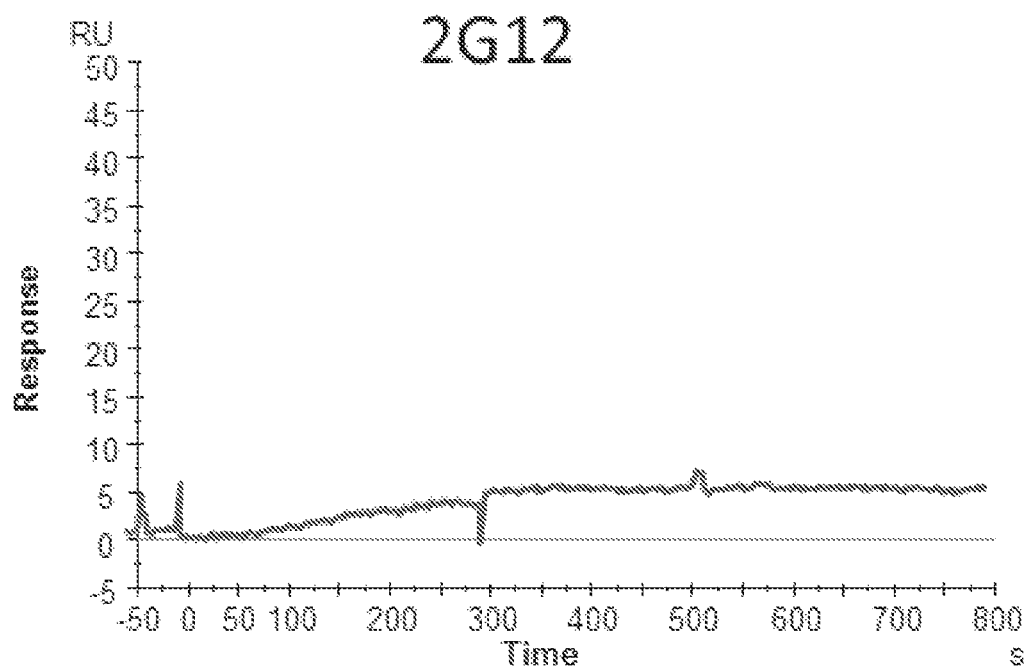
Figure 13D:
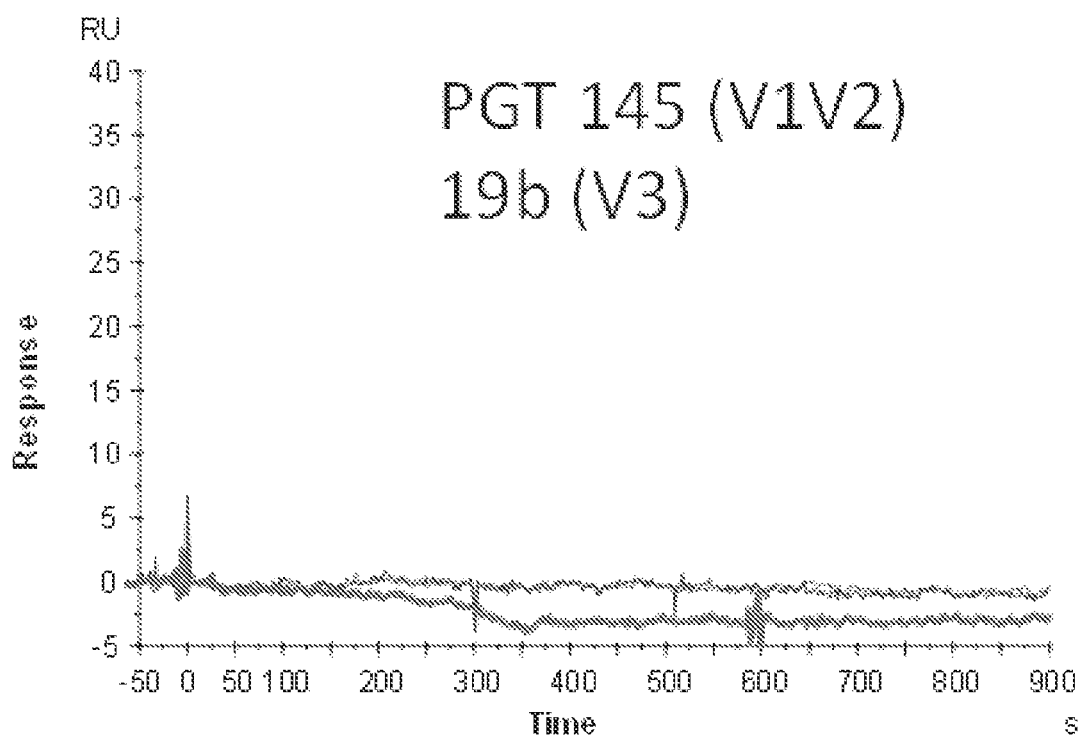

FIGS. 11-13 depict various experimental data showing that synthetic glycopeptides, such as for example the peptide of FIG. 1, can show differential binding to bnAbs vs non-neutralizing antibodies. From previous work it is know that V1V2 bnAbs PG9 and CH01 bound to disulfide-linked and mannose 5-derivatized glycopeptides, but did not show binding to aglycone V2 peptide. Both 2G12 mAb and 2G12 UCA bound well to Man5 V1V2 dimer, indicating recognition of the glycan cluster on a V2 backbone.

FIG. 12 shows that V3-Man9GlcNAc2 glycopeptide showed specific binding to PGT BnAbs (PGT 128, PGT 125).

PGT 128 binds to the terminal mannose residues of both D1 and D3 arms of branched Man$_8$/Man$_9$ glycans (Pejchal et al., 2011). 2G12 makes central contacts with the terminal Mana$_{1,2}$Man, at the tip of D1 arm of oligomannose glycan (Calarese et al., 2003). Thus, we tested the binding of the glycan-dependent BNAbs for binding to synthetic Man$_9$ glycan itself.

D3  Manα1-2Manα1
                \
                 6
                 Manα1
                3    \
                /     6
D2  Manα1-2Manα1      Manβ1-4GlcNAcβ1-4GlcNAc
                      3
                     /
D1  Manα1-2Manα1-2Manα1

FIG. 13 shows the Binding of PGT mAbs to synthetic Man$_9$-GlcNAc$_2$ glycan. In certain embodiments, the invention provides free sugars (Man$_5$ and/or Man$_9$ glycan). In other embodiments, the invention provides the Man9 and Man5 sugars with the biotin tag. In other embodiments, the invention provides the Man9 and Man5 sugars modified with glycosyl amine, for example to be used in the microarray platform.

Some embodiments use the free glycans (Man5, Man9) and while other embodiments use the same glycans on a peptide backbone. The free glycans will allow us to do large screening of vaccine samples to be able to select those that are strongly positives for glycan binding and include all positives based on just glycan recognition. The peptide associated glycans will allow to further discriminate between those that bind to V1V2 vs V3. It is likely that some antibodies bind to oligomannose clusters and could potentially be missed on certain glycopeptide constructs. So the differential binding using a combination of glycan, glycopeptide and aglycone will allow to narrow down the samples for isolating B cells using a more specific glycopeptide hook. The reagents described herein can be used to identify antibodies which recognize glycans, for example Man$_5$ and/or Man$_9$ glycan, antibodies which recognize glycopeptides modified with these glycans, and antibodies which recognize the aglycone peptide. The aglycone can also include any suitable tag, for example but not limited to biotin, at either peptide end. Any other suitable linker, for example but not limited to PEG linker could be inserted between the tag and the peptide. In some embodiment, this additional linker could increase the chance of an antibody recognizing the glycopeptide and/or aglycone peptide, when the peptide is immobilized.

Example 7

The Man$_9$GlcNAc$_2$ V3 ("Man$_9$ V3") glycopeptides of the invention, for example the peptide of FIG. 11, will be used in various non-limiting examples of immunogenicity regimens. In one embodiment, a Man$_9$ V3 glycopeptide is used in repetitive immunizations intramuscularly (IM) alone with an adjuvant for example but not limited to as a squalene based adjuvant, for example MF59, or a Toll-like receptor 4 agonist, for example GLA/SE (see Baldwin et al. *J Immunol*; Prepublished online 30 Jan. 2012). In another embodiment, a Man$_9$ V3glycopeptide will be used as a prime IM prior to IM boost with a V3 broad neutralizing epitope. In another embodiment, a Man$_9$ V3glycopeptide will be used as an IM boost for a prime by AE.A244 gp120.

All documents and other information sources cited herein are hereby incorporated in their entirety by reference.

REFERENCES (1) (a) McElrath, M. J.; Haynes, B. F. "Induction of immunity to human immunodeficiency virus type-1 by vaccination." *Immunity* 2010, 33, 542-554. (b) Haynes, B. F.; Kelsoe, G.; Harrison, S. C.; Kepler, T. B. "B-cell-lineage immunogen design in vaccine development with HIV-1 as a case study." *Nat. Biotechnol.* 2012, 30, 423-433.
(2) Burton, D. R.; Poignard, P.; Stanfield, R. L.; Wilson, I. A. "Broadly neutralizing antibodies present new prospects to counter highly antigenically diverse viruses." *Science* 2012, 337, 183-186.
(3) Walker, L. M.; Phogat, S. K.; Chan-Hui, P.-Y.; Wagner, D.; Phung, P.; Goss, J. L.; Wrin, T.; Simek, M. D.; Fling, S.; Mitcham, J. L.; Lehrman, J. K.; Priddy, F. H.; Olsen, O. A.; Frey, S. M.; Hammond, P. W.; Protocol G Principal Investigators; Kaminsky, S.; Zamb, T.; Moyle, M.; Koff, W. C.; Poignard, P.; Burton, D. R. "Broad and potent neutralizing antibodies from an African donor reveal a new HIV-1 vaccine target." *Science* 2009, 326, 285-289.
(4) Walker, L. M.; Huber, M.; Doores, K. J.; Falkowska, E.; Pejchal, R.; Julien, J.-P.; Wang, S.-K.; Ramos, A.; Chan-Hui, P.-Y.; Moyle, M.; Mitcham, J. L.; Hammond, P. W.; Olsen, O. A.; Phung, P.; Fling, S.; Wong, C.-H.; Phogat, S.; Wrin, T.; Simek, M. D.; Principal Investigators, P. G.; Koff, W. C.; Wilson, I. A.; Burton, D. R.; Poignard, P. "Broad neutralization coverage of HIV by multiple highly potent antibodies." *Nature* 2011, 477, 466-470.
(5) McLellan, J. S.; Pancera, M.; Carrico, C.; Gorman, J.; Julien, J.-P.; Khayat, R.; Louder, R.; Pejchal, R.; Sastry, M.; Dai, K.; O/'Dell, S.; Patel, N.; Shahzad-ul-Hussan, S.; Yang, Y.; Zhang, B.; Zhou, T.; Zhu, J.; Boyington, J. C.; Chuang, G.-Y.; Diwanji, D.; Georgiev, I.; Do Kwon, Y.; Lee, D.; Louder, M. K.; Moquin, S.; Schmidt, S. D.; Yang, Z.-Y.; Bonsignori, M.; Crump, J. A.; Kapiga, S. H.; Sam, N. E.; Haynes, B. F.; Burton, D. R.; Koff, W. C.; Walker, L. M.; Phogat, S.; Wyatt, R.; Orwenyo, J.; Wang, L.-X.; Arthos, J.; Bewley, C. A.; Mascola, J. R.; Nabel, G. J.; Schief, W. R.; Ward, A. B.; Wilson, I. A.; Kwong, P. D. "Structure of HIV-1 gp120 V1/V2 domain with broadly neutralizing antibody PG9." *Nature* 2011, 480, 336-343.
(6) Pejchal, R.; Doores, K. J.; Walker, L. M.; Khayat, R.; Huang, P.-S.; Wang, S.-K.; Stanfield, R. L.; Julien, J.-P.; Ramos, A.; Crispin, M.; Depetris, R.; Katpally, U.; Marozsan, A.; Cupo, A.; Maloveste, S.; Liu, Y.; McBride, R.; Ito, Y.; Sanders, R. W.; Ogohara, C.; Paulson, J. C.; Feizi, T.; Scanlan, C. N.; Wong, C.-H.; Moore, J. P.; Olson, W. C.; Ward, A. B.; Poignard, P.; Schief, W. R.; Burton, D. R.; Wilson, I. A. "A potent and broad neutralizing antibody recognizes and penetrates the HIV glycan shield." *Science* 2011, 334, 1097-1103.
(7) Verkoczy, L.; Kelsoe, G.; Moody, M. A.; Haynes, B. F. "Role of immune mechanisms in induction of HIV-1 broadly neutralizing antibodies." *Curr. Opin. Immunol.* 2011, 23, 383-390.
(8) Rerks-Ngarm, S.; Pitisuttithum, P.; Nitayaphan, S.; Kaewkungwal, J.; Chiu, J.; Paris, R.; Premsri, N.; Namwat, C.; De Souza, M.; Adams, E.; Benenson, M.; Gurunathan, S.; Tartaglia, J.; McNeil, J. G.; Francis, D. P.; Stablein, D.; Birx, D. L.; Chunsuttiwat, S.; Khamboonruang, C.; Thongcharoen, P.; Robb, M. L.; Michael, N. L.; Kunasol, P.; Kim, J. H. "Vaccination with ALVAC and AIDSVAX to prevent HIV-1 infection in Thailand." *N. Engl. J. Med.* 2009, 361, 2209-2220.
(9) (a) Haynes, B. F.; Gilbert, P. B.; McElrath, M. J.; Zolla-Pazner, S.; Tomaras, G. D.; Alam, S. M.; Evans, D. T.; Montefiori, D. C.; Karnasuta, C.; Sutthent, R.; Liao, H.-X.; DeVico, A. L.; Lewis, G. K.; Williams, C.; Pinter, A.; Fong, Y.; Janes, H.; DeCamp, A.; Huang, Y.; Rao, M.; Billings, E.; Karasavvas, N.; Robb, M. L.; Ngauy, V.; de Souza, M. S.; Paris, R.; Ferrari, G.; Bailer, R. T.; Soderberg, K. A.; Andrews, C.; Berman, P. W.; Frahm, N.; De Rosa, S. C.; Alpert, M. D.; Yates, N. L.; Shen, X.; Koup, R. A.; Pitisuttithum, P.; Kaewkungwal, J.; Nitayaphan, S.; Rerks-Ngarm, S.; Michael, N. L.; Kim, J. H. "Immune-correlates analysis of an HIV-1 vaccine efficacy trial." *N. Engl. J. Med.* 2012, 366, 1275-1286. (b) Montefiori, D. C.; Karnasuta, C.; Huang, Y.; Ahmed, H.; Gilbert, P.; de Souza, M. S.; McLinden, R.; Tovanabutra, S.; Laurence-Chenine, A.; Sanders-Buell, E.; Moody, M. A.; Bonsignori, M.; Ochsenbauer, C.; Kappes, J.; Tang, H.; Greene, K.; Gao, H.; LaBranche, C. C.; Andrews, C.; Polonis, V. R.; Rerks-Ngarm, S.; Pitisuttithum, P.; Nitayaphan, S.; Kaewkungwal, J.; Self, S. G.; Berman, P. W.; Francis, D.; Sinangil, F.; Lee, C.; Tartaglia, J.; Robb, M. L.; Haynes, B. F.; Michael, N. L.; Kim, J. H. "Magnitude and breadth of the neutralizing antibody response in the RV144 and Vax003 HIV-1 vaccine efficacy trials." *J. Infect. Dis.* 2012, 206, 431-441.
(10) Liao, H.-X. *Immunity* [Epub ahead of print] 10 Jan. 2013.
(11) Bonsignori, M.; Pollara, J.; Moody, M. A.; Alpert, M. D.; Chen, X.; Hwang, K.-K.; Gilbert, P. B.; Huang, Y.; Gurley, T. C.; Kozink, D. M.; Marshall, D. J.; Whitesides, J. F.; Tsao, C.-Y.; Kaewkungwal, J.; Nitayaphan, S.; Pitisuttithum, P.; Rerks-Ngarm, S.; Kim, J. H.; Michael, N. L.; Tomaras, G. D.; Montefiori, D. C.; Lewis, G. K.; DeVico, A.; Evans, D. T.; Ferrari, G.; Liao, H.-X.; Haynes, B. F. "Antibody-dependent cellular cytotoxicity-mediating antibodies from an HIV-1 vaccine efficacy trial target multiple epitopes and preferentially use the VH1 gene family." *J. Virol.* 2012, 86, 11521-11532.
(12) (a) Gray, E. S.; Madiga, M. C.; Hermanus, T. et al. "The Neutralization Breadth of HIV-1 Develops Incrementally over Four Years and Is Associated with CD4+ T Cell Decline and High Viral Load during Acute Infection." *J. Virol.* 2011, 85, 4828-4840. (b) Tomaras, G. D.; Binley, J. M.; Gray, E. S. et al. "Polyclonal B Cell Responses to Conserved Neutralization Epitopes in a Subset of HIV-1-Infected Individuals." *J. Virol.* 2011, 85, 11502-11519.
(13) (a) Hessell, A. J.; Poignard, P.; Hunter, M. "Effective, low-titer antibody protection against low-dose repeated mucosal SHIV challenge in macaques." *Nat. Med.* 2009, 15, 951-954. (b) Hessell, A. J.; Rakasz, E. G.; Tehrani, D. M. et al. "Broadly Neutralizing Monoclonal Antibodies 2F5 and 4E10 Directed against the Human Immunodeficiency Virus Type 1 gp41 Membrane-Proximal External Region Protect against Mucosal Challenge by Simian-Human Immunodeficiency Virus $SHIV_{Ba-L}$." *J. Virol.* 2010, 84, 1302-1313.
(14) Moldt, B.; Rakasz, E. G.; Schultz, N. et al. "Highly potent HIV-specific antibody neutralization in vitro translates into effective protection against mucosal SHIV challenge in vivo." *Proc. Natl. Acad. Sci. USA* 2012, 109, 18921-18925.
(15) Malherbe, D. C.; Doria-Rose, N. A.; Misher, L. et al. "Sequential Immunization with a Subtype B HIV-1 Envelope Quasispecies Partially Mimics the In Vivo Development of Neutralizing Antibodies. *J. Virol.* 2011, 85, 5262-5274.
(16) (a) Go, E. P.; Hewawasam, G.; Liao, H.-X. et al. "Characterization of Glycosylation Profiles of HIV-1 Transmitted/Founder Envelopes by Mass Spectrometry." *J. Virol.* 2011, 85, 8270-8284. (b) Clark, D. F.; Go, E. P.; Desaire, H. "A Simple Approach to Assign Disulfide Connectivity Using Extracted Ion Chromatograms of Electron Transfer Dissociation Spectra." *Anal. Chem.* [Online early access]. DOI: 10.1021/ac303124w. Published Online: Dec. 4, 2012. http://pubs.acs.org (accessed Jan. 2, 2013).
(17) Wang, P.; Dong, S.; Brailsford, J. A.; Townsend, S. D.; Zhang, Q.; Iyer, K.; Hendrickson, R. C.; Shieh, J. H.; Moore, M. A. S.; Danishefsky, S. J. "At Last: Erythropoietin as a Single Glycoform" *Angew. Chem. Int. Ed.* 2012, 51, 11576-11584. PMCID: PMC3500780.
(18) Bonsignori, M.; Hwang, K.-K.; Chen, X.; Tsao, C.-Y.; Morris, L.; Gray, E.; Marshall, D. J.; Crump, J. A.; Kapiga, S. H.; Sam, N. E.; Sinangil, F.; Pancera, M.;

(18) Yongping, Y.; Zhang, B.; Zhu, J.; Kwong, P. D.; O'Dell, S.; Mascola, J. R.; Wu, L.; Nabel, G. J.; Phogat, S.; Seaman, M. S.; Whitesides, J. F.; Moody, M. A.; Kelsoe, G.; Yang, X.; Sodroski, J.; Shaw, G. M.; Montefiori, D. C.; Kepler, T. B.; Tomaras, G. D.; Alam, S. M.; Liao, H.-X.; Haynes, B. F. "Analysis of a clonal lineage of HIV-1 envelope V2/V3 conformational epitope-specific broadly neutralizing antibodies and their inferred unmutated common ancestors." *J. Virology* 2011, 85, 9998-10009.

(19) Rolland, M.; Edlefsen, P. T.; Larsen, B. B.; Tovanabutra, S.; Sanders-Buell, E.; Hertz, T.; deCamp, A. C.; Carrico, C.; Menis, S.; Magaret, C. A.; Ahmed, H.; Juraska, M.; Chen, L.; Konopa, P.; Nariya, S.; Stoddard, J. N.; Wong, K.; Zhao, H.; Deng, W.; Maust, B. S.; Bose, M.; Howell, S.; Bates, A.; Lazzaro, M.; O'Sullivan, A.; Lei, E.; Bradfield, A.; Ibitamuno, G.; Assawadarachai, V.; O'Connell, R. J.; deSouza, M. S.; Nitayaphan, S.; Rerks-Ngarm, S.; Robb, M. L.; McLellan, J. S.; Georgiev, I.; Kwong, P. D.; Carlson, J. M.; Michael, N. L.; Schief, W. R.; Gilbert, P. B.; Mullins, J. I.; Kim, J. H. "Increased HIV-1 vaccine efficacy against viruses with genetic signatures in Env V2." *Nature* 2012, 490, 417-420.

(20) Kwong, P. D.; Mascola, J. R. "Human Antibodies that Neutralize HIV-1: Identification, Structures, and B Cell Ontogenies." *Immunity* 2012, 37, 412-425.

(21) Despite great strides in recombinant technologies using engineered organisms, complete and precise control of glycoform expression has remained elusive. For a recent review, see: Wang, L.-X.; Lomino, J. V. "Emerging technologies for making glycan-defined glycoproteins." *ACS Chem. Biol.* 2011.

(22) (a) Kornfeld, R.; Kornfeld, S. Assembly of asparagine-linked oligosaccharides. *Annu. Rev. Biochem.* 1985, 54, 631-664. (b) Rudd, P. M.; Dwek, R. A. "Glycosylation: Heterogeneity and the 3D structure of proteins" *Crit. Rev. Biochem. Mol. Biol.* 1997, 32, 1-100. (c) Spiro, R. G. "Protein glycosylation: nature, distribution, enzymatic formation, and disease implications of glycopeptide bonds" *Glycobiology* 2002, 12,43R-56R.

(23) (a) Davis, B. G. "Synthesis of glycoproteins." *Chemical Reviews* 2002, 102, 579-602. (b) Gamblin, D. P.; Scanlan, E. M.; Davis, B. G. "Glycoprotein synthesis: An update." *Chem. Rev.* 2009, 109, 131-163.

(24) Kan, C.; Danishefsky, S. J. "Recent Departures in the Synthesis of Peptides and Glycopeptides" *Tetrahedron (Perspective)* 2009, 65, 9047-9065. PMCID: PMC2780351.

(25) Yu, B.; Morales, J. F.; O'Rourke, S. M.; Tatsuno, G. P.; Berman, P. W. "Glycoform and net charge heterogeneity in gp120 Immunogens used in HIV vaccine trials." *PLoS ONE* 2012, 7, e43903.

(26) (a) Wang, L.-X. "Toward oligosaccharide- and glycopeptide-based HIV vaccines." *Curr. Opin. Drug Discov. Devel.* 2006, 9, 194-206. (b) Morelli, L.; Poletti, L.; Lay, L. "Carbohydrates and immunology: Synthetic oligosaccharide antigens for vaccine formulation." *Eur. J. Org. Chem.* 2011, 2011, 5723-5777.

(27) (a) Trkola, A.; Purtscher, M.; Muster, T.; Ballaun, C.; Buchacher, A.; Sullivan, N.; Srinivasan, K.; Sodroski, J.; Moore, J. P.; Katinger, H. "Human monoclonal antibody 2G12 defines a distinctive neutralization epitope on the gp 120 glycoprotein of human immunodeficiency virus type 1." *J. Virology* 1996, 70, 1100-1108. (b) Scanlan, C. N.; Pantophlet, R.; Wormald, M. R.; Ollmann Saphire, E.; Stanfield, R.; Wilson, I. A.; Katinger, H.; Dwek, R. A.; Rudd, P. M.; Burton, D. R. "The broadly neutralizing anti-human immunodeficiency virus type 1 antibody 2G12 recognizes a cluster of α1→2 mannose residues on the outer face of gp120." *J. Virology* 2002, 76, 7306-7321. (c) Calarese, D. A.; Scanlan, C. N.; Zwick, M. B.; Deechongkit, S.; Mimura, Y.; Kunert, R.; Zhu, P.; Wormald, M. R.; Stanfield, R. L.; Roux, K. H.; Kelly, J. W.; Rudd, P. M.; Dwek, R. A.; Katinger, H.; Burton, D. R.; Wilson, I. A. "Antibody domain exchange is an immunological solution to carbohydrate cluster recognition." *Science* 2003, 300, 2065-2071.

(28) Zhu, J.; Warren, J.; Danishefsky, S. "Synthetic carbohydrate-based anticancer vaccines: The Memorial Sloan-Kettering experience." *Expert Rev. Vaccines* 2009, 8, 1399. PMCID: PMC3063993.

(29) (a) Bilodeau, M. T.; Park, T. K.; Hu, S.; Randolph, J. T.; Danishefsky, S. J.; Livingston, P. O.; Zhang, S. "Total Synthesis of a Human Breast Tumor Associated Antigen." *J. Am. Chem. Soc.* 1995, 117, 7840-7841. (b) Park, T. K.; Kim, I. J.; Hu, S.; Bilodeau, M. T.; Randolph, J. T.; Kwon, 0.; Danishefsky, S. J. "Total Synthesis and Proof of Structure of a Human Breast Tumor (Globo-H) Antigen." *J. Am. Chem. Soc.* 1996, 118, 11488-11500. (c) Ragupathi, G.; Park, T. K.; Zhang, S.; Kim, I. J.; Graber, L.; Adluri, S.; Lloyd, K. O.; Danishefsky, S. J.; Livingston, P. O. "Immunization of Mice with a Fully Synthetic Globo H Antigen Results in Antibodies against Human Cancer Cells: A Combined Chemical—Immunological Approach to the Fashioning of an Anticancer Vaccine." *Angew. Chem. Int. Ed.* 1997, 36, 125-128. (d) Allen, J. R.; Allen, J. G.; Zhang, X.-F.; Williams, L. J.; Zatorski, A.; Ragupathi, G.; Livingston, P. O.; Danishefsky, S. J. "A Second Generation Synthesis of the MBr1 (Globo-H) Breast Tumor Antigen: New Application of then-Pentenyl Glycoside Method for Achieving Complex Carbohydrate Protein Linkages." *Chem. Eur. J.* 2000, 6, 1366-1375.

(30) (a) Ragupathi, G.; Slovin, S. F.; Adluri, S.; Sames, D.; Kim, I. J.; Kim, H. M.; Spassova, M.; Bornmann, W. G.; Lloyd, K. O.; Scher, H. I.; Livingston, P. O.; Danishefsky, S. J. "A Fully Synthetic Globo H Carbohydrate Vaccine Induces a Focused Humoral Response in Prostate Cancer Patients: A Proof of Principle." *Angew. Chem. Int. Ed.* 1999, 38, 563-566. (b) Slovin, S. F.; Ragupathi, G.; Adluri, S.; Ungers, G.; Terry, K.; Kim, S.; Spassova, M.; Bornmann, W. G.; Fazzari, M.; Dantis, L.; Olkiewicz, K.; Lloyd, K. O.; Livingston, P. O.; Danishefsky, S. J.; Scher, H. I. "Carbohydrate vaccines in cancer: Immunogenicity of a fully synthetic globo H hexasaccharide conjugate in man." *Proc. Natl. Acad. Sci. U.S.A.* 1999, 96, 5710-5715. (c) Gilewski, T.; Ragupathi, G.; Bhuta, S.; Williams, L. J.; Musselli, C.; Zhang, X.-F.; Bencsath, K. P.; Panageas, K. S.; Chin, J.; Hudis, C. A.; Norton, L.; Houghton, A. N.; Livingston, P. O.; Danishefsky, S. J. "Immunization of metastatic breast cancer patients with a fully synthetic globo H conjugate: A phase I trial." *Proc. Natl. Acad. Sci. U.S.A.* 2001, 98, 3270-3275.

(31) (a) Ragupathi, G.; Koide, F.; Livingston, P. O.; Cho, Y. S.; Endo, A.; Wan, Q.; Spassova, M. K.; Keding, S. J.; Allen, J.; Ouerfelli, O.; Wilson, R. M.; Danishefsky, S. J. "Preparation and Evaluation of Unimolecular Pentavalent and Hexavalent Antigenic Constructs Targeting Prostate and Breast Cancer: A Synthetic Route to Anticancer Vaccine Candidates." *J. Am. Chem. Soc.* 2006, 128, 2715-2725. (b) Zhu, J.; Wan, Q.; Lee, D.; Yang, G.; Spassova, M. K.; Ouerfelli, O.; Ragupathi, G.; Damani, P.; Livingston, P. O.; Danishefsky, S. J. "From Synthesis to Biologics: Preclinical Data on a Chemistry Derived Anticancer Vaccine." *J. Am. Chem. Soc.* 2009, 131, 9298-9303. PMCID: PMC2716484.

(32) Geng, X.; Dudkin, V. Y.; Mandal, M.; Danishefsky, S. J. "In pursuit of carbohydrate-based HIV vaccines, part 2: The total synthesis of high-mannose-type gp120 fragments—evaluation of strategies directed to maximal convergence." *Angew. Chem. Int. Ed.* 2004, 43, 2562-2565.

(33) (a) Krauss, I. J.; Joyce, J. G.; Finnefrock, A. C.; Song, H. C.; Dudkin, V. Y.; Geng, X.; Warren, J. D.; Chastain, M.; Shiver, J. W.; Danishefsky, S. J. "Fully synthetic carbohydrate HIV antigens designed on the logic of the 2G12 antibody." *J. Am. Chem. Soc.* 2007, 129, 11042-

11044. (b) Joyce, J. G.; Krauss, I. J.; Song, H. C.; Opalka, D. W.; Grimm, K. M.; Nahas, D. D.; Esser, M. T.; Hrin, R.; Feng, M.; Dudkin, V. Y.; Chastain, M.; Shiver, J. W.; Danishefsky, S. J. "An oligosaccharide-based HIV-1 2G12 mimotope vaccine induces carbohydrate-specific antibodies that fail to neutralize HIV-1 virions." *Proc. Natl. Acad. Sci. U.S.A.* 2008, 105, 15684-15689. PMCID: PMC2562416.

(34) Wilson, R. M.; Danishefsky, S. J. "Promising Agents at the Interface of Biology and Oncology Derived through Chemical Synthesis" *Pure and Applied Chem.* 2007, 79, 2189-2216.

(35) (a) Anisfeld, S. T.; Lansbury, P. T. "A convergent approach to the chemical synthesis of asparagine-linked glycopeptides." *J. Org. Chem.* 1990, 55, 5560-5562. (b) Cohen-Anisfeld, S. T.; Lansbury, P. T. "A practical, convergent method for glycopeptide synthesis." *J. Am. Chem. Soc.* 1993,115, 10531-10537.

(36) (a) Miller, J. S.; Dudkin, V. Y.; Lyon, G. J.; Muir, T. W.; Danishefsky, S. J. "Toward fully synthetic N-linked glycoproteins." *Angew. Chem. Int. Ed.* 2003, 42, 431-434. (b) Warren, J. D.; Miller, J. S.; Keding, S. J.; Danishefsky, S. J. "Toward fully synthetic glycoproteins by ultimately convergent routes: A solution to a long-standing problem." *J. Am. Chem. Soc.* 2004, 126, 6576-6578.

(37) Mandal, M.; Dudkin, V. Y.; Geng, X.; Danishefsky, S. J. "In pursuit of carbohydrate-based HIV vaccines, part 1: The total synthesis of hybrid-type gp120 fragments." *Angew. Chem. Int. Ed.* 2004, 43, 2557-2561.

(38) (a) Nagorny, P.; Sane, N.; Fasching, B.; Aussedat, B.; Danishefsky, S. J. "Probing the Frontiers of Glycoprotein Synthesis: The Fully Elaborated β-Subunit of the Human Follicle-Stimulating Hormone" *Angew. Chem. Int. Ed.* 2012, 51, 975-979. PMCID: PMC3285374. (b) Aussedat, B.; Fasching, B.; Johnston, E.; Sane, N.; Nagorny, P.; Danishefsky, S. J. "Total Synthesis of the α-Subunit of the Human Glycoprotein Hormones: Toward Fully Synthetic Homogeneous Human Follicle-Stimulating Hormone" *J. Am. Chem. Soc.* 2012, 134, 3532-3541. PMCID: PMC3288947.

(39) Wang, P.; Aussedat, B.; Vohra, Y.; Danishefsky, S. J. "An Advance in the Chemical Synthesis of Homogeneous N-Linked Glycopolypeptides by Convergent Aspartylation" *Angew. Chem. Int. Ed.* 2012, 51, 11571-11575. PMCID: PMC3500778.

(40) Haack, T.; Mutter, M. "Serine derived oxazolidines as secondary structure disrupting, solubilizing building blocks in peptide synthesis." *Tetrahedron Lett.* 1992, 33, 1589-1592.

(41) Dawson, P. E.; Muir, T. W.; Clark-Lewis, I.; Kent, S. B. H. "Synthesis of proteins by native chemical ligation" *Science* 1994, 266, 776-779.

(42) This kind of logic was first demonstrated using Raney nickel for the desulfurization: Yan, L. Z.; Dawson, P. E. "Synthesis of peptides and proteins without cysteine residues by native chemical ligation combined with desulfurization." *J. Am. Chem. Soc.* 2001, 123, 526-533.

(43) Wan, Q.; Danishefsky, S. J. "Free Radical-Based, Specific Desulfurization of Cysteine: A Powerful Advance in the Synthesis of Polypeptides and Glycopolypeptides" *Angew. Chem. Int. Ed.* 2007, 46, 9248-9252.

(44) Chen, J.; Wan, Q.; Yuan, Y.; Zhu, J. L.; Danishefsky, S. J. "Native Chemical Ligation at Valine: A Contribution to Peptide and Glycopeptide Synthesis" *Angew. Chem. Int. Ed.* 2008, 47, 8521-8524. PMCID: PMC2756581.

(45) Chen, J.; Wang, P.; Zhu, J.; Wan, Q.; Danishefsky, S. J. "A Program for Ligation at Threonine Sites: Application to the Controlled Total Synthesis of Glycopeptides" *Tetrahedron* 2009, 66, 2277-2283. PMCID: PMC2925322.

(46) Tan, Z.; Shang, S.; Danishefsky, S. J. "Insights into the Finer Issues of Native Chemical Ligation: An Approach to Cascade Ligations" *Angew. Chem. Int. Ed.* 2010, 49, 9500-9503. PMCID: PMC3199326.

(47) (a) Shang, S.; Tan, Z.; Dong, S.; Danishefsky, S. J. "An Advance in Proline Ligation" *J. Am. Chem. Soc.* 2011, 133, 10784-10786. PMCID: PMC3135777. (b) Townsend, S. D.; Tan, Z.; Dong, S.; Shang, S.; Brailsford, J. A.; Danishefsky, S. J. Advances in Proline Ligation. *J. Am. Chem. Soc.* 2012, 134, 3912-3916. PMCID: PMC3306728.

(48) (a) Shang, S.; Tan, Z.; Danishefsky, S. J. "Application of the Logic of Cysteine-Free Native Chemical Ligation to the Synthesis of Human Parathyroid Hormone (hPTH)" *Proc. Natl. Acad. Sci.* 2011, 108, 5986-5989. PMCID: PMC3076867. (b) Dong, S.; Shang, S.; Li, J.; Tan, Z.; Dean, T.; Maeda, A.; Gardella, T. J.; Danishefsky, S. J. "Engineering of Therapeutic Polypeptides Through Chemical Synthesis: Early Lessons from Human Parathyroid Hormone and Analogues" *J. Am. Chem. Soc.* 2012, 134, 15122-15129. PMCID: PMC3462362.

(49) Li, J.; Dong, S.; Townsend, S. D.; Dean, T.; Gardella, T. J.; Danishefsky, S. J. "Chemistry as an expanding resource in protein science: Fully synthetic and fully active human parathyroid hormone related protein (1-141)"*Angew. Chem. Int. Ed.* 2012, 51, 12263-12267. PMCID: PMC Journal—In Progress.

(50) Mao, Y.; Wang, L.; Gu, C.; Herschhorn, A.; Xiang, S.; Haim, H.; Yang, X.; Sodroski, J. "Subunit organization of the membrane-bound HIV-1 envelope glycoprotein trimer." *Nat. Struct. Mol. Biol.* 2012, 19, 893-9.

(51) Bar, K. J.; Tsao, C.; Iyer, S. S.; Decker, J. M.; Yang, Y.; Bonsignori, M.; Chen, X.; Hwang, K.-K.; Montefiori, D. C.; Liao, H.-X.; Hraber, P.; Fischer, W.; Li, H.; Wang, S.; Sterrett, S.; Keele, B. F.; Ganusov, V. V.; Perelson, A. S.; Korber, B. T.; Georgiev, I.; McLellan, J. S.; Pavlicek, J. W.; Gao, F.; Haynes, B. F.; Hahn, B. H.; Kwong, P. D.; Shaw, G. M. "Early low-titer neutralizing antibodies impede HIV-1 replication and select for virus escape." *PLoS Pathog.* 2012, 8, e1002721.

(52) Li, H.; Li, B.; Song, H.; Breydo, L.; Baskakov, I. V.; Wang, L.-X. "Chemoenzymatic synthesis of HIV-1 V3 glycopeptides carrying two N-glycans and effects of glycosylation on the peptide domain." *J. Org. Chem.* 2005, 70, 9990-9996.

(53) Wilson, R. M.; Danishefsky, S. J. "Small molecule natural products in the discovery of therapeutic agents: The synthesis connection." *J. Org. Chem.* 2006, 71, 8329-8351.

(54) (a) Imperiali, B.; O'Connor, S. E. "Effect of N-linked glycosylation on glycopeptide and glycoprotein structure." *Curr. Opin. Chem. Biol.* 1999, 3, 643-649. (b) Meyer, B.; Möller, H. "Conformation of Glycopeptides and Glycoproteins." In *Glycopeptides and Glycoproteins*; Wittmann, V., Ed.; Topics in Current Chemistry; Springer Berlin Heidelberg, 2007; pp. 187-251.

(55) Moseri, A.; Tantry, S.; Sagi, Y.; Arshava, B.; Naider, F.; Anglister, J. "An optimally constrained V3 peptide is a better immunogen than its linear homolog or HIV-1 gp120." *Virology* 2010, 401, 293-304.

(56) Muir, T. W. "Semisynthesis of Proteins by Expressed Protein Ligation." *Annu. Rev. Biochem.* 2003, 72, 249-289.

(57) (a) Doores, K. J.; Bonomelli, C.; Harvey, D. J.; Vasiljevic, S.; Dwek, R. A.; Burton, D. R.; Crispin, M.; Scanlan, C. N. "Envelope glycans of immunodeficiency virions are almost entirely oligomannose antigens." *Proc. Natl. Acad. Sci. U.S.A.* 2010, 107, 13800-13805. (b) Bonomelli, C.; Doores, K. J.; Dunlop, D. C.; Thaney, V.; Dwek, R. A.; Burton, D. R.; Crispin, M.; Scanlan, C. N. "The glycan shield of HIV is predominantly oligomannose independently of production system or viral clade." *PLoS ONE* 2011, 6, e23521.

(58) (a) Wang, P.; Zhu, J.; Yuan, Y.; Danishefsky, S. J. "Total synthesis of the 2,6-sialylated immunoglobulin G glycopeptide fragment in homogeneous form." *J. Am. Chem. Soc.* 2009, 131, 16669-16671. PMCID: PMC2786312. (b) Walczak, M. A.; Danishefsky, S. J. "Solving the convergence problem in the synthesis of triantennary N-glycan relevant to prostate-specific membrane antigen (PSMA)." *J. Am. Chem. Soc.* 2012, 134, 16430-16433. PMCID: PMC3470013.

(59) Likhosherstov, L. M.; Novikova, O. S.; Derevitskaja, V. A.; Kochetkov, N. K. "A new simple synthesis of amino sugar β-D-glycosylamines." *Carbohydr. Res.* 1986, 146, C1-C5.

(60) Mouquet, H.; Scharf, L.; Euler, Z.; Liu, Y.; Eden, C.; Scheid, J. F.; Halper-Stromberg, A.; Gnanapragasam, P. N. P.; Spencer, D. I. R.; Seaman, M. S.; Schuitemaker, H.; Feizi, T.; Nussenzweig, M. C.; Bjorkman, P. J. "Complex-type N-glycan recognition by potent broadly neutralizing HIV antibodies." *Proc. Natl. Acad. Sci. U.S.A.* 2012, 109, E3268-E3277.

(61) Nagorny, P.; Fasching, B.; Li, X.; Chen, G.; Aussedat, B.; Danishefsky, S. J. "Toward fully synthetic homogeneous β-human follicle-stimulating hormone (β-hFSH) with a biantennary N-linked dodecasaccharide. Synthesis of β-hFSH with chitobiose units at the natural linkage sites." *J. Am. Chem. Soc.* 2009, 131, 5792-5799.

(62) Seko, A.; Koketsu, M.; Nishizono, M.; Enoki, Y.; Ibrahim, H. R.; Juneja, L. R.; Kim, M.; Yamamoto, T. "Occurrence of a sialylglycopeptide and free sialylglycans in hen's egg yolk." *Biochim. Biophys. Acta, Gen. Subj.* 1997, 1335, 23-32.

(63) (a) Kajihara, Y.; Suzuki, Y.; Yamamoto, N.; Sasaki, K.; Sakakibara, T.; Juneja, L. R. "Prompt Chemoenzymatic Synthesis of Diverse Complex-Type Oligosaccharides and Its Application to the Solid-Phase Synthesis of a Glycopeptide with Asn-Linked Sialyl-undeca- and Asialo-nonasaccharides." *Chem. Eur. J.* 2004, 10, 971-985. (b) Murakami, M.; Okamoto, R.; Izumi, M.; Kajihara, Y. "Chemical Synthesis of an Erythropoietin Glycoform Containing a Complex-type Disialyloligosaccharide." *Angew. Chem. Int. Ed.* 2012, 51, 3567-3572.

(64) Knuf, M.; Kowalzik, F.; Kieninger, D. "Comparative effects of carrier proteins on vaccine-induced immune response." *Vaccine* 2011, 29, 4881-4890.

(65) Broker, M.; Dull, P. M.; Rappuoli, R.; Costantino, P. "Chemistry of a new investigational quadrivalent meningococcal conjugate vaccine that is immunogenic at all ages." *Vaccine* 2009, 27, 5574-5580.

(66) Stephanopoulos, N.; Francis, M. B. "Choosing an effective protein bioconjugation strategy." *Nat. Chem. Biol.* 2011, 7, 876-884.

(67) Van de Vijver, P.; Schmitt, M.; Suylen, D.; Scheer, L.; Thomassen, M. C. L. G. D.; Schurgers, L. J.; Griffin, J. H.; Koenen, R. R.; Hackeng, T. M. "Incorporation of Disulfide Containing Protein Modules into Multivalent Antigenic Conjugates: Generation of Antibodies against the Thrombin-Sensitive Region of Murine Protein S." *J. Am. Chem. Soc.* 2012, 134, 19318-19321.

(68) (a) Dirksen, A.; Hackeng, T. M.; Dawson, P. E. "Nucleophilic Catalysis of Oxime Ligation." *Angew. Chem. Int. Ed.* 2006, 45, 7581-7584. (b) Dirksen, A.; Dawson, P. E. "Rapid Oxime and Hydrazone Ligations with Aromatic Aldehydes for Biomolecular Labeling." *Bioconjugate Chem.* 2008, 19, 2543-2548.

(69) Cease, K. B.; Margalit, H.; Cornette, J. L.; Putney, S. D.; Robey, W. G.; Ouyang, C.; Streicher, H. Z.; Fischinger, P. J.; Gallo, R. C.; DeLisi, C. "Helper T-cell antigenic site identification in the acquired immunodeficiency syndrome virus gp120 envelope protein and induction of immunity in mice to the native protein using a 16-residue synthetic peptide." *Proc. Natl. Acad. Sci. U.S.A.* 1987, 84, 4249-4253.

(70) Hart, M. K.; Palker, T. J.; Matthews, T. J.; Langlois, A. J.; Lerche, N. W.; Martin, M. E.; Scearce, R. M.; McDanal, C.; Bolognesi, D. P.; Haynes, B. F. "Synthetic peptides containing T and B cell epitopes from human immunodeficiency virus envelope gp120 induce anti-HIV proliferative responses and high titers of neutralizing antibodies in rhesus monkeys." *J. Immunol.* 1990, 145, 2677-2685.

What is claimed is:

1. A synthetic peptide of SEQ ID NO: 2, 4, 6, or 7, wherein the peptide is glycosylated at positions Asn301 and Asn 332, wherein the numbering is based upon the prototypic HIV-1 isolate HXB-2 and wherein the peptide is cyclic via endogenous cysteines.

2. The synthetic peptide of claim 1 wherein the peptide is of SEQ ID NO: 2.

3. The synthetic peptide of claim 1, wherein the peptide is glycosylated with oligomannose.

4. The synthetic peptide of claim 1, wherein the peptide has $Man_9GlcNAc_2$ glycans.

5. The synthetic peptide of claim 1, wherein the peptide further comprises T helper peptide.

6. A composition comprising the synthetic peptide of any one of claims 1-5, wherein the composition comprises purified homogenously glycosylated peptides.

7. The composition of claim 6, wherein the glycosylation pattern is homogenous on all peptides of SEQ ID NO: 2, 4, 6, or 7 in the composition.

8. The composition of claim 6 further comprising an adjuvant.

9. A method of inducing antibodies against HIV-1 in a subject, the method comprising administering to the subject the composition of claim 6 in an amount sufficient to induce the anti-HIV-1 antibodies.

10. The method of claim 9, wherein the composition comprises the synthetic peptide of SEQ ID NO: 2 glycosylated at positions Asn301 and Asn 332 with $Man_9GlcNAc_2$.

11. The method of claim 9 wherein said subject is a human.

12. The synthetic peptide of claim 2, wherein the peptide is glycosylated with oligomannose.

13. The synthetic peptide of claim 2, wherein the peptide has Man9GlcNAc2 glycans.

14. The synthetic peptide of claim 2, wherein the peptide further comprises a T helper peptide.

15. A composition comprising the synthetic peptide of any one of claims 12-14.

16. The composition of claim 15 further comprising an adjuvant.

17. A method of inducing antibodies against HIV-1 in a subject, the method comprising administering to the subject the composition of claim 15 in an amount sufficient to induce the anti-HIV-1 antibodies.

* * * * *

SEQUENCE LISTING

```
<160> NUMBER OF SEQ ID NOS: 14

<210> SEQ ID NO 1
<211> LENGTH: 43
<212> TYPE: PRT
<213> ORGANISM: Human immunodeficiency virus 1

<400> SEQUENCE: 1

Glu Ile Asn Cys Thr Arg Pro Asn Asn Asn Thr Arg Lys Ser Ile His
1               5                   10                  15

Ile Gly Pro Gly Arg Ala Phe Tyr Thr Thr Gly Glu Ile Ile Gly Asp
            20                  25                  30

Ile Arg Gln Ala His Cys Asn Ile Ser Arg Ala
        35                  40

<210> SEQ ID NO 2
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Ile Asn Cys Thr Arg Pro Asn Asn Asn Thr Arg Pro Gly Glu Ile
```

```
                1               5                  10                  15
Ile Gly Asp Ile Arg Gln Ala His Cys Asn Ile Ser Arg Ala
            20                  25                  30

<210> SEQ ID NO 3
<211> LENGTH: 43
<212> TYPE: PRT
<213> ORGANISM: Human immunodeficiency virus 1

<400> SEQUENCE: 3

Lys Ile Glu Cys Thr Arg Pro Asn Asn Lys Thr Arg Thr Ser Ile Arg
1               5                   10                  15

Ile Gly Pro Gly Gln Ala Phe Tyr Ala Thr Gly Gln Val Ile Gly Asp
            20                  25                  30

Ile Arg Glu Ala Tyr Cys Asn Ile Ser Glu Ser
        35                  40

<210> SEQ ID NO 4
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Lys Ile Glu Cys Thr Arg Pro Asn Asn Lys Thr Arg Pro Gly Gln Val
1               5                   10                  15

Ile Gly Asp Ile Arg Glu Ala Tyr Cys Asn Ile Ser Glu Ser
            20                  25                  30

<210> SEQ ID NO 5
<211> LENGTH: 46
<212> TYPE: PRT
<213> ORGANISM: Human immunodeficiency virus 1

<400> SEQUENCE: 5

Glu Ile Thr Cys Thr Arg Pro Asn Asn Asn Thr Arg Lys Ser Ile Pro
1               5                   10                  15

Met Gly Pro Gly Lys Ala Phe Tyr Ala Arg Gly Asp Ile Thr Gly Asp
            20                  25                  30

Ile Arg Lys Ala Tyr Cys Glu Ile Asn Gly Thr Glu Trp His
        35                  40                  45

<210> SEQ ID NO 6
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Ile Thr Cys Thr Arg Pro Asn Asn Asn Thr Arg Pro Gly Asp Ile
1               5                   10                  15

Thr Gly Asp Ile Arg Lys Ala Tyr Cys Glu Ile Asn Gly Thr Glu Trp
            20                  25                  30

His

<210> SEQ ID NO 7
<211> LENGTH: 43
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 7

Lys Ile Glu Cys Thr Arg Pro Asn Asn Lys Thr Arg Thr Ser Ile Arg
1               5                   10                  15

Ile Gly Pro Gly Gln Ala Phe Tyr Ala Thr Gly Gln Val Ile Gly Asp
            20                  25                  30

Ile Arg Glu Ala Tyr Cys Asn Ile Ser Glu Ser
        35                  40

<210> SEQ ID NO 8
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Ile Asn Cys Thr Arg Pro Asn Asn Asn Thr Arg Pro Gly Glu Ile
1               5                   10                  15

Ile Gly Asp Ile Arg Gln Ala His Cys Asn Ile Ser Arg Ala
            20                  25                  30

<210> SEQ ID NO 9
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Ile Thr Asp Glu Val Arg Asn Cys Ser Phe Asn Met Thr Thr Glu Leu
1               5                   10                  15

Arg Asp Lys Lys Gln Lys Val His Ala Leu Phe Tyr Lys Leu Asp Ile
            20                  25                  30

Val Pro Ile
        35

<210> SEQ ID NO 10
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Glu Ile Asn Cys Thr Arg Pro Asn Asp Asn Thr Arg Pro Gly Glu Ile
1               5                   10                  15

Ile Gly Asp Ile Arg Gln Ala His Cys Asp Ile Ser Arg Ala
            20                  25                  30

<210> SEQ ID NO 11
<211> LENGTH: 24
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Glu Ile Asn Cys Thr Arg Pro Asn Asp Asn Thr Arg Pro Gly Glu Ile
1               5                   10                  15

Ile Gly Asp Ile Arg Gln Ala His
            20

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Cys Asp Ile Ser Arg Ala
1               5

<210> SEQ ID NO 13
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Glu Ile Asn Cys Thr Arg Pro Asn Asn Asn Thr Arg Pro Gly Glu Ile
1               5                   10                  15

Ile Gly Asp Ile Arg Gln Ala His
            20

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Cys Asn Ile Ser Arg Ala
1               5
```